US009896693B2

(12) United States Patent
Portereiko et al.

(10) Patent No.: US 9,896,693 B2
(45) Date of Patent: Feb. 20, 2018

(54) PROMOTER, PROMOTER CONTROL ELEMENTS, AND COMBINATIONS, AND USES THEREOF

(71) Applicant: Ceres, Inc., Thousand Oaks, CA (US)

(72) Inventors: Michael F. Portereiko, Thousand Oaks, CA (US); Nickolai Alexandrov, Thousand Oaks, CA (US)

(73) Assignee: Cres, Inc., Thousand Oaks, CA (US)

( * ) Notice: Subject to any disclaimer, the term of this patent is extended or adjusted under 35 U.S.C. 154(b) by 547 days.

(21) Appl. No.: 14/048,620

(22) Filed: Oct. 8, 2013

(65) Prior Publication Data

US 2014/0096286 A1    Apr. 3, 2014

Related U.S. Application Data

(60) Division of application No. 12/895,475, filed on Sep. 30, 2010, now Pat. No. 8,592,646, which is a continuation of application No. PCT/US2009/038792, filed on Mar. 30, 2009.

(60) Provisional application No. 61/041,018, filed on Mar. 31, 2008.

(51) Int. Cl.
*C12N 15/82* (2006.01)

(52) U.S. Cl.
CPC ..... *C12N 15/8222* (2013.01); *C12N 15/8216* (2013.01)

(58) Field of Classification Search
None
See application file for complete search history.

(56) References Cited

U.S. PATENT DOCUMENTS

| | | |
|---|---|---|
| 4,668,777 A | 5/1987 | Caruthers et al. |
| 5,015,580 A | 5/1991 | Christou et al. |
| 5,362,865 A | 11/1994 | Austin |
| 5,380,831 A | 1/1995 | Adang et al. |
| 5,384,253 A | 1/1995 | Krzyzek et al. |
| 5,436,391 A | 7/1995 | Fujimoto et al. |
| 5,508,184 A | 5/1996 | Negrutiu et al. |
| 5,538,880 A | 7/1996 | Lundquist et al. |
| 5,550,318 A | 8/1996 | Adams et al. |
| 5,591,616 A | 1/1997 | Hiei et al. |
| 5,659,122 A | 8/1997 | Austin |
| 5,824,877 A | 10/1998 | Hinchee et al. |
| 5,981,840 A | 11/1999 | Zhao et al. |
| 6,160,208 A | 12/2000 | Lundquist et al. |
| 6,384,301 B1 | 5/2002 | Martinell et al. |
| 6,399,861 B1 | 6/2002 | Anderson et al. |
| 6,403,865 B1 | 6/2002 | Koziel et al. |
| 7,098,324 B2 | 8/2006 | Haigler et al. |
| 7,294,760 B2 | 11/2007 | Ruezinsky |
| 8,592,646 B2 | 11/2013 | Portereiko et al. |
| 2007/0162995 A1 | 7/2007 | Good |

FOREIGN PATENT DOCUMENTS

| | | | |
|---|---|---|---|
| CA | 2067477 | 11/1992 | |
| JP | 2005185101 | * 7/2005 | ............. C12N 15/09 |

OTHER PUBLICATIONS

Ohta et al. High-level expression of a sweet potato sporamin gene promoter: B-glucuroidase (GUS) fusion gene in the stems of transgenic tobacco plants is conferred by multiple cell type-specific regulatory elements. Mol. Gen. Genet. 1991. 225: 369-378.*
Bedell et al. Sorghum genome sequencing by methylation filtration. PLOS Biology. 3(1): e13. pp. 103-115.*
Grabherr et al. Exploiting nucleotide composition to engineer promoters. PLoSOne. 2011. 6(5): e20136: pp. 1-10.*
Moyle et al. The pineapple AcMADS1 promoter confers high level of expression in tomato and *Arabidopsis* flowering and fruiting tissues, but AcMADS1 does not complement the tomato LeMADS-RIN (rin) mutant. Plant Molecular Biology. 2014. 86: 395-407.*
Rani et al. Comprehensive computational analysis of cis-regulatory elements in 5' regulatory region of ADP glucose pyrophosphorylase in differentplants. International Journal of Scientific & Engineering Research. 2014. 5: 1594-1604.*
Rombauts et al. PlantCARE, a plant cis-acting regulatory element database. Nucleic Acids Research. 1999. 27(1): 295-296.*
Ross et al. Activation of the *Oryza sativa* non-symbiotic haemoglobin-2 promoter by the cytokinin-regulated transcription factor, ARR1. Journal of Experimental Biology. 2004. 55(403): 1721-1731.*
Kim et al. A 20 nucleotide upstream element is essential for the nopaline synthase (nos) promoter activity. Plant Molecular Biology. 1994. 24: 105-117.*
Authorized Officer, Kim Jung Tae, International Search Report & Written Opinion, PCT/US/2009/038792, dated Dec. 21, 2009, dated Dec. 22, 2009, 13 pages.
Authorized Officer, Philippe Becamel, International Bureau of WIPO, International Preliminary Report on Patentability, PCT/US/2009/038792, dated Oct. 14, 2010, 6 pages.
Xinqin Feng, Agent, The Patent Office of the People's Republic of China, Office Action issued in Chinese Application No. CN200980116964.X, dated Feb. 16, 2012, 6 pages (no new art).
Acevedo-Hernandez et al., "Sugar and ABA responsiveness of a minimal RBCS light-responsive unit is mediated by direct binding of ABI4," *Plant J.*, 2005, 43:506-519.
Alonso-Blanco et al., "Genetic and molecular analyses of natural variation indicate CBF2 as a candidate gene for underlying a freezing tolerance quantitative trait locus in *Arabidopsis*," *Plant Physiology*, 2005, 139:1304-1312.

(Continued)

*Primary Examiner* — Ashley K Buran
(74) *Attorney, Agent, or Firm* — Dentons US LLP

(57) ABSTRACT

The present document is directed to promoter sequences and promoter control elements, polynucleotide constructs comprising the promoters and control elements, and methods of identifying the promoters, control elements, or fragments thereof. The document further relates to the use of such promoters or promoter control elements to modulate transcript levels in plants, and plants containing such promoters or promoter control elements.

17 Claims, 36 Drawing Sheets

(56) References Cited

OTHER PUBLICATIONS

Figure 1:
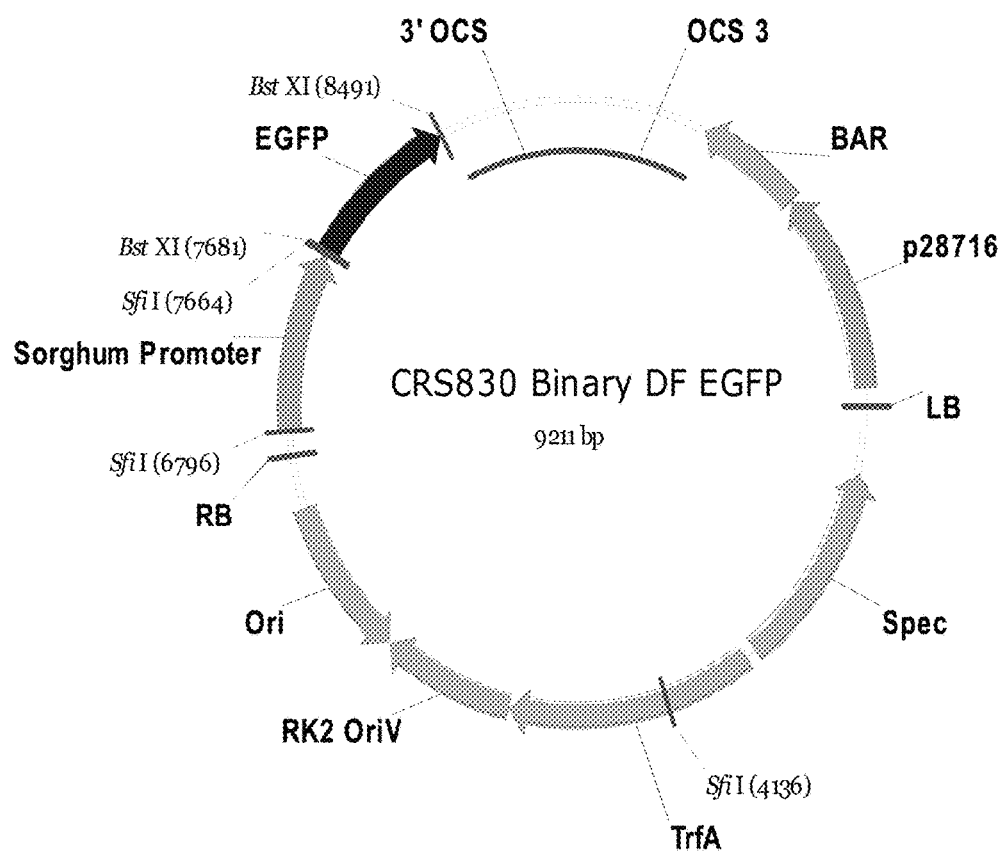

Armaleo et al., "Biolistic nuclear transformation of *Saccharomyces cerevisiae* and other fungi," *Current Genetics*, 1990, 17:97-103.
Auch et al. "Exon Trap Cloning: Using PCR to Rapidly Detect and Clone Exons from Genomic DNA Fragments," *Nucleic Acids Research*, 1990, 18(22):6743.
Ballas et al. "Efficient functioning of plant promoters and poly(A) sites in Xenopus oocytes," *Nucleic Acids Research*, 1989, 17:7891-7903.
Benedict et al., "The CBF1-dependent low temperature signalling pathway, regulon and increase in freeze tolerance are conserved in *Populus* spp.," *Plant Cell Environ.*, 2006, 29:1259-1272.
Block et al., "Functional borders, genetic fine structure, and distance requirements of cis elements mediating light responsiveness of the parsley chalcone synthase promoter," *Proc Natl Acad Sci USA*, 1990, 87:5387-5391.
Bouvier et al. "Induction and Control of Chromoplast-specific Carotenoid Genes by Oxidative Stress" *J. Biol. Chem.*, 1998, 273:30651-59.
Bradshaw et al., "A new vector for recombination-based cloning of large DNA fragments from yeast artificial chromosomes," *Nucl. Acids. Rec.*, 1995, 23(23):4850-4856.
Bray, "Plant responses to water deficit," *Trends Plant Sci.*, 1997, 2:48-54.
Burke et al., "Cloning of large segments of exogenous DNA into yeast by means of artificial chromosome vectors," *Science*, 1987, 236:806-812.
Busk and Pages, "Regulation of abscisic acid-induced transcription," *Plant Mol Biol*, 1998, 37:425-435.
Canton and Quail "Both phyA and phyB mediate light-imposed repression of PHYA gene expression in *Arabidopsis*" *Plant Physiol.*, 1999, 121:1207-16.
Carrari et al., "Genetic mapping of the sorghum bicolor vp1 gene and its relationship with preharvest sprouting resistance," *Genome*, 2003, 46:253-258.
Casadaban et al., "In vitro gene fusions that join an enzymatically active bata-galactosidase segment to amino-terminal fragments of exogenous proteins: *Escherichia coli* plasmid vectors for the detection and cloning of translational initiation signals," *J. Bacteriol*, 1980, 143:971-980.
Castresana et al., "Both positive and negative regulatory elements mediate expression of a photoregulated CAB gene from *Nicotiana plumbaginifolia*," *EMBO J*, 1988, 7:1929-1936.
Chenna et al., "Multiple sequence alignment with the Clustal series of programs" *Nucleic Acids Res.*, 2003, 31(13):3497-3500.
Cheong et al., "BWMK1, a rice mitogen-activated protein kinase, locates in the nucleus and mediates pathogenesis-related gene expression by activation of a transcription factor1," *Plant Physiol.*, 2003, 132:1961-1972.
Comai et al., "Expression in plants of a mutant aroA gene from *Salmonella typhimurium* confers tolerance to glyphosate," *Nature*, 1985, 317:741-744.
Curaba et al., "AtGA$_{30x2}$, a key gene responsible for bioactive gibberellin biosynthesis, is regulated during embryogenesis by LEAFY COTYLEDON$_2$ and FUSCA$_3$ in *Arabidopsis*," *Plant Physiol.*, 2004.
El Maarouf et al. "Enzymatic activity and gene expression under water stress of phospholipase D in two cultivars of *Vigna unguiculata* L. Walp. differing in drought tolerance" *Plant Mol. Biol.*, 1999.
Elliott and Shirsat, "Promoter regions of the extA extensin gene from *Brassica napus* control activation in response to wounding and tensile stress," *Plant Mol Biol*, 1998, 37:675-687.
Elmayan and Tepfer, "Evaluation in tobacco of the organ specificity and strength of the rol D promoter, domain A of the 35S promoter and the 35Ss 2 promoter," *Transgenic Res.*, 1995, 4(6):388-396.
Escudero et al., "T-DNA transfer in meristematic cells of maize provided with intracellular *Agrobacterium*," *Plant J.*, 1996, 10(2):355-360.

Farmer and Ryan, "Interplant communication: Airborne methyl jasmonate induces synthesis of proteinase inhibitors in plant leaves," *Proc Natl Acad Sci USA*, 1990, 87:7713-7716.
Folter and Angenent, "Trans meets cis in MADS science," *Trends Plant Sci.*, 2006, 11:224-231.
Foster et al., "Genetic regulation of development in sorghum bicolor[1]: VIII. Shoot Growth, Tillering, Flowering, Gibberellin Biosynthesis, and Phytochrome Levels are Differentially Affected by Dosage of the ma$_3^R$ Allele," *Plant Physiology*, 1994, 105:941-948.
Franco et al., "Regulation of antioxidant enzyme gene expression in response to oxidative stress and during differentiation of mouse skeletal muscle," *Free Radic Biol Med*, 1999, 27:1122-32.
Frischauf et al., "Lambda replacement vectors carrying polylinker sequences," *J. Mol. Biol.*, 1983, 170:827-842.
Fu, et al., "Empty pericarp2 encodes a negative regulatory of the heat shock response and is required for maize embryogenesis," *The Plant Cell*, 2002, 14:3119-3132.
Fujimoto et al., "*Arabidopsis* ethylene-responsive element binding factors act as transcriptional activators or repressors of GCC box-mediated gene expression," *Plant Cell*, 2000, 12:393-404.
Gasser et al., "Studies on Scaffold Attachment Sites and Their Relation to Genome Function," *Int. Rev Cyto*, 1990, 119:57-96.
Germain and Ricard, "Two ldh genes from tomato and their expression in different organs, during fruit ripening and in response to stress," *Plant Mol Biol.*, 1997, 35:949-54.
Gilmour et al. "Low temperature regulation of the *Arabidopsis* CBF family of AP2 transcriptional activators as an early step in cold-induced COR gene expression," *Plant Journal*, 1998, 16(4):433-442.
Gordon-Kamm et al., "Transformation of maize cells and regeneration of fertile transgenic plants," *Plant Cell*, 1990, 2:603-618.
Gossler et al., "Mouse embryonic stem cells and reporter constructs to detect developmentally regulated genes," *Science*, 1989, 244:463-465.
Grace et al., "Sequence and spacing of TATA box elements are critical for accurate initiation from the β-phaseolin promoter," *J. Biol Chem*, 2004, 279:8102-8110.
Gruber et al. "Chapter 7: Vectors for plant transformation," In Methods in Plant Molecular Biology & Biotechnology, Glich et al., Eds. pp. 89-119, CRC Press, 1993.
Guan et al., "Cis-elements and trans-factors that regulate expression of the maize Cat1 antioxidant gene in response to ABA and osmotic stress: H202 is the likely intermediary signaling molecule for the response," *Plant J.*, 2000, 22:87-95.
Gubler et al., "Gibberellin-regulated expression of myb gene in barley aleurone cells: evidence for Myb transactivation of a high-p1 [alpha]-amylase gene promoter," *Plant Cell*, 1995, 7:1879-1891.
Gubler et al., "Target genes and regulatory domains of the GAMYB transcriptional activator in cereal aleurone," *Plant J.*, 1999, 17:1-9.
Guerineau et al., "Effect of deletions in the cauliflower mosaic virus polyadenylation sequence on the choice of the polyadenylation sites in tobacco protoplasts," *Mol. Gen. Genet.* 1991, 262:141-144.
Guilfoyle et al., "How does auxin turn on genes?" *Plant Physiol.*, 1998, 118:341-347.
Hamilton et al., "Stable transfer of intact high molecular weight DNA into plant chromosomes," *Proc. Natl. Acad. Sci., USA*, 1996, 93:9975-9979.
Hart et al., "A 61 bp enhancer element of the tobacco β-1,2-glucanase B gene interacts with one or more regulated nuclear proteins," *Plant Mol Biol.*, 1993, 21:121-131.
Hatton et al., "Two classes of cis sequences contribute to tissue-specific expressio of a PAL2 promoter in transgenic tobacco," *Plant J.*, 1995, 7:859-876.
Hattori et al., "Experimentally determined sequence requirement of ACGT-containing abscisic acid response element," *Plant Cell Physiol*, 2002, 43:136-140.
Heithoff et al., "Bacterial infection as assessed by in vivo gene expression," *Proc Natl Acad Sci USA*, 1997, 94:934-939.
Hensel et al. "Developmental and age-related processes that influence the longevity and senescence of photosynthetic tissues in *Arabidopsis*," *Plant Cell*, 1993, 5:553-64.

(56) References Cited

OTHER PUBLICATIONS

Herrera-Estrella et al., "Chimeric genes as dominant selectable markers in plant cells," *EMBO J.*, 1983, 2(6):987-995.
Higo et al., "Plant cis-acting regulatory DNA elements (PLACE) database: 1999," *Nucleic Acids Research*, 1999, 27(1): 297-300.
Himmelbach et al., "Homeodomain ptorein ATHB6 is a target of the protein phosphate ABI1 and regulates hormone responses in *Arabidopsis*," *EMBO J.*, 2002, 21:3029-3038.
Hirose et al.,"cDNA cloning and tissue specific expression of a gene for sucrose transporter from rice (*Oryza sativa* L.)," *Plant cell Physiol*, 1997, 38:1389-1396.
Horsch et al., "A simple and general method for transferring genes into plants," *Science*, 1985, 227:1229-1231.
Huang et al., "High lysine and high tryptophan transgenic maize resulting from the reduction of both 19- and 22-kD alpha-zeins," *Plant Mol Biol.*, 1990, 14:655-668.
Huang et al., "The *Arabidopsis* ACTII actin gene is strongly expressed in tissues of the emerging inflorescence, pollen, and developing ovules," *Plant Mol Biol*, 1997, 33:125-139.
Huynh et al., "Constructing and Screening cDNA Libraries in λgt10 and λgt11," *DNA Cloning: A practical approach*, vol. 1 (Oxford, IRL Press, 1985), pp. 49-78.
Hwang et al. "An *Arabidopsis thaliana* root-specific kinase homolog is induced by dehydration, ABA, and NaCl," *The Plant Journal*, 1995, 8(1):37-43.
Ishida et al., "High efficiency transformation of maize (*Zea mays* L. mediated by *Agrobacterium tumefaciens*," *Nature Biotechnology*, 1996, 14:745-750.
Ishiguro and Nakamura, "Characterization of a cDNA encoding a novel DNA-binding protein, SPF1, that recognizes SP8 sequences in the 5' upstream regions of genes coding for sporamin and β-amylase from sweet potato," *Mol Gen Genet*, 1994, 244:563-571.
Ishiguro and Nakamura, "The nuclear factor SP8BF binds to the 5'-upstream regions of three different genes coding for major proteins of sweet potato tuberous roots," *Plant Mol Biol.*, 1992, 18:97-108.
Itzhaki et al., An ethylene-responsive enhancer element is involved in the senescence-related expression of the carnation glutathione-S-transferase (GST1) gene, *Proc Natl Acad Sci USA*, 1994, 91:8925-8929.
Iwasaki et al., "Identification of a cis-regulatory region of a gene in *Arabidopsis thaliana* whose induction by dehydration is mediated by abscisic acid and requires protein synthesis," *Mol Gen Genet*, 1995, 247:391-398.
Jaglo-Ottosen et al., "*Arabidopsis* CBF1 overexpression induces COR genes and enhances freezing tolerance," *Science*, 1998, 3:104-106.
Jones et al., "Ethylene-regulated expression of a carnation cysteine proteinase during flower petal senescence," *Plant Mol Biol*, 1995, 28:505-512.
Joshi et al., "Context sequences of translation initiation codon in plants," *Plant Mol Biol.*, 1997, 35:993-1001.
Joshi et al., "An inspection of the domain between putative TATA box and translation start site in 79 plant genes," *Nucleic Acid Res.*, 1987, 15:9627-9639.
Kalaitzis et al. "Cloning of a tomato polygalacturonase expressed in abscission," *Plant Mol. Biol.*, 1995, 28:647-56.
Kaplan et al., "Rapid transcriptome changes induced by cytosolic $Ca^{2+}$ transients reveal ABRE-related sequences as $Ca^{2+}$-responsive cis elements in *Arabidopsis*," *Plant Cell*, 2006, 18:2733-2748.
Kim and Wright, "A comparison of the effects of testicular maturation and aging on the stage-specific expression of CP-2/cathepsin L messenger ribonucleic acid by sertoli cells of the brown norway rat," *Biol Reprod*, 1997, 57:1467-1477.
Kim et al., "A 20 nucleotide upstream element is essential for the nopaline synthase (nos) promoter activity," *Plant Molecular Biology*, 24:105-117.
Kirch et al., "Structural organization, expression and promoter activity of a cold-stress-inducible gene of potato (*Solanum tuberosum* L.)," *Plant Mol Biol.*, 1997, 33:897-909.

Koltonow et al., "Different temporal and spatial gene expression patterns occur during another development," *Plant Cell*, 1990, 2:1201-1224.
Koono et al., "Distribution of hepatocyte growth factor activator inhibitor type 1 (HAI-1) in human tissues: cellular surface localization of HAI-1 in simple columnar epithelium and its modulated expression in injured and regenerative tissues," *J.Histochem Cytochem*, 1999, 47:673-682.
Kosugi and Ohashi, "E2F sites that can interact with E2f proteins cloned from rice are required for meristematic tissue-specific expression of rice and tobacco proliferating cell nuclear antigen promoters," *Plant J.*, 2002, 29:45-59.
Kuster et al., "The sucrose synthase gene is predominantly expressed in the root nodule tissue of Vicia faba," *Mol Plant Microbe Interact*, 1993, 6:507-514.
Larochelle and Suter, "The *Drosophila* homologue of the mammalian map kinase activated protein kinase-s (MAPKAPK-2) lacks a proline rich amino terminus," *Gene*, 1995, 163:209-214.
Lelievre et al., "5'CATGCAT-3' elementa modulate the expression of glycinin genes," *Plant Physiol.*, 1992, 98:387-391.
Lindsey et al., "Tagging genomic sequences that direct transgene expression by activation of a promoter trap in plants," *Transgenic Research*, 1993, 2:33-47.
Liu et al. "Thermal assymmetric interlaced PCR: automatable amplification and sequencing of insert end fragments from P1 and YAC clones for chromosome walking," *Genomics*, 1995, 25:674-681.
Liu et al., "A G-box-binding protein from soybeam binds to the E1 auxin-response element in the soybean GH3 promoter and contains a proline-rich repression domain," *Plant Physiol.*, 1997, 115:397-407.
Liu et al., "Efficient isolation and mapping of *Arabidopsis thaliana* T-DNA insert junctions by thermal asymmetric interlaced PCR," *Plant J.*, 1995, 8(3):457-463.
Liu et al., "Soybean GH3 promoter contains multiple auxin-inducible elements," *Plant Cell*, 1994, 6:645-657.
Mahan et al., "Antibiotic-based selection for bacterial genes that are specifically induced during infection of a host," *Proc Natl Acad Sci.*, 1995, 92:669-673.
Mahan et al., "Selection of bacterial virulence genes that are specifically induced in host tissues," *Science*, 1993, 259:686-688.
Marrs and Walbot "Expression and RNA splicing of the maize glutathione S-transferase Bronze2 gene is regulated by cadmium and other stresses," *Plant Physiol.*, 1997, 113:93-102.
Martinez and Chrispeels, "Genomic analysis of the unfolded protein response in *Arabidopsis* shows its connection to important cellular processes," *Plant Cell*, 2003, 15:561-576.
Martinez-Hernandez et al., "Functional properties and regulatory complexity of a minimal RBCS light-responsive unit activated by phytochrome, cryptochrome, and plastid signals," *Plant Physiol.*, 2002, 128:1223-1233.
Mason and Mullet "Expression of two soybean vegetative storage protein genes during development and in response to water deficit, wounding, and jasmonic acid" *Plant Cell*, 1990, 2:569-579.
May et al., "Generation of transgenic banana (*Musa acuminate*) plants via *Agrobacterium*-mediated transformation" *Bio/Technology*, 1995, 13:486-492.
Miki et al. "Procedures for Introducing Foreign DNA into Plants" *Methods in Plant Molecular Biology & Biotechnology*, 1993, pp. 67-88.
Mogen et al. "Upstream sequences other than AAUAAA are required for efficient messenger RNA 3'-end formation in plants," *Plant Cell*, 1990, 2:1261-1272.
Montgomery et al., "Identification of an ethylene-responsive region in the promoter of a fruit ripening gene," *Proc Natl Acad Scii USA*, 1993, 90:5939-5943.
Morita et al., "Functional dissection of a sugar-repressed alpha-amylase gene (RAmyl A) promoter in rice embryos," *FEBS Lett*, 1998, 423:81-85.
Munroe et al., "Tales of poly(A): a review," *Gene*, 1990, 91:151-158.
Murray et al. "Codon usage in plant genes" *Nucleic Acids Res.*, 1989, 17:477-498.

(56) References Cited

OTHER PUBLICATIONS

Nag et al., "Dual DNA binding property of ABA insensitive 3 like factors targeted to promoters responsive to ABA and auxin," *Plant Mol Biol.*, 2005, 59:821-838.
Nakamura et al., "Photosynthesis nuclear genes generally lack TATA-boxes: a tobacco photosystem I gene response to light through an initiator," *Plant J.*, 2002, 29:1-10.
Nakashima et al., "Transcription regulation of ABI3- and ABA-responsive genes including RD29B and RD29A in seeds, germinating embryos and seedlings of *Arabidopsis*," *Plant Mol Biol*, 2006, 60:51-68.
Namihira et al., "Circadian rhythms and light responsiveness of mammalian clock gene, Clock and BMAL1, transcripts in the rat retina," *Neurosci Lett*, 1999, 271:1-4.
Narusaka et al., "Interaction between two cis-acting elements, ABRE and DRE, in ABA dependent expression of *Arabidopsis* re29A gene in response to dehydration and high-salinity stresses," *Plant J.*, 2003, 34:137-148.
Ogawa et al., "Gibberellin biosynthesis and response during *Arabidopsis* seed germination," *Plant Cell*, 2003, 15:1591-1604.
Oh et al., "Conservation between animals and plants of the cis-acting element involved in the unfolded protein response," *Biochem Biophys Res Commun.*, 2003, 301:225-230.
Ohme-Takagi et al., "Regulation of ethylene-induced transcription of defense genes," *Plant Cell Physiol.*, 2000, 41:1187-1192.
Patzlaff et al., "Characterisation of Pt MYB1, and R2R3-MYB from pine xylem," *Plant Mol Biol.*, 2003, 53:597-608.
Pena-Cortes et al., "Systemic induction of proteinase-inhibitor-II gene expression in potato plants by wounding," *Planta*, 1988, 174:84-89.
Phillips et al., "Cell-tissue culture and In-Vitro Manipulation" *Corn & Corn Improvement*, 1998, p. 345-387.
Prestridge, "Signal Scan: a computer prorgam that scans DNA Sequences for eukaryotic transcriptional elements," *CABIOS*, 1991, 7:203-206.
Proudfoot, "Poly(A) signals," *Cell*, 1991, 64:671-671.
Raju and Maines, "Coordinated expression and mechanism of induction of HSP32 (heme oxygenase-1) mRNA by hyperthermia in rat organs," *Biochim Biophys Acta*, 1994, 1217:273-80.
Ramirez-Parra et al., "A genome-wide identification of E2F-regulated genes in *Arabidopsis*," *Plant J.*, 2003, 33:801-811.
Rawat et al., "Identification of cis-elements in ethylene and circadian regulation of the *Solanum melongena* gene encoding cysteine proteinase," *Plant Mol. Biol.*, 2005, 57:629-643.
Rea et al. "Developmentally and wound-regulated expression of the gene encoding a cell wall copper amine oxidase in chickpea seedlings," *FEBS Letters*, 1998, 437:177-82.
Reddy et al., "Cloning and charterization of a cDNA encoding topoisomerase II in pea and analysis of its expression in relation to cell proliferation," *Plant Mol Biol*, 1999, 41:125-137.
Rivoal et al., "Differential induction of pyruvate decarboxylase subunits and transcripts in anoxic rice seedlings," *Plant Physiol.*, 1997, 114(3):1021-29.
Rohde et al., "ABI3 affects plastid differentiation in dark-grown *Arabidopsis* seedlings," *Plant Cell*, 2000, 12:35-52.
Rubio et al., "A conserved MYB transcription factor involved in phosphate starvation signaling both in vascular plants and in unicellular algae," *Genes Dev.*, 2001, 15:2122-2133.
Rubio-Somoza et al., "Ternary complex formation between HvMYBS3 and other factors involved in transcriptional control in barley seeds," *Plant J.*, 2006, 47:269-281.
Rushmore et al, "The antioxidant responsive element," *J.Biol Chem*, 1991, 266:11632-11639.
Rushton et al., "Synthetic plant promoters containing defined regulatory elements provide novel insights into pathogen-and wound-induced signaling," *Plant Cell*, 2002, 14:749-762.
Sablowski et al., "A flower specific Myb protein activates transcription of phenylpropanoid biosynthetic genes," *EMBO J.*, 1994, 13:128-137.

Salomon et al., "Genetic identification of functions of TR-DNA transcripts in octopine crown galls," *EMBO J.*, 1984, 3:141-146.
Sambrook et al., 1989, "Molecular Cloning, A Laboratory Manual", second edition, Cold Spring Harbor Press, Plainview; NY, 21 pages.
Sanfacon et al., "A dissection of the cauliflower mosaic virus polyadenylation signal," *Genes Dev*, 1991, 5:141-149.
Sato et al., "Ethylene-induced gene expression of osmotin-like protein, a neutral isoform of tobacco PR-5, is mediated by the AGCCGCC eft-sequence," *Plant Cell Physiol*, 1996, 37:249-255.
Saucedo et al., "Regulation of transcriptional activation of mdm2 gene by p53 in response to UV radiation," *Cell Growth Differ*, 1998, 9:119-130.
Sessa et al., "Dark induction and subcellular localization of the pathogenesis-related PRB-1b protein," *Plant Mol Biol.*, 1995, 28:537-547.
Sessa et al., "The Athb-1 and -2 HD-Zip domains homodimerize forming complexes of different DNA binding specificities," *EMBO J.*, 1993, 12:3507-3517.
Shani et al., "Cloning and characterization of elongation specific endo-1,4-β-glucanase (cell) from *Arabidopsis thaliana*," *Plant Mol Biol.* 1997, 34(6):837-842.
Shirsat et al., "Sequences responsible for the tissue specific promoter activity of a pea legumin gene in tobacco," *Mol Gen Genet*, 1989, 215:326-331.
Shizuya et al., "Cloning and stable maintenance of 300-kilobase-pair fragments of human DNA in *Escherichia coli* using an F-factor-based vector," *Proc. Natl. Acad. Sci, USA*, 1992, 89:8794-8797.
Shunmann et al., "Characterization of promoter expression patterns derived from the Pht1 phosphate transporter genes of barley (*Hordeum vulgare* L.)," *J. Exp. Bot.*, 2004, 55:855-865.
Shunmann et al., "Promoter Analysis of the Barley Pht1;1Phosphate Transporter Gene Identified Regions Controlling Phosphate Deprivation," *Plant Physiol.*, 2004, 136:4205-4214.
Simpson et al., "Two different novel cis-acting elements of erd1, a clpA homoologous *Arabidopsis* gene function in induction by dehydration stress and dark-induced senescence," *Plant J*, 2003, 33:259-270.
Skarnes, "Entrapment vectors: a new tool for mammalian genetics," *Biotechnology*, 1990, 8:827-831.
Stalker et al., "Herbicide resistance in transgenic plants expressing a bacterial detoxification gene," *Science*, 1988, 242:419-423.
Sternberg et al., "Bacteriophage P1 cloning system for the isolation, amplification, and recovery of DNA fragments as large as 100 kilobase pairs," *Proc. Natl. Acad. Sci. USA*, 1990, 87(1):103-107.
Stromvik et al. "A novel promoter from soybean that is active in a complex developmental pattern with and without its proximal 650 base pairs," *Plant Mol. Biol.* 1999, 41:217-231.
Sutoh and Yamauchi, "Two cis-acting elements necessary and sufficient for gibberellin-upregulated proteinase expression in rice seeds," *Plant J.*, 2003, 34:635-645.
Suzuki et al., "Quantitative statistical analysis of cis-regulatory sequences in $ABA/VP_1$- and $CBF/DREB_1$-regulated gense of *Arabidopsis*," *Plant Physiol.*, 2005, 139:437-447.
Tamagnone et al., "The AmMYB308 and AmMYB330 transcription factors from antirrhinum regulate phenylpropanoid and lignin biosynthesis in transgenic tobacco," *Plant Cell*, 1998, 10:135-154.
Tang and Perry, "Bing Site Selection for the Plant MADS Domain Protein AGL15," *J. Biol Chem.*, 2003, 278:28154-28156.
Tatematsu et al., "Identification of cis-elements that regulate gene expression during initiation of axillary bud outgrowth in *Arabidopsis*," *Plant Physiol.*, 2005, 138:757-766.
Terzaghi and Cashmore, "Light regulated transcription," *Annu Rev Plant Physiol Plant Mol Biol.*, 1995, 46:445-474.
Tomes et al., "Direct DNA transfer into intact plant cells via microprojectile bombardment" *Plant Cell, Tissue and Organ Culture: Fundamental Methods*, Springer Verlag, Berlin (1995), 19 pages.
Toyofuku et al., "Promoter elements required for sugar-repression of the RAmy3D gene for α-amylase in rice," *FEBS Lett*, 1998, 428:275-280.
Tsai and Coruzzi, "Dark-induced and organ-specific expression of two asparagine synthetase genes in *Pisum sativum*," *EMBO J.*, 1990, 9:323-32.

(56) References Cited

OTHER PUBLICATIONS

Ulmasov et al., "Composite structure of auxin response elements," *Plant Cell*, 1995, 7:1611-1623.

Vandepoele et al., "Genome-wide identification of potential plant E2F target genes," *Plant Physiol.*, 2005, 139:316-328.

Vaucheret et al., "Transgene-induced gene silencing in plants," *The Plant Journal*, 1998, 16(6):651-669.

Vergunst et al., "Cre/lox-mediated site-specific integration of *Agrobacterium* T-DNA in *Arabidopsis thaliana* by transient expression of cre," *Plant Mol. Biol.*, 1998, 38:393-406.

von Gromoff et al., "Identification of a plastid response element that acts as an enhancer within the *Chlamydomonas* HSP70A promoter," *Nucleic Acids Res.*, 2006, 34:4767-4779.

Walden et al., "The Use of Gene Vectors in Plant Molecular Biology," *Mol Cell Biol*, 1990, 1:175-194.

Walter et al., "Bean ribonuclease-like pathogenesis-related protein genes (Yprl 0) display complex patterns of developmental, dark-induced and exogenous-stimulus-dependent expression," *Eur J. Biochem*, 1996, 239:281-293.

Wang et al., "A Myb-related transcription factor is involved in the phytochrome regulation of an *Arabidopsis* Lhcb gene," *Plant Cell*, 1997, 9:491-507.

Wang et al., "Large-scale isolation of candidate virulence genes of *Pseudomonas aeruginosa* by in vivo selection," *Proc Natl Acad Sci, USA*, 1996, 93:10434-10439.

Wingender et al., "Differential regulation of soybean chalcone synthase genes in plant defence, symbiosis and upon environmental stimuli," *Mol Gen Genet*, 1989, 218:315-322.

Xu et al., "Characterization of a rice gene family encoding root-specific proteins," *Plant Mol. Biol.*, 1995, 27:237-248.

Yamada et al. "A family of transcripts encoding water channel proteins: tissue-specific expression in the common ice plant," *Plant Cell*, 1995, 7:1129-1142.

Yamamoto et al., "Characterization of cis-acting sequences regulating root-specific gene expression in tobacco," *The Plant Cell*, 1991, 3:371-382.

Yi et al., "Auxin and brassinosteroid differentially regulate the expression of three members of the 1-aminocyclopropane-1-carboxylate synthase gene family in mung bean (*Vigna radiata* L.)," *Plant Mol Biol*, 1999, 41:443-454.

Zhang et al., "The ethylene-, jasmonate-, abscisic acid- and NaCl-response tomato transcription factor JERF1 modulates expression of GCC box-containing genes and salt tolerance in tobacco," *Planta*, 2004, 220:262-270.

Zhu et al., "Rice TATA binding protein interacts functionally with transcription factor IIB and the RF2a bZIP transcriptional activator in an enhanced plant in vitro transcription system," *Plant Cell*, 2002, 14:795-803.

Zoe et al., "Thermal asymmetric interlaced PCT amplification of YAC insert end fragments for chromosome walking in Plasmodium falciparum and other A/T-rich genomes," *BioTechniques*, 1999, 27(2):240-248.

Cho et al., "Regulation of Root Hair Initiation and Expansin Gene Expression in *Arabidopsis*," *The Plant Cell* 14:3237-3253, 2002.

Piechulla et al., "Identification of tomato Lhc promoter regions necessary for circadian expression," *Plant Molecular Biology* 38:655-662, 1998.

Welsch et al., "Structural and functional characterization of the phytoene synthase promoter from *Arabidopsis thaliana*," *Planta* 216:523-534, 2003.

Childs et al., "Genetic Regulation of Development in *Sorghum bicolor*," *Plant Physiol.* 99:765-770, 1992.

\* cited by examiner

*Analysis of Promoter PD3525 activity*

| Promoter Expression Report For PD3525 (SEQ ID NO:1) | |
|---|---|
| Promoter Tested In: *Oryza sativa* | |
| Construct: PD3525 | |
| SR/OS Line: OS00669 | |
| Promoter candidate I.D: 60304231 | |
| Events expressing: 01 | |
| Spatial expression summary: <br> T0 Seedling <br><br> TILLER <br> ☑ ALL TISSUES <br> MAIN CULM <br> ☐ BUNDLE SHEATH ☐ ENDODERMIS ☐ EPIDERMIS ☐ INTERNODE ☐ LIGULE ☐ NODE <br> ☑ ALL TISSUES ☐ PERICYCLE ☐ PHLOEM ☐ SCLERENCHYMA LAYER ☐ VASCULATURE ☐ XYLEM <br> ROOT <br> ☐ CORTEX ☐ EPIDERMIS ☑ ALL TISSUES ☐ ROOT CAP ☐ VASCULAR <br> LEAF <br> ☐ EPIDERMIS ☐ LEAF BLADE ☐ LEAF SHEATH ☐ MARGIN ☐ MESOPHYLL ☑ ALL TISSUES <br> ☐ PETIOLE ☐ PRIMORDIA ☐ STIPULE ☐ STOMATA ☐ TRICHOME ☐ VASCULATURE <br> MERISTEM <br> ☐ FLORAL MERISTEM ☑ ALL TISSUES ☐ SHOOT APICAL MERISTEM ☐ VEGETATIVE MERISTEM <br><br> T0 Mature | |
| Observed expression pattern: <br> T0 Seedling: Expression observed strongly throughout all tissues of the seedling. <br> T0 Mature: | |
| Gene: Sorghum annot ID: 8660387 | |
| cDNA I.D: 71469037 | |
| GenBank: S-adenosylmethionine synthetase by homology to At3g17390 | |
| Source Promoter Organism: *Sorghum bicolor* | |
| Vector: CRS830_Binary_DF_EGFP | |
| Marker Type: EGFP | |
| Generation Screened: T0 Seedling | |
| Table 1. T0 Seedling Expression Organs/Tissues screened | |

Figure 2

| Events Screened: n = 1  Events Expressing: n = 1 (01) |
|---|
| Organs |
| TILLER |
| ☑ ALL TISSUES |
| MAIN CULM |
| ☐ BUNDLE SHEATH    ☐ ENDODERMIS    ☐ EPIDERMIS    ☐ INTERNODE    ☐ LIGULE    ☐ NODE |
| ☑ ALL TISSUES    ☐ PERICYCLE    ☐ PHLOEM    ☐ SCLERENCHYMA LAYER    ☐ VASCULATURE    ☐ XYLEM |
| ROOT |
| ☐ CORTEX    ☐ EPIDERMIS    ☑ ALL TISSUES    ☐ ROOT CAP    ☐ VASCULAR |
| LEAF |
| ☐ EPIDERMIS    ☐ LEAF BLADE    ☐ LEAF SHEATH    ☐ MARGIN    ☐ MESOPHYLL    ☑ ALL TISSUES |
| ☐ PETIOLE    ☐ PRIMORDIA    ☐ STIPULE    ☐ STOMATA    ☐ TRICHOME    ☐ VASCULATURE |
| MERISTEM |
| ☐ FLORAL MERISTEM    ☑ ALL TISSUES    ☐ SHOOT APICAL MERISTEM    ☐ VEGETATIVE MERISTEM |
| Table 2. T0 Mature Plant Expression       Organs/Tissues screened |
| Events Screened: n =          Events Expressing: n = |
| Organs |
| |
| Table 3. Promoter utility |
| Trait Area: Salt tolerance, Water Use Efficiency, Nutrient Use Efficiency, Nutrient Utilization, Increased Biomass, BioConfinement |
| Sub-trait Area: Salt tolerance, Drought tolerance, Phosphate and Nitrate Use Efficiency, Phosphate and Nitrate Utilization, Plant Architecture, Enhanced Photosynthesis, Cell-wall composition and conversion, Male sterility, Female sterility, Total sterility |
| Utility: Among other uses, this promoter sequence could be useful to improve: the biomass of the plants under normal and stressful conditions through the overexpression of transgenes that improve water use, nutrient use, alter composition, alter plant architecture, disrupt reproductive biology, and improve the carbon-nitrogen balance. |
| Notes: |

Figure 2 (continued)

Analysis of Promoter PD3559 activity

| Promoter Expression Report For PD3559 (SEQ ID NO:2) | |
|---|---|
| Promoter Tested In: *Oryza sativa* | |
| Construct: PD3559 | |
| SR/OS Line: OS00681 | |
| Promoter candidate I.D: 72581236 | |
| Events expressing: 01, 03, 04, 10, 11 | |
| Spatial expression summary:<br>T0 Seedling<br><br>TILLER<br>☑ NOT-SPECIFIC<br>MAIN CULM<br>☐ BUNDLE SHEATH ☐ ENDODERMIS ☐ EPIDERMIS ☐ INTERNODE ☐ LIGULE ☐ NODE<br>☑ NOT-SPECIFIC ☐ PERICYCLE ☐ PHLOEM ☐ SCLERENCHYMA LAYER ☐ VASCULATURE ☐ XYLEM<br>ROOT<br>☐ CORTEX ☐ EPIDERMIS ☑ NOT-SPECIFIC ☐ ROOT CAP ☐ VASCULAR<br>LEAF<br>☐ EPIDERMIS ☐ LEAF BLADE ☐ LEAF SHEATH ☐ MARGIN ☐ MESOPHYLL ☑ NOT-SPECIFIC<br>☐ PETIOLE ☐ PRIMORDIA ☐ STIPULE ☐ STOMATA ☐ TRICHOME ☐ VASCULATURE<br>MERISTEM<br>☐ FLORAL MERISTEM ☑ NOT-SPECIFIC ☐ SHOOT APICAL MERISTEM ☐ VEGETATIVE MERISTEM<br><br>T0 Mature | |
| Observed expression pattern:<br>T0 Seedling: Expression is observed throughout the leaf and stem of the plant. However, strongest expression appears to be concentrated in the vascular bundles of the stem.<br>T0 Mature expression: | |
| Gene: Sorghum annot ID: 8644338 | |
| cDNA I.D: 71513981 | |
| GenBank: pfam: Photosystem I reaction center subunit psaK | |
| Source Promoter Organism: *Sorghum bicolor* | |
| Vector: CRS830 Binary DF EGFP | |
| Marker Type: EGFP | |
| Generation Screened: T0 Seedling | |
| Table 1. T0 Seedling Expression Organs/Tissues screened | |
| Events Screened: n = 11  Events Expressing: n = 5 (01, 03, 04, 10, 11) | |
| Organs | |

Figure 2 (continued)

| | |
|---|---|
| Table 2. T0 Mature Plant Expression | Organs/Tissues screened |
| Events Screened: n = | Events Expressing: n = |
| Organs | |
| Table 3. Promoter utility | |
| Trait Area: Salt tolerance, Water Use Efficiency, Nutrient Use Efficiency, Nutrient Utilization, Increased Biomass | |
| Sub-trait Area: Salt tolerance, Drought tolerance, Phosphate and Nitrate Use Efficiency, Phosphate and Nitrate Utilization, Plant Architecture, Enhanced Photosynthesis, Cell-wall composition and conversion | |
| Utility: Among other uses, this promoter sequence could be useful to improve: the biomass of the plants under normal and stressful conditions through the overexpression of transgenes that improve water use, nutrient use, alter composition, alter plant architecture, and improve the carbon-nitrogen balance. | |

Figure 2 (continued)

Analysis of Promoter PD3560 activity

| Promoter Expression Report For PD3560 (SEQ ID NO:3) | |
|---|---|
| Promoter Tested In: *Oryza sativa* | |
| Construct: PD3560 | |
| SR/OS Line: OS00695 | |
| Promoter candidate I.D: 66557367 | |
| Events expressing: 01-02-03-04-05-06-07-09-10-11-12-13-14 | |
| Spatial expression summary: <br> T0 Seedling <br><br> TILLER <br> ☑ ALL TISSUES <br> MAIN CULM <br> ☐ BUNDLE SHEATH  ☐ ENDODERMIS  ☐ EPIDERMIS  ☐ INTERNODE  ☐ LIGULE  ☐ NODE <br> ☑ ALL TISSUES  ☐ PERICYCLE  ☐ PHLOEM  ☐ SCLERENCHYMA LAYER  ☐ VASCULATURE  ☐ XYLEM <br> ROOT <br> ☐ CORTEX  ☐ EPIDERMIS  ☑ NOT-SPECIFIC  ☐ ROOT CAP  ☐ VASCULAR <br> LEAF <br> ☐ EPIDERMIS  ☐ LEAF BLADE  ☐ LEAF SHEATH  ☐ MARGIN  ☐ MESOPHYLL  ☑ ALL TISSUES <br> ☐ PETIOLE  ☐ PRIMORDIA  ☐ STIPULE  ☐ STOMATA  ☐ TRICHOME  ☐ VASCULATURE <br> MERISTEM <br> ☐ FLORAL MERISTEM  ☑ ALL TISSUES  ☐ SHOOT APICAL MERISTEM  ☐ VEGETATIVE MERISTEM <br><br> T0 Mature | |
| Observed expression pattern: <br> T0 Seedling: Expression observed broadly throughout the plant. Strongest expression is seen in above ground tissues and weakest in root. <br> T0 Mature: | |
| Gene: Sorghum annot ID: 8654813 | |
| cDNA I.D: 71484775 | |
| GenBank: PFAM       PSI_PSAK; Herpes_gp2; Abhydrolase_1 | |
| Source Promoter Organism:     *Sorghum bicolor* | |
| Vector: CRS830_Binary_DF_EGFP | |
| Marker Type: EGFP | |
| Generation Screened:    T0 Seedling | |
| Table 1. T0 Seedling Expression    Organs/Tissues screened | |
| Events Screened: n = 15  Events Expressing: n = 13  (01-07, 09-14) | |
| Organs | |

Figure 2 (continued)

TILLER
- ☑ ALL TISSUES

MAIN CULM
- ☐ BUNDLE SHEATH
- ☐ ENDODERMIS
- ☐ EPIDERMIS
- ☐ INTERNODE
- ☐ LIGULE
- ☐ NODE
- ☑ ALL TISSUES
- ☐ PERICYCLE
- ☐ PHLOEM
- ☐ SCLERENCHYMA LAYER
- ☐ VASCULATURE
- ☐ XYLEM

ROOT
- ☐ CORTEX
- ☐ EPIDERMIS
- ☑ NOT-SPECIFIC
- ☐ ROOT CAP
- ☐ VASCULAR

LEAF
- ☐ EPIDERMIS
- ☐ LEAF BLADE
- ☐ LEAF SHEATH
- ☐ MARGIN
- ☐ MESOPHYLL
- ☑ ALL TISSUES
- ☐ PETIOLE
- ☐ PRIMORDIA
- ☐ STIPULE
- ☐ STOMATA
- ☐ TRICHOME
- ☐ VASCULATURE

MERISTEM
- ☐ FLORAL MERISTEM
- ☑ ALL TISSUES
- ☐ SHOOT APICAL MERISTEM
- ☐ VEGETATIVE MERISTEM

| Table 2. T0 Mature Plant Expression | Organs/Tissues screened |
|---|---|
| Events Screened: n = | Events Expressing: n = |
| Organs | |

| Table 3. Promoter utility |
|---|
| Trait Area: Salt tolerance, Water Use Efficiency, Nutrient Use Efficiency, Nutrient Utilization, Increased Biomass, BioConfinement |
| Sub-trait Area: Salt tolerance, Drought tolerance, Phosphate and Nitrate Use Efficiency, Phosphate and Nitrate Utilization, Plant Architecture, Enhanced Photosynthesis, Cell-wall composition and conversion, Male sterility, Female sterility, Total sterility |
| Utility: Among other uses, this promoter sequence could be useful to improve: the biomass of the plants under normal and stressful conditions through the overexpression of transgenes that improve water use, nutrient use, alter composition, alter plant architecture, disrupt reproductive biology, and improve the carbon-nitrogen balance. |

Figure 2 (continued)

Analysis of Promoter PD3561 activity

| Promoter Expression Report For PD3561 (SEQ ID NO:4) | |
|---|---|
| Promoter Tested In: *Oryza sativa* | |
| Construct: PD3561 | |
| SR/OS Line: OS00683 | |
| Promoter candidate I.D: 66234711 | |
| Events expressing: 01-03, 06, 07 | |
| Spatial expression summary:<br>T0 Seedling<br><br>ROOT<br><br>☑ CORTEX   ☑ EPIDERMIS   ☐ ROOT CAP   ☑ VASCULAR<br><br>T0 Mature | |
| Observed expression pattern:<br>T0 Seedling: Expression observed strongly throughout the root with the exception of the root cap.<br>T0 Mature: | |
| Gene: Sorghum annot ID: 8702241 | |
| cDNA I.D: 71499032 | |
| GenBank: similar to 14 kDa polypeptide [Catharanthus roseus] GI:407410; contains Pfam protease inhibitor/seed storage/LTP family domain PF00234; go_function: lipid binding [goid 0008289]; go_process: lipid transport [goid 0006869]<br>protein_id    NP_567391.1<br>PFAM  Tryp_alpha_amyl; | |
| Source Promoter Organism: *Sorghum bicolor* | |
| Vector: CRS830_Binary_DF_EGFP | |
| Marker Type: EGFP | |
| Generation Screened: T0 Seedling | |
| Table 1. T0 Seedling Expression    Organs/Tissues screened | |
| Events Screened: n = 7  Events Expressing: n = 5  (01-03, 06, 07) | |
| Organs<br><br>☑ CORTEX   ☑ EPIDERMIS   ☐ ROOT CAP   ☑ VASCULAR | |
| Table 2. T0 Mature Plant Expression    Organs/Tissues screened | |
| Events Screened: n =      Events Expressing: n = | |
| Organs | |
| Table 3. Promoter utility | |
| Trait Area: Salt tolerance, Water Use Efficiency, Nutrient Use Efficiency, Nutrient Utilization | |
| Sub-trait Area: Salt tolerance, Drought tolerance, Phosphate and Nitrate Use Efficiency, Phosphate and Nitrate Utilization | |
| Utility: Among other uses, this promoter sequence could be useful to improve: the biomass of the plants under normal and stressful conditions through the overexpression of transgenes that improve the uptake and transport of | |

Figure 2 (continued)

| water and nutrients |
| Notes: |

Figure 2 (continued)

Analysis of Promoter PD3562 activity

| Promoter Expression Report For PD3562 (SEQ ID NO:5) | |
|---|---|
| Promoter Tested In: *Oryza sativa* | |
| Construct: PD3562 | |
| SR/OS Line: OS00684 | |
| Promoter candidate I.D: 72581080 | |
| Events expressing: 02-06-09-10 | |
| Spatial expression summary: <br> T0 Seedling <br><br> MAIN CULM <br> ☐ BUNDLE SHEATH  ☑ ENDODERMIS  ☑ EPIDERMIS  ☐ INTERNODE  ☐ LIGULE  ☐ NODE <br> ☐ ALL TISSUES  ☐ PERICYCLE  ☐ PHLOEM  ☐ SCLERENCHYMA LAYER  ☐ VASCULATURE  ☐ XYLEM <br><br> LEAF <br> ☑ EPIDERMIS  ☐ LEAF BLADE  ☐ LEAF SHEATH  ☐ MARGIN  ☑ MESOPHYLL  ☐ ALL TISSUES <br> ☐ PETIOLE  ☐ PRIMORDIA  ☐ STIPULE  ☐ STOMATA  ☐ VASCULATURE <br><br> T0 Mature | |
| Observed expression pattern: <br> T0 Seedling: Expression observed in above ground tissues only, including the tiller, leaf, and main culm. The expression appears restricted to green tissues. <br> T0 Mature: | |
| Gene: Sorghum annot ID: 8716063 | |
| cDNA I.D: 71571625 | |
| GenBank: PFAM      Epimerase; Herpes_gp2; Herpes_BLLF1; | |
| Source Promoter Organism:      *Sorghum bicolor* | |
| Vector: CRS830_Binary_DF_EGFP | |
| Marker Type: EGFP | |
| Generation Screened:   T0 Seedling | |
| Table 1. T0 Seedling Expression   Organs/Tissues screened | |
| Events Screened: n = 10  Events Expressing: n = 4  (02, 06, 09, 10) | |
| Organs <br><br> T0 Seedling <br><br> MAIN CULM <br> ☐ BUNDLE  ☑   ☑   ☐ INTERNODE  ☐ LIGULE  ☐ NODE | |

Figure 2 (continued)

|  |  |  |  |  |  |
|---|---|---|---|---|---|
| SHEATH | ENDODERMIS | EPIDERMIS |  |  |  |
| ☐ ALL TISSUES | ☐ PERICYCLE | ☐ PHLOEM | ☐ SCLERENCHYMA LAYER | ☐ VASCULATURE | ☐ XYLEM |
| LEAF |  |  |  |  |  |
| ☑ EPIDERMIS | ☐ LEAF BLADE | ☐ LEAF SHEATH | ☐ MARGIN | ☑ MESOPHYLL | ☐ ALL TISSUES |
| ☐ PETIOLE | ☐ PRIMORDIA | ☐ STIPULE | ☐ STOMATA | ☐ VASCULATURE |  |

| Table 2. T0 Mature Plant Expression | Organs/Tissues screened |
|---|---|
| Events Screened: n = | Events Expressing: n = |
| Organs | |

| Table 3. Promoter utility |
|---|
| Trait Area: Increased Biomass, Altered Composition |
| Sub-trait Area: Plant Architecture, Enhanced Photosynthesis, Cell-wall composition and conversion |
| Utility: Among other uses, this promoter sequence could be useful to improve: the biomass of the plants under normal and stressful conditions through the overexpression of transgenes that alter composition, alter plant architecture, and improve the carbon-nitrogen balance. |

Figure 2 (continued)

*Analysis of Promoter PD3564 activity*

| Promoter Expression Report for PD3564 (SEQ ID NO:6) | |
|---|---|
| Organism Evaluated: *Oryza sativa* | |
| Construct: PD3564 | |
| SR/OS Line: OS00686 | |
| Promoter candidate I.D: 72581280 | |
| Events expressing: 01-03, 07, 10-11, 13 | |

Spatial expression summary:

T0 Seedling
Events Screened: n = 13      Events Expressing: n = 7 (01-03, 07, 10-11, 13)
MERISTEM

FLORAL MERISTEM    NOT-SPECIFIC    SHOOT APICAL MERISTEM    VEGETATIVE MERISTEM

LEAF

EPIDERMIS    FIBER CELLS    FLAG LEAF    GUARD CELL    LEAF BLADE    LEAF SHEATH

MARGIN    MESOPHYLL    NOT-SPECIFIC    PETIOLE    PRIMORDIA    STIPULE

STOMATA    TRICHOME    VASCULATURE

TILLER

BUNDLE SHEATH    ENDODERMIS    EPIDERMIS    MESOPHYLL    NOT-SPECIFIC    PHLOEM

SCLERENCHYMA LAYER    VASCULATURE    XYLEM

MAIN CULM

BUNDLE SHEATH    ENDODERMIS    EPIDERMIS    INTERNODE    LIGULE    NODE

NOT-SPECIFIC    PERICYCLE    PHLOEM    SCLERENCHYMA LAYER    VASCULATURE    XYLEM

T0 Mature
Events Screened: n = 5      Events Expressing: n = 5 (01-03, 07, 10)
MERISTEM

FLORAL MERISTEM    NOT-SPECIFIC    SHOOT APICAL MERISTEM    VEGETATIVE MERISTEM

LEAF

EPIDERMIS    FIBER CELLS    FLAG LEAF    GUARD CELL    LEAF BLADE    LEAF SHEATH

MARGIN    MESOPHYLL    NOT-SPECIFIC    PETIOLE    PRIMORDIA    STIPULE

Figure 2 (continued)

☑ STOMATA ☐ TRICHOME ☑ VASCULATURE

SPIKELET

☐ ALEURONE LAYER ☑ ANTHER ☑ CARPEL ☐ EMBRYO ☐ ENDOSPERM ☑ FILAMENT
☐ LEMMA ☐ NOT-SPECIFIC ☐ OVULE ☐ PALEA ☑ PEDICEL ☐ POLLEN
☐ SEED ☐ STIGMA

PANICLE

☐ NOT-SPECIFIC ☑ OVARY ☑ PEDUNCLE ☐ PRIMARY BRANCH ☐ RACHILLA ☐ RACHIS
☑ SPIKELET

MAIN CULM

☐ BUNDLE SHEATH ☑ ENDODERMIS ☑ EPIDERMIS ☐ INTERNODE ☐ LIGULE ☑ NODE
☐ NOT-SPECIFIC ☐ PERICYCLE ☑ PHLOEM ☑ SCLERENCHYMA LAYER ☑ VASCULATURE ☑ XYLEM

| Observed expression pattern: |
|---|
| T0 Seedling: GFP expression was primarily detected in the emerging shoot. |
| T0 Mature expression: Vegetatively, expression was primarily observed in the epidermal layers of the internodal space, consistent with a role in meristematic function. Significant expression was also detected in the anthers in the reproductive organs. No expression was detected in the roots. |
| Selection Criteria: Based upon: 1) # publicly available EST clones mapped into sorghum genome and 2) # clones in SWG EST clusters |
| Gene: Putative Tryp_alpha_amyl gene with proposed function in lipid transport |
| cDNA I.D: 71472091 |
| GenBank: Tryp_alpha_amyl; |
| Source Promoter Organism: *Sorghum bicolor* |
| Vector: CRS830 Binary DF EGFP |
| Marker Type: EGFP |
| Generation Screened: T0 Seedling and T0 Mature |

| Promoter utility |
|---|
| Trait Area: Biomass Enhancement, Sterility |
| Sub-trait Area: Plant Architecture, Plant Growth, Male Sterility |
| Utility: Among other uses, this promoter sequence could be useful to improve: the growth and development of meristematic tissues at the nodes to improve plant architecture and/or increase biomass, and to engineer male sterility by affecting the growth and/or development of the anthers. |

Figure 2 (continued)

*Analysis for Promoter PD3565 activity*

| Promoter Expression Report for PD3565 (SEQ ID NO:7) | |
|---|---|
| Organism Evaluated: *Oryza sativa* | |
| Construct: PD3565 | |
| SR/OS Line: OS00687 | |
| Promoter candidate I.D: 66234721 | |
| Events expressing: 02, 05-07, 09, 12-13 | |
| Spatial expression summary:<br><br>T0 Seedling<br>Events Screened: n = 14      Events Expressing: n = 7 (02, 05-07, 09, 12-13)<br>ROOT<br><br>☐ CORTEX   ☐ ENDODERMIS   ☐ EPIDERMIS   ☐ EXODERMIS   ☑ LATERAL ROOT   ☑ NOT-SPECIFIC<br><br>☐ ROOT CAP   ☐ VASCULAR<br>T0 Mature<br>Events Screened: n = 6      Events Expressing: n = 6 (02, 05-07, 09, 12)<br>LEAF<br><br>☐ EPIDERMIS   ☑ FIBER CELLS   ☐ FLAG LEAF   ☐ GUARD CELL   ☐ LEAF BLADE   ☐ LEAF SHEATH<br><br>☐ MARGIN   ☑ MESOPHYLL   ☐ NOT-SPECIFIC   ☐ PETIOLE   ☐ PRIMORDIA   ☐ STIPULE<br><br>☐ STOMATA   ☐ TRICHOME   ☐ VASCULATURE<br>ROOT<br><br>☐ CORTEX   ☑ ENDODERMIS   ☑ EPIDERMIS   ☑ EXODERMIS   ☐ LATERAL ROOT   ☑ NOT-SPECIFIC<br><br>☐ ROOT CAP   ☑ VASCULAR | |
| Observed expression pattern:<br>T0 Seedling: GFP expression was only detected in lateral roots.<br>T0 Mature expression: Expression is strongest in roots. Lateral, fibrous roots have stronger expression than older, more mature roots. | |
| Selection Criteria: Putative ortholog of at1g77330. | |
| Gene: Putative 1-aminocyclopropane-1-carboxylate oxidase | |
| cDNA I.D: 71472091 | |
| GenBank: | |
| Source Promoter Organism: *Sorghum bicolor* | |
| Vector: CRS830 Binary DF EGFP | |
| Marker Type: EGFP | |
| Generation Screened: T0 Seedling and T0 Mature | |

Figure 2 (continued)

| |
|---|
| Promoter utility |
| Trait Area: Water Use Efficiency, Nutrient Use Efficiency |
| Sub-trait Area: Enhanced water uptake, Enhanced nitrogen uptake |
| Utility: Among other uses, this promoter sequence could be useful to improve: the growth and architecture of roots, the strength of the root system, and the transport of water and nutrients into the above ground portion of the plant for enhanced biomass. |

Figure 2 (continued)

*Analysis of Promoter PD3567 activity*

| Promoter Expression Report for PD3567 (SEQ ID NO:13) | |
|---|---|
| Organism Evaluated: *Oryza sativa* | |
| Construct: PD3567 | |
| SR/OS Line: OS00814 | |
| Promoter candidate I.D: 71811444 | |
| Events expressing: 2-7 | |
| Spatial expression summary:<br><br>T0 Seedling<br>Events Screened: n = 10  Events Expressing: n = 4 (01-02-08-09)<br>ROOT<br><br>☐ CORTEX  ☐ ENDODERMIS  ☐ EPIDERMIS  ☐ EXODERMIS  ☐ LATERAL ROOT  ☑ NOT-SPECIFIC<br><br>☐ ROOT CAP  ☐ VASCULAR<br><br>T0 Mature<br>Events Screened: n = 4  Events Expressing: n = 4 (01-02-08-09)<br>ROOT<br><br>☐ CORTEX  ☐ ENDODERMIS  ☑ EPIDERMIS  ☐ EXODERMIS  ☐ LATERAL ROOT  ☐ NOT-SPECIFIC<br><br>☐ ROOT CAP  ☑ VASCULAR | |
| Observed expression pattern:<br>T0 Seedling: Expression observed in the roots.<br>T0 Mature expression: Expression observed specifically in the epidermis and vasculature of the roots | |
| Selection Criteria: Ortholog of At4g13180 | |
| Gene: Sorghum annot ID: 6004190 | |
| cDNA I.D: 71396005 | |
| GenBank: pfam: similar to short-chain type dehydrogenase/reductase | |
| Source Promoter Organism:  *Sorghum bicolor* | |
| Vector: CRS830 Binary DF EGFP | |
| Marker Type: EGFP | |
| Generation Screened: T0 Seedling and T0 Mature | |

| Promoter utility |
|---|
| Trait Area: Water Use Efficiency, Nutrient Use Efficiency |
| Sub-trait Area: Enhanced water uptake, Enhanced nitrogen uptake |
| Utility: Among other uses, this promoter sequence could be useful to improve: uptake and/or transport of water and/or nutrients into and through the root system. |

Figure 2 (continued)

*Analysis of Promoter PD3573 activity*

| Promoter Expression Report For PD3573 (SEQ ID NO:8) | |
|---|---|
| Organism Evaluated: *Oryza sativa* | |
| Construct: PD3573 | |
| SR/OS Line: OS00675 | |
| Promoter candidate I.D: 58715949 | |
| Events expressing: 01-04 | |
| Spatial expression summary:<br><br>T0 Seedling<br><br>ROOT<br><br>☐ CORTEX  ☑ EPIDERMIS  ☑ EXODERMIS  ☐ ROOT CAP  ☐ VASCULAR<br><br>T0 Mature | |
| Observed expression pattern:<br>T0 Seedling: GFP expression is detected specifically in the exodermis and epidermis of secondary roots.<br>T0 Mature expression: | |
| Gene: Sorghum annot id 8681201 | |
| cDNA I.D: 71518006 | |
| GenBank: PFAM          peroxidase | |
| Source Promoter Organism: *Sorghum bicolor* | |
| Vector: CRS830 Binary DF EGFP | |
| Marker Type: EGFP | |
| Generation Screened: T0 Seedling | |

| Table 1. T0 Seedling Expression    Organs/Tissues screened |
|---|
| Events Screened: n = 4   Events Expressing: n = 4  (01-04) |
| Organs<br>ROOT<br><br>☐ CORTEX  ☑ EPIDERMIS  ☑ EXODERMIS  ☐ ROOT CAP  ☐ VASCULAR |

| Table 2. T0 Mature Plant Expression    Organs/Tissues screened |
|---|
| Events Screened: n =     Events Expressing: n = |
| Organs |

| Table 3. Promoter utility |
|---|
| Trait Area: Salt tolerance, Water Use Efficiency, Nutrient Use Efficiency, Nutrient Utilization |
| Sub-trait Area: Salt tolerance, Drought tolerance, Phosphate and Nitrate Use Efficiency, Phosphate and Nitrate Utilization |
| Utility: Among other uses, this promoter sequence could be useful to improve: the biomass of the plants under |

Figure 2 (continued)

normal and stressful conditions through the overexpression of transgenes that improve water and nutrient uptake and use efficiency.

Figure 2 (continued)

Analysis of Promoter PD3574 activity

| Promoter Expression Report For PD3574 (SEQ ID NO:9) | |
|---|---|
| Promoter Tested In: *Oryza sativa* | |
| Construct: PD3574 | |
| SR/OS Line: OS00677 | |
| Promoter candidate I.D: 57384231 | |
| Events expressing: 01-03-05-07-11-12-13 | |
| Spatial expression summary: <br> T0 Seedling <br> TILLER <br> ☑ NOT-SPECIFIC <br> MAIN CULM <br> ☐ BUNDLE SHEATH  ☐ ENDODERMIS  ☐ EPIDERMIS  ☐ INTERNODE  ☐ LIGULE  ☐ NODE <br> ☑ NOT-SPECIFIC  ☐ PERICYCLE  ☐ PHLOEM  ☐ SCLERENCHYMA LAYER  ☐ VASCULATURE  ☐ XYLEM <br> ROOT <br> ☐ CORTEX  ☐ EPIDERMIS  ☑ NOT-SPECIFIC  ☐ ROOT CAP  ☐ VASCULAR <br> LEAF <br> ☐ EPIDERMIS  ☐ LEAF BLADE  ☐ LEAF SHEATH  ☐ MARGIN  ☐ MESOPHYLL  ☑ NOT-SPECIFIC <br> ☐ PETIOLE  ☐ PRIMORDIA  ☐ STIPULE  ☐ STOMATA  ☐ TRICHOME  ☐ VASCULATURE <br> MERISTEM <br> ☐ FLORAL MERISTEM  ☑ NOT-SPECIFIC  ☐ SHOOT APICAL MERISTEM  ☐ VEGETATIVE MERISTEM <br><br> T0 Mature | |
| Observed expression pattern: <br> T0 Seedling: Expression observed throughout the plant, but not strongly. Expression in roots appears confined to secondary roots. <br> T0 Mature expression: | |
| Gene: Sorghum annot ID: 8656219 | |
| cDNA I.D: 71490667 | |
| GenBank: pfam: translation elongation factor | |
| Source Promoter Organism: *Sorghum bicolor* | |
| Vector: CRS830_Binary_DF_EGFP | |
| Marker Type: EGFP | |
| Generation Screened: T0 Seedling | |
| Table 1. T0 Seedling Expression  Organs/Tissues screened | |
| Events Screened: n = 13  Events Expressing: n = 7 (01,03,05,07,11-13) | |
| Organs <br> TILLER | |

Figure 2 (continued)

☑ NOT-SPECIFIC
MAIN CULM

☐ BUNDLE SHEATH ☐ ENDODERMIS ☐ EPIDERMIS ☐ INTERNODE ☐ LIGULE ☐ NODE

☑ NOT-SPECIFIC ☐ PERICYCLE ☐ PHLOEM ☐ SCLERENCHYMA LAYER ☐ VASCULATURE ☐ XYLEM

ROOT

☐ CORTEX ☐ EPIDERMIS ☑ NOT-SPECIFIC ☐ ROOT CAP ☐ VASCULAR

LEAF

☐ EPIDERMIS ☐ LEAF BLADE ☐ LEAF SHEATH ☐ MARGIN ☐ MESOPHYLL ☑ NOT-SPECIFIC

☐ PETIOLE ☐ PRIMORDIA ☐ STIPULE ☐ STOMATA ☐ TRICHOME ☐ VASCULATURE

MERISTEM

☐ FLORAL MERISTEM ☑ NOT-SPECIFIC ☐ SHOOT APICAL MERISTEM ☐ VEGETATIVE MERISTEM

| Table 2. T0 Mature Plant Expression | Organs/Tissues screened |
|---|---|
| Events Screened: n = | Events Expressing: n = |
| Organs | |
| Table 3. Promoter utility | |
| Trait Area: Salt tolerance, Water Use Efficiency, Nutrient Use Efficiency, Nutrient Utilization, Increased Biomass | |
| Sub-trait Area: Salt tolerance, Drought tolerance, Phosphate and Nitrate Use Efficiency, Phosphate and Nitrate Utilization, Plant Architecture, Enhanced Photosynthesis, Cell-wall composition and conversion | |
| Utility: Among other uses, this promoter sequence could be useful to improve: the biomass of the plants under normal and stressful conditions through the overexpression of transgenes that improve water use, nutrient use, alter composition, alter plant architecture, and improve the carbon-nitrogen balance. | |

Figure 2 (continued)

Analysis of Promoter PD3578 activity

| Promoter Expression Report For PD3578 (SEQ ID NO:10) | |
|---|---|
| Organism Evaluated: *Oryza sativa* | |
| Construct: PD3578 | |
| SR/OS Line: OS00676 | |
| Promoter candidate I.D: 58715987 | |
| Events expressing: 01-04, 06-07 | |
| Spatial expression summary:<br><br>T0 Seedling<br>LEAF<br><br>    EPIDERMIS    LEAF BLADE    LEAF SHEATH    MARGIN    MESOPHYLL    NOT-SPECIFIC<br><br>    PETIOLE    PRIMORDIA    STIPULE    STOMATA    TRICHOME    VASCULATURE<br><br>T0 Mature | |
| Observed expression pattern:<br>T0 Seedling: Expression is detected specifically in green leaf tissues.<br>T0 Mature expression: | |
| Gene: Sorghum Annot ID: 8743381 | |
| cDNA I.D: 88992707 | |
| GenBank: note   similar to PIR|S65073 fructose-bisphosphate aldolase (EC 4.1.2.13) isoenzyme C-1, cytosolic [Oryza sativa]; contains Pfam profile PF00274 Fructose-bisphosphate aldolase class-I; go_component: cytoplasm [goid 0005737]; go_function: fructose-bisphosphate aldolase activity [goid 0004332]; go_process: pentose-phosphate shunt [goid 0006098] PFAM        Glycolytic; | |
| Source Promoter Organism: *Sorghum bicolor* | |
| Vector: CRS830 Binary DF EGFP | |
| Marker Type: EGFP | |
| Generation Screened | |

| Table 1. T0 Seedling Expression    Organs/Tissues screened |
|---|
| Events Screened: n = 7   Events Expressing: n = 7   (01-04, 06, 07) |
| Organs<br>LEAF<br><br>    EPIDERMIS    LEAF BLADE    LEAF SHEATH    MARGIN    MESOPHYLL    NOT-SPECIFIC<br><br>    PETIOLE    PRIMORDIA    STIPULE    STOMATA    TRICHOME    VASCULATURE |
| Table 2. T0 Mature Plant Expression    Organs/Tissues screened |

Figure 2 (continued)

| | |
|---|---|
| Events Screened: n =    Events Expressing: n = | |
| Organs | |
| Table 3. Promoter utility | |
| Trait Area: Increased Biomass | |
| Sub-trait Area: Enhanced Photosynthesis, Cell-wall composition and conversion | |
| Utility: Among other uses, this promoter sequence could be useful to improve: the biomass of the plants under normal and stressful conditions through the overexpression of transgenes that improve the photosynthetic efficiency, the composition of the stems, and/or the carbon-nitrogen balance. | |

PD3775, a truncated version of promoter PD3578 (SEQ ID NO:10) containing nucleotides 1801 to 2500 of SEQ ID NO:10 was constructed and tested as described herein. No expression was observed for this truncated version.

Figure 2 (continued)

*Analysis of Promoter PD3579 activity*

| Promoter Expression Report For PD3579 (SEQ ID NO:11) | |
|---|---|
| Promoter Tested In: *Oryza sativa* | |
| Construct: PD3579 | |
| SR/OS Line: OS00678 | |
| Promoter candidate I.D: 57384219 | |
| Events expressing: 01-11 | |
| Spatial expression summary:<br><br>Callus:<br>Strong expression<br><br>T0 Seedling<br>TILLER<br>☑ NOT-SPECIFIC<br>MAIN CULM<br>☑ BUNDLE SHEATH ☑ ENDODERMIS ☑ EPIDERMIS ☑ INTERNODE ☑ LIGULE ☑ NODE<br>☑ NOT-SPECIFIC ☑ PERICYCLE ☑ PHLOEM ☑ SCLERENCHYMA LAYER ☑ VASCULATURE ☑ XYLEM<br>ROOT<br>☑ CORTEX ☑ EPIDERMIS ☑ NOT-SPECIFIC ☑ ROOT CAP ☐ VASCULAR<br>LEAF<br>☑ EPIDERMIS ☑ LEAF BLADE ☑ LEAF SHEATH ☐ MARGIN ☑ MESOPHYLL ☑ NOT-SPECIFIC<br>☑ PETIOLE ☐ PRIMORDIA ☑ STIPULE ☑ STOMATA ☐ TRICHOME ☑ VASCULATURE<br>MERISTEM<br>☐ FLORAL MERISTEM ☑ NOT-SPECIFIC ☐ SHOOT APICAL MERISTEM ☐ VEGETATIVE MERISTEM<br><br>T0 Mature | |
| Observed expression pattern:<br>Callus: Strong expression<br>T0 Seedling: Strong expression in all tissues analyzed<br>T0 Mature: | |
| Gene: Sorghum annot ID: 7953526 | |
| cDNA I.D: 88923113 | |
| GenBank: pfam: Ubiquitin; go function: protein degradation; | |
| Source Promoter Organism: *Sorghum bicolor* | |
| Vector: CRS803_Promoter_EGFP | |
| Marker Type: EGFP | |
| Generation Screened: T0 Seedling | |

Figure 2 (continued)

| Table 1. T0 Seedling Expression | Organs/Tissues screened |
|---|---|
| Events Screened: n = 11   Events Expressing: n = 11 (01-11) | |
| Organs | |
| T0 Seedling | |
| TILLER | |
| ☑ NOT-SPECIFIC | |
| MAIN CULM | |
| ☑ BUNDLE SHEATH   ☑ ENDODERMIS   ☑ EPIDERMIS   ☑ INTERNODE   ☑ LIGULE   ☑ NODE | |
| ☑ NOT-SPECIFIC   ☑ PERICYCLE   ☑ PHLOEM   ☑ SCLERENCHYMA LAYER   ☑ VASCULATURE   ☑ XYLEM | |
| ROOT | |
| ☑ CORTEX   ☑ EPIDERMIS   ☑ NOT-SPECIFIC   ☑ ROOT CAP   ☐ VASCULAR | |
| LEAF | |
| ☑ EPIDERMIS   ☑ LEAF BLADE   ☑ LEAF SHEATH   ☐ MARGIN   ☑ MESOPHYLL   ☑ NOT-SPECIFIC | |
| ☑ PETIOLE   ☐ PRIMORDIA   ☑ STIPULE   ☑ STOMATA   ☐ TRICHOME   ☑ VASCULATURE | |
| MERISTEM | |
| ☐ FLORAL MERISTEM   ☑ NOT-SPECIFIC   ☐ SHOOT APICAL MERISTEM   ☐ VEGETATIVE MERISTEM | |

| Table 2. T0 Mature Plant Expression | Organs/Tissues screened |
|---|---|
| Events Screened: n = | Events Expressing: n = |
| Organs | |

| Table 3. Promoter utility |
|---|
| Trait Area: Salt tolerance, Water Use Efficiency, Nutrient Use Efficiency, Nutrient Utilization, Increased Biomass, BioConfinement |
| Sub-trait Area: Salt tolerance, Drought tolerance, Phosphate and Nitrate Use Efficiency, Phosphate and Nitrate Utilization, Plant Architecture, Enhanced Photosynthesis, Cell-wall composition and conversion, Male sterility, Female sterility, Total sterility |
| Utility: Among other uses, this promoter sequence could be useful to improve: the biomass of the plants under normal and stressful conditions through the overexpression of transgenes that improve water use, nutrient use, alter composition, alter plant architecture, disrupt reproductive biology, and improve the carbon-nitrogen balance. |

Figure 2 (continued)

Analysis of Promoter PD3580 activity

| Promoter Expression Report For PD3580 (SEQ ID NO:12) | |
|---|---|
| Promoter Tested In: *Oryza sativa* | |
| Construct: PD3580 | |
| SR/OS Line: OS00679 | |
| Promoter candidate I.D: 57384217 | |
| Events expressing: 03-05-06-08-10-12 | |
| Spatial expression summary:<br><br>T0 Seedling<br>TILLER<br>☑ ALL TISSUES<br>MAIN CULM<br>☐ BUNDLE SHEATH  ☐ ENDODERMIS  ☐ EPIDERMIS  ☐ INTERNODE  ☐ LIGULE  ☐ NODE<br>☑ ALL TISSUES  ☐ PERICYCLE  ☐ PHLOEM  ☐ SCLERENCHYMA LAYER  ☐ VASCULATURE  ☐ XYLEM<br>ROOT<br>☐ CORTEX  ☐ EPIDERMIS  ☑ ALL TISSUES  ☐ ROOT CAP  ☐ VASCULAR<br>LEAF<br>☐ EPIDERMIS  ☐ LEAF BLADE  ☐ LEAF SHEATH  ☐ MARGIN  ☐ MESOPHYLL  ☑ ALL TISSUES<br>☐ PETIOLE  ☐ PRIMORDIA  ☐ STIPULE  ☐ STOMATA  ☐ TRICHOME  ☐ VASCULATURE<br>MERISTEM<br>☐ FLORAL MERISTEM  ☑ ALL TISSUES  ☐ SHOOT APICAL MERISTEM  ☐ VEGETATIVE MERISTEM<br><br>T0 Mature | |
| Observed expression pattern:<br>T0 Seedling: Expression observed strongly throughout all tissues of the seedling.<br>T0 Mature expression: | |
| Gene: Sorghum annot ID: 8744325 | |
| cDNA I.D: 88993479 | |
| GenBank: pfam: Ubiquitin; go function: protein degradation; | |
| Source Promoter Organism: *Sorghum bicolor* | |
| Vector: CRS830_Binary_DF_EGFP | |
| Marker Type: EGFP | |
| Generation Screened: T0 Seedling | |
| Table 1. T0 Seedling Expression   Organs/Tissues screened | |
| Events Screened: n = 12  Events Expressing: n = 6 (03,05,06,08,10,12) | |
| Organs<br>TILLER | |

Figure 2 (continued)

☑ ALL TISSUES

MAIN CULM

☐ BUNDLE SHEATH ☐ ENDODERMIS ☐ EPIDERMIS ☐ INTERNODE ☐ LIGULE ☐ NODE
☑ ALL TISSUES ☐ PERICYCLE ☐ PHLOEM ☐ SCLERENCHYMA LAYER ☐ VASCULATURE ☐ XYLEM

ROOT

☐ CORTEX ☐ EPIDERMIS ☑ ALL TISSUES ☐ ROOT CAP ☐ VASCULAR

LEAF

☐ EPIDERMIS ☐ LEAF BLADE ☐ LEAF SHEATH ☐ MARGIN ☐ MESOPHYLL ☑ ALL TISSUES
☐ PETIOLE ☐ PRIMORDIA ☐ STIPULE ☐ STOMATA ☐ TRICHOME ☐ VASCULATURE

MERISTEM

☐ FLORAL MERISTEM ☑ ALL TISSUES ☐ SHOOT APICAL MERISTEM ☐ VEGETATIVE MERISTEM

| Table 2. T0 Mature Plant Expression | Organs/Tissues screened |
|---|---|
| Events Screened: n = | Events Expressing: n = |
| Organs | |

| Table 3. Promoter utility |
|---|
| Trait Area: Salt tolerance, Water Use Efficiency, Nutrient Use Efficiency, Nutrient Utilization, Increased Biomass, BioConfinement |
| Sub-trait Area: Salt tolerance, Drought tolerance, Phosphate and Nitrate Use Efficiency, Phosphate and Nitrate Utilization, Plant Architecture, Enhanced Photosynthesis, Cell-wall composition and conversion, Male sterility, Female sterility, Total sterility |
| Utility: Among other uses, this promoter sequence could be useful to improve: the biomass of the plants under normal and stressful conditions through the overexpression of transgenes that improve water use, nutrient use, alter composition, alter plant architecture, disrupt reproductive biology, and improve the carbon-nitrogen balance. |

Figure 2 (continued)

Analysis of Promoter PD3655 activity

| | |
|---|---|
| Promoter Expression Report for PD3655 (SEQ ID NO:14) | |
| Organism Evaluated: *Oryza sativa* | |
| Construct: PD3655 | |
| SR/OS Line: OS00802 | |
| Promoter candidate I.D: 66234713 | |
| Events expressing: 01-07, 09-14 | |
| Spatial expression summary:<br><br>T0 Seedling<br>Events Screened: n = 15     Events Expressing: n = 14 (01-07, 09-14)<br>ROOT<br>☑ CORTEX  ☑ ENDODERMIS  ☑ EPIDERMIS  ☐ EXODERMIS  ☐ LATERAL ROOT  ☐ NOT-SPECIFIC<br>☐ ROOT CAP  ☐ VASCULAR<br><br>T0 Mature<br>Events Screened: n = 14     Events Expressing: n = 6 (02-05-06-07-09-12)<br>ROOT<br>☑ CORTEX  ☐ ENDODERMIS  ☐ EPIDERMIS  ☐ EXODERMIS  ☐ LATERAL ROOT  ☐ NOT-SPECIFIC<br>☐ ROOT CAP  ☐ VASCULAR | |
| Observed expression pattern:<br>T0 Seedling: GFP expression was only detected in lateral roots.<br>T0 Mature expression: Expression is strongest in roots. Lateral, fibrous roots have stronger expression than older, more mature roots. | |
| Selection Criteria: Putative ortholog of At4g12520/At4g12510. | |
| Gene: | |
| cDNA I.D: 71499034 | |
| GenBank: Pfam protease inhibitor/seed storage/LTP family domain PF00234 | |
| Source Promoter Organism: *Sorghum bicolor* | |
| Vector: CRS830 Binary DF EGFP | |
| Marker Type: EGFP | |
| Generation Screened: T0 Seedling and T0 Mature | |

Figure 2 (continued)

Analysis of Promoter PD3720 activity

| Promoter Expression Report for PD3720 (SEQ ID NO:15) | |
|---|---|
| Report Date: March 3rd, 2009 | |
| Organism Evaluated: *Oryza sativa* | |
| Construct: PD3720 | |
| SR/OS Line: OS00833 | |
| Promoter candidate I.D: 73638700 | |
| Events expressing: 06, 13-15 | |
| Spatial expression summary:<br><br>T0 Seedling<br>Events Screened: n = 16    Events Expressing: n = 0 (--)<br>No Expression<br><br>T0 Mature<br>Events Screened: n = 15    Events Expressing: n = 4 (06, 13-15)<br>SPIKELET<br><br>☐ ALEURONE LAYER  ☐ ANTHER  ☐ CARPEL  ☐ EMBRYO  ☐ ENDOSPERM  ☐ FILAMENT<br>☐ LEMMA  ☐ NOT-SPECIFIC  ☐ OVULE  ☐ PALEA  ☐ PEDICEL  ☐ POLLEN<br>☐ SEED  ☑ STIGMA  ☑ STYLE  ☑ LODICULE | |
| Observed expression pattern:<br>T0 Seedling: No expression was detected.<br>T0 Mature expression: Expression was only detected in the stigma, style, and lodicule of the floret. | |
| Selection Criteria: Member of the SEP family of genes in sorghum. Expect expression in floral meristem, prior to floral organ development. | |
| Gene: Putative MADS-BOX domain containing transcription factor | |
| cDNA I.D: 71491493 | |
| GenBank: K-box; SRF-TF | |
| Source Promoter Organism: *Sorghum bicolor* | |
| Vector: CRS830 Binary DF EGFP | |
| Marker Type: EGFP | |
| Generation Screened: T0 Seedling and T0 Mature | |

Figure 2 (continued)

Analysis of Promoter PD3777 activity

| Promoter Expression Report for PD3777 (nucleotides 501-2000 of SEQ ID NO:12) | |
|---|---|
| Organism Evaluated: *Oryza sativa* | |
| Construct: PD3777 | |
| SR/OS Line: OS00865 | |
| Promoter candidate I.D: 89744768 | |
| Events expressing: 2-7 | |
| Spatial expression summary: <br><br>T0 Seedling <br>Events Screened: n = 7      Events Expressing: n = 6 (02-07) <br>LEAF <br>☑ EPIDERMIS  ☑ FIBER CELLS  ☑ FLAG LEAF  ☐ GUARD CELL  ☑ LEAF BLADE  ☐ LEAF SHEATH <br>☐ MARGIN  ☐ MESOPHYLL  ☐ NOT-SPECIFIC  ☐ PETIOLE  ☐ PRIMORDIA  ☐ STIPULE <br>☑ STOMATA  ☐ TRICHOME  ☑ VASCULATURE <br>ROOT <br>☑ CORTEX  ☑ ENDODERMIS  ☑ EPIDERMIS  ☑ EXODERMIS  ☑ LATERAL ROOT  ☐ NOT-SPECIFIC <br>☑ ROOT CAP  ☑ VASCULAR <br>T0 Mature <br>Events Screened: n = 4      Events Expressing: n = 4 (03-05, 07) <br>LEAF <br>☑ EPIDERMIS  ☐ FIBER CELLS  ☑ FLAG LEAF  ☑ GUARD CELL  ☑ LEAF BLADE  ☐ LEAF SHEATH <br>☐ MARGIN  ☐ MESOPHYLL  ☐ NOT-SPECIFIC  ☐ PETIOLE  ☐ PRIMORDIA  ☐ STIPULE <br>☑ STOMATA  ☑ TRICHOME  ☐ VASCULATURE <br>SPIKELET <br>☐ ALEURONE LAYER  ☑ ANTHER  ☑ CARPEL  ☐ EMBRYO  ☐ ENDOSPERM  ☑ FILAMENT <br>☑ LEMMA  ☐ NOT-SPECIFIC  ☐ OVULE  ☐ PALEA  ☐ PEDICEL  ☑ POLLEN <br>☐ SEED  ☑ STIGMA <br>PANICLE <br>☐ NOT-SPECIFIC  ☐ OVARY  ☐ PEDUNCLE  ☐ PRIMARY BRANCH  ☐ RACHILLA  ☐ RACHIS <br>☑ SPIKELET <br>ROOT | |

Figure 2 (continued)

| | | | | | |
|---|---|---|---|---|---|
| ☐ CORTEX | ☑ ENDODERMIS | ☑ EPIDERMIS | ☐ EXODERMIS | ☐ LATERAL ROOT | ☐ NOT-SPECIFIC |
| ☑ ROOT CAP | ☑ VASCULAR | | | | |

MAIN CULM

| | | | | | |
|---|---|---|---|---|---|
| ☑ BUNDLE SHEATH | ☑ ENDODERMIS | ☑ EPIDERMIS | ☑ INTERNODE | ☐ LIGULE | ☐ NODE |
| ☐ NOT-SPECIFIC | ☐ PERICYCLE | ☐ PHLOEM | ☑ SCLERENCHYMA LAYER | ☑ VASCULATURE | ☐ XYLEM |

| |
|---|
| Observed expression pattern: |
| T0 Seedling: Expression observed strongly throughout all tissues of the seedling. |
| T0 Mature expression: Expression observed strongly throughout all tissues of the mature plant. |
| Selection Criteria: Deletion of promoter PD3580 |
| Gene: Sorghum annot ID: 8744325 |
| cDNA I.D: 88993479 |
| GenBank: pfam: Ubiquitin; go function: protein degradation; |
| Source Promoter Organism: *Sorghum bicolor* |
| Vector: NB4_Kan |
| Marker Type: EGFP |
| Generation Screened: T0 Seedling and T0 Mature |

| |
|---|
| Promoter utility |
| Trait Area: Salt tolerance, Water Use Efficiency, Nutrient Use Efficiency, Nutrient Utilization, Increased Biomass, BioConfinement |
| Sub-trait Area: Salt tolerance, Drought tolerance, Phosphate and Nitrate Use Efficiency, Phosphate and Nitrate Utilization, Plant Architecture, Enhanced Photosynthesis, Cell-wall composition and conversion, Male sterility, Female sterility, Total sterility |
| Utility: Among other uses, this promoter sequence could be useful to improve: the biomass of the plants under normal and stressful conditions through the overexpression of transgenes that improve water use, nutrient use, alter composition, alter plant architecture, disrupt reproductive biology, and improve the carbon-nitrogen balance. |

Figure 2 (continued)

Analysis of Promoter PD3786 activity

| Promoter Expression Report for PD3786 (SEQ ID NO:16) | |
|---|---|
| Organism Evaluated: *Oryza sativa* | |
| Construct: PD3786 | |
| SR/OS Line: OS00877 | |
| Promoter candidate I.D: 72581277 | |
| Events expressing: 3-7,11,12 | |
| Spatial expression summary: | |

T0 Seedling
Events Screened: n = 14    Events Expressing: n = 7 (3-7,11,12)

LEAF
- ☐ EPIDERMIS  ☐ FIBER CELLS  ☐ FLAG LEAF  ☐ GUARD CELL  ☐ LEAF BLADE  ☐ LEAF SHEATH
- ☐ MARGIN  ☑ MESOPHYLL  ☐ NOT-SPECIFIC  ☐ PETIOLE  ☐ PRIMORDIA  ☐ STIPULE
- ☐ STOMATA  ☐ TRICHOME  ☐ VASCULATURE

TILLER
- ☐ BUNDLE SHEATH  ☐ ENDODERMIS  ☐ EPIDERMIS  ☑ MESOPHYLL  ☐ NOT-SPECIFIC  ☐ PHLOEM
- ☐ SCLERENCHYMA LAYER  ☐ VASCULATURE  ☐ XYLEM

T0 Mature
Events Screened: n = 3    Events Expressing: n = 3 (06, 11, 12)

LEAF
- ☐ EPIDERMIS  ☐ FIBER CELLS  ☐ FLAG LEAF  ☐ GUARD CELL  ☐ LEAF BLADE  ☐ LEAF SHEATH
- ☐ MARGIN  ☑ MESOPHYLL  ☐ NOT-SPECIFIC  ☐ PETIOLE  ☐ PRIMORDIA  ☐ STIPULE
- ☐ STOMATA  ☐ TRICHOME  ☐ VASCULATURE

SPIKELET
- ☐ ALEURONE LAYER  ☐ ANTHER  ☐ CARPEL  ☑ EMBRYO  ☑ ENDOSPERM  ☐ FILAMENT
- ☑ LEMMA  ☐ NOT-SPECIFIC  ☐ OVULE  ☐ PALEA  ☐ PEDICEL  ☐ POLLEN
- ☑ SEED  ☐ STIGMA

PANICLE
- ☑ NOT-SPECIFIC  ☐ OVARY  ☐ PEDUNCLE  ☐ PRIMARY BRANCH  ☐ RACHILLA  ☐ RACHIS

Figure 2 (continued)

☑ SPIKELET
ROOT
☐ CORTEX  ☐ ENDODERMIS  ☑ EPIDERMIS  ☑ EXODERMIS  ☐ LATERAL ROOT  ☐ NOT-SPECIFIC
☐ ROOT CAP  ☑ VASCULAR
MAIN CULM
☑ BUNDLE SHEATH  ☐ ENDODERMIS  ☐ EPIDERMIS  ☐ INTERNODE  ☐ LIGULE  ☐ NODE
☐ NOT-SPECIFIC  ☐ PERICYCLE  ☑ PHLOEM  ☐ SCLERENCHYMA LAYER  ☐ VASCULATURE  ☐ XYLEM

| | |
|---|---|
| Observed expression pattern: | |
| T0 Seedling: GFP expression was only detected in the mesophyll of the leaves and stems. | |
| T0 Mature expression: Expression was very strong in the mesophyll cells of the above ground tissues. Faint expression was detected in the roots. | |
| Selection Criteria: Based upon: 1) # publicly available EST clones mapped into sorghum genome and 2) # clones in SWG EST clusters | |
| Gene: Putative Chlorophyll A-B binding protein | |
| cDNA I.D: 71463851 | |
| GenBank: Chlorophyll A-B binding protein | |
| Source Promoter Organism: *Sorghum bicolor* | |
| Vector: CRS830 Binary DF EGFP | |
| Marker Type: EGFP | |
| Generation Screened: T0 Seedling and T0 Mature | |

| |
|---|
| Promoter utility |
| Trait Area: Biomass |
| Sub-trait Area: Enhanced photosynthesis |
| Utility: Among other uses, this promoter sequence could be useful to engineer the enhancement of the photosynthetic pathways to increase energy capture from sunlight. |

Figure 2 (continued)

*Analysis of Promoter PD3805 activity*

| Promoter Expression Report for PD3805 (SEQ ID NO:17) | |
|---|---|
| Organism Evaluated: *Oryza sativa* | |
| Construct: PD3805 | |
| SR/OS Line: OS00888 | |
| Promoter candidate I.D: 90379178 | |
| Events expressing: 2,3,5 | |
| Spatial expression summary: | |

T0 Seedling
Events Screened: n = 5    Events Expressing: n = 3 (2,3,5)
LEAF
☐ EPIDERMIS  ☐ FIBER CELLS  ☐ FLAG LEAF  ☐ GUARD CELL  ☐ LEAF BLADE  ☐ LEAF SHEATH
☐ MARGIN  ☐ MESOPHYLL  ☑ NOT-SPECIFIC  ☐ PETIOLE  ☐ PRIMORDIA  ☐ STIPULE
☐ STOMATA  ☐ TRICHOME  ☐ VASCULATURE
TILLER
☐ BUNDLE SHEATH  ☐ ENDODERMIS  ☐ EPIDERMIS  ☐ MESOPHYLL  ☑ NOT-SPECIFIC  ☐ PHLOEM
☐ SCLERENCHYMA LAYER  ☐ VASCULATURE  ☐ XYLEM
ROOT
☐ CORTEX  ☐ ENDODERMIS  ☐ EPIDERMIS  ☐ EXODERMIS  ☐ LATERAL ROOT  ☑ NOT-SPECIFIC
☐ ROOT CAP  ☐ VASCULAR

T0 Mature
Events Screened: n = 3    Events Expressing: n = 3 (2,3,5)
LEAF
☑ EPIDERMIS  ☐ FIBER CELLS  ☑ FLAG LEAF  ☑ GUARD CELL  ☑ LEAF BLADE  ☐ LEAF SHEATH
☐ MARGIN  ☑ MESOPHYLL  ☐ NOT-SPECIFIC  ☐ PETIOLE  ☐ PRIMORDIA  ☐ STIPULE
☐ STOMATA  ☐ TRICHOME  ☑ VASCULATURE
SPIKELET
☐ ALEURONE LAYER  ☑ ANTHER  ☐ CARPEL  ☐ EMBRYO  ☐ ENDOSPERM  ☑ FILAMENT
☑ LEMMA  ☐ NOT-SPECIFIC  ☑ OVULE  ☐ PALEA  ☐ PEDICEL  ☑ POLLEN

Figure 2 (continued)

☐ SEED  ☑ STIGMA

PANICLE

☐ NOT-SPECIFIC  ☐ OVARY  ☑ PEDUNCLE  ☐ PRIMARY BRANCH  ☐ RACHILLA  ☐ RACHIS

☑ SPIKELET

ROOT

☑ CORTEX  ☐ ENDODERMIS  ☐ EPIDERMIS  ☐ EXODERMIS  ☐ LATERAL ROOT  ☐ NOT-SPECIFIC

☐ ROOT CAP  ☑ VASCULAR

MAIN CULM

☑ BUNDLE SHEATH  ☑ ENDODERMIS  ☑ EPIDERMIS  ☑ INTERNODE  ☐ LIGULE  ☑ NODE

☐ NOT-SPECIFIC  ☑ PERICYCLE  ☐ PHLOEM  ☐ SCLERENCHYMA LAYER  ☑ VASCULATURE  ☐ XYLEM

| |
|---|
| Observed expression pattern: |
| T0 Seedling: Expression observed strongly in both above ground and root vegetative tissues. |
| T0 Mature expression: Expression observed strongly throughout all tissues of the mature plant. |
| Selection Criteria: Ortholog of At4g38970, above ground expression in Arabidopsis |
| Gene: Sorghum annot ID: 8715723 |
| cDNA I.D: 88878990 |
| GenBank: strong similarity to plastidic fructose-bisphosphate aldolase |
| Source Promoter Organism: *Sorghum bicolor* |
| Vector: NB4_Kan |
| Marker Type: EGFP |
| Generation Screened: T0 Seedling and T0 Mature |

Figure 2 (continued)

Analysis of Promoter PD3812 activity

| Promoter Expression Report for PD3812 (SEQ ID NO:18) | |
|---|---|
| Organism Evaluated: *Oryza sativa* | |
| Construct: PD3812 | |
| SR/OS Line: OS00867 | |
| Promoter candidate I.D: 89744767 | |
| Events expressing: 01,02, 04-09 | |

Spatial expression summary:

T0 Seedling
Events Screened: n = 9    Events Expressing: n = 8 (01,02, 04-09)
LEAF
☑ EPIDERMIS  ☑ FIBER CELLS  ☐ FLAG LEAF  ☐ GUARD CELL  ☐ LEAF BLADE  ☐ LEAF SHEATH
☐ MARGIN  ☐ MESOPHYLL  ☐ NOT-SPECIFIC  ☐ PETIOLE  ☐ PRIMORDIA  ☐ STIPULE
☑ STOMATA  ☐ TRICHOME  ☐ VASCULATURE
ROOT
☑ CORTEX  ☐ ENDODERMIS  ☑ EPIDERMIS  ☐ EXODERMIS  ☐ LATERAL ROOT  ☐ NOT-SPECIFIC
☑ ROOT CAP  ☐ VASCULAR

T0 Mature
Events Screened: n = 7    Events Expressing: n = 7 (02, 04-09)
LEAF
☑ EPIDERMIS  ☑ FIBER CELLS  ☑ FLAG LEAF  ☑ GUARD CELL  ☑ LEAF BLADE  ☐ LEAF SHEATH
☐ MARGIN  ☑ MESOPHYLL  ☐ NOT-SPECIFIC  ☐ PETIOLE  ☐ PRIMORDIA  ☐ STIPULE
☑ STOMATA  ☐ TRICHOME  ☑ VASCULATURE
SPIKELET
☐ ALEURONE LAYER  ☑ ANTHER  ☑ CARPEL  ☐ EMBRYO  ☐ ENDOSPERM  ☑ FILAMENT
☑ LEMMA  ☐ NOT-SPECIFIC  ☐ OVULE  ☐ PALEA  ☐ PEDICEL  ☐ POLLEN
☐ SEED  ☑ STIGMA
PANICLE
☐ NOT-SPECIFIC  ☐ OVARY  ☑ PEDUNCLE  ☑ PRIMARY BRANCH  ☐ RACHILLA  ☐ RACHIS
☑ SPIKELET

Figure 2 (continued)

| ROOT | | | | | | |
|---|---|---|---|---|---|---|
| ☑ CORTEX | ☐ ENDODERMIS | ☑ EPIDERMIS | ☐ EXODERMIS | ☐ LATERAL ROOT | ☐ NOT-SPECIFIC | |
| ☑ ROOT CAP | ☑ VASCULAR | | | | | |
| MAIN CULM | | | | | | |
| ☑ BUNDLE SHEATH | ☑ ENDODERMIS | ☑ EPIDERMIS | ☐ INTERNODE | ☐ LIGULE | ☐ NODE | |
| ☐ NOT-SPECIFIC | ☐ PERICYCLE | ☐ PHLOEM | ☐ SCLERENCHYMA LAYER | ☑ VASCULATURE | ☐ XYLEM | |

| |
|---|
| Observed expression pattern: |
| T0 Seedling: Strong expression in all tissues analyzed |
| T0 Mature: Strong expression in all tissues analyzed |
| Selection Criteria: Ubiquitin promoter homolog from Sorghum |
| Gene: Sorghum annot ID: 7953526 |
| cDNA I.D: 88923100 |
| GenBank: pfam: Ubiquitin; go function: protein degradation; |
| Source Promoter Organism:     *Sorghum bicolor* |
| Vector: NB4_Kan |
| Marker Type: EGFP |
| Generation Screened: T0 Seedling and T0 Mature |

| |
|---|
| Promoter utility |
| Trait Area: Salt tolerance, Water Use Efficiency, Nutrient Use Efficiency, Nutrient Utilization, Increased Biomass, BioConfinement |
| Sub-trait Area: Salt tolerance, Drought tolerance, Phosphate and Nitrate Use Efficiency, Phosphate and Nitrate Utilization, Plant Architecture, Enhanced Photosynthesis, Cell-wall composition and conversion, Male sterility, Female sterility, Total sterility |
| Utility: Among other uses, this promoter sequence could be useful to improve: the biomass of the plants under normal and stressful conditions through the overexpression of transgenes that improve water use, nutrient use, alter composition, alter plant architecture, disrupt reproductive biology, and improve the carbon-nitrogen balance. |

Figure 2 (continued)

PROMOTER, PROMOTER CONTROL ELEMENTS, AND COMBINATIONS, AND USES THEREOF

CROSS-REFERENCE TO RELATED APPLICATIONS

This application is a divisional application and claims the benefit of U.S. application Ser. No. 12/895,475, filed on Sep. 30, 2013 which is a continuation of International Application No. PCT/US2009/038792, filed Mar. 30, 2009, which claims the benefit of U.S. Provisional Application Ser. No. 61/041,018, filed on Mar. 31, 2008. The disclosures of the prior applications are incorporated by reference in their entirety.

INCORPORATION-BY-REFERENCE OF SEQUENCE LISTING OR TABLE

The material in the accompanying sequence listing is hereby incorporated by reference into this application. The accompanying file, named 11696-251WO1_sequence_listing was created on Sep. 30, 2010 and is 43.1 KB. The file can be accessed using Microsoft Word on a computer that uses Windows OS.

TECHNICAL FIELD

The present invention relates to promoters and promoter control elements that are useful for modulating transcription of a desired polynucleotide. Such promoters and promoter control elements can be included in polynucleotide constructs, expression cassettes, vectors, or inserted into the chromosome or as an exogenous element, to modulate in vivo and in vitro transcription of a polynucleotide. Host cells, including plant cells, and organisms, such as regenerated plants therefrom, with desired traits or characteristics using polynucleotides comprising the promoters and promoter control elements described herein are also a part of the invention.

BACKGROUND

This document relates to promoter sequences and promoter control element sequences which are useful for the transcription of polynucleotides in a host cell or transformed host organism.

The introduction of genes into plants has resulted in the development of plants having new and useful phenotypes such as pathogen resistance, higher levels of healthier types of oils, novel production of healthful components such as beta-carotene synthesis in rice. An introduced gene is generally a chimeric gene composed of the coding region that confers the desired trait and regulatory sequences. One regulatory sequence is the promoter, which is located 5' to the coding region. This sequence is involved in regulating the pattern of expression of a coding region 3' thereof. The promoter sequence binds RNA polymerase complex as well as one or more transcription factors that are involved in producing the RNA transcript of the coding region.

The promoter region of a gene used in plant transformation is most often derived from a different source than is the coding region. It may be from a different gene of the same species of plant, from a different species of plant, from a plant virus, an algae species, a fungal species, or it may be a composite of different natural and/or synthetic sequences. Properties of the promoter sequence generally determine the pattern of expression for the coding region that is operably linked to the promoter. Promoters with different characteristics of expression have been described. The promoter may confer broad expression as in the case of the widely-used cauliflower mosaic virus (CaMV) 35S promoter. The promoter may confer tissue-specific expression as in the case of the seed-specific phaseolin promoter. The promoter may confer a pattern for developmental changes in expression. The promoter may be induced by an applied chemical compound, or by an environmental condition applied to the plant.

The promoter that is used to regulate a particular coding region is determined by the desired expression pattern for that coding region, which itself is determined by the desired resulting phenotype in the plant. For example, herbicide resistance is desired throughout the plant so the 35S promoter is appropriate for expression of an herbicide-resistance gene. A seed-specific promoter is appropriate for changing the oil content of soybean seed. An endosperm-specific promoter is appropriate for changing the starch composition of corn seed. A root-specific promoter can be important for improving water or nutrient up-take in a plant. Control of expression of an introduced gene by the promoter is important because it is sometimes detrimental to have expression of an introduced gene in non-target tissues. For example, a gene which induces cell death can be expressed in male and/or female gamete cells in connection with bioconfinement.

One of the primary goals of biotechnology is to obtain organisms, such as plants, mammals, yeast, and prokaryotes having particular desired characteristics or traits. Examples of these characteristics or traits abound and may include, for example, in plants, virus resistance, insect resistance, herbicide resistance, enhanced stability or additional nutritional value. Recent advances in genetic engineering have enabled researchers in the field to incorporate polynucleotide sequences into host cells to obtain the desired qualities in the organism of choice. This technology permits one or more polynucleotides from a source different than the organism of choice to be transcribed by the organism of choice. If desired, the transcription and/or translation of these new polynucleotides can be modulated in the organism to exhibit a desired characteristic or trait. Alternatively, new patterns of transcription and/or translation of polynucleotides endogenous to the organism can be produced.

SUMMARY

The present document is directed to isolated polynucleotide sequences that comprise promoters and promoter control elements from plants, especially *Sorghum bicolor*, and other promoters and promoter control elements functional in plants. It is an object of the present document to provide isolated polynucleotides that are promoter or promoter control sequences. These promoter sequences comprise, for example, (1) a polynucleotide having a nucleotide sequence according to SEQ. ID. NOs. 1-18;

(2) a polynucleotide having a nucleotide sequence having at least 80% sequence identity to a sequence according to SEQ. ID. NOs. 1-18; and (3) a polynucleotide having a nucleotide sequence which hybridizes to a sequence according to SEQ. ID. NOs. 1-18 under a condition establishing a Tm−5° C.

Promoter or promoter control element sequences of the present document are capable of modulating preferential transcription. In one embodiment, this document features an isolated nucleic acid that includes a regulatory region having 90 percent or greater sequence identity (e.g., 95 percent or greater, or 98 percent or greater) to the nucleotide sequence set forth in any one of SEQ ID NOs. 1-18 or a fragment thereof, wherein the regulatory region directs transcription of an operably linked heterologous polynucleotide. The nucleic acid can include one or more motifs selected from the group consisting of an ABRE motif, ABREATRD22 motif, ABRERATCAL motif, ABREZMRAB28 motif, ACGTABREMOTIFA2OSEM motif, ACIIPVPAL2 motif, AGCBOXNPGLB motif, AMYBOX1 motif, ARE1 motif, ATHB1ATCONSENSUS motif, ATHB6COREAT motif, AUXRETGA2GMGH3 motif, BOXIIPCCHS motif, CAAT-BOX1 motif, CACGCAATGMGH3 motif, CARGCW8GAT motif, CCA1ATLHCB1 motif, CEREGLUBOX2PSLEGA motif, E2FAT motif, E2FCONSENSUS motif, ERELEE4 motif, GADOWNAT motif, GARE1OSREP1 motif, GAREAT motif, IBOX-CORENT motif, INRNTPSADB motif, LRENPCABE motif, MARTBOX motif, MYBGAHV motif, MYBPLANT motif, NRRBNEXTA motif, P1BS motif, PRECONSCRHSP70A motif, ROOTMOTIFTAPDX1 motif, RYREPEATGMGY2 motif, RYREPEATVFLEB4 motif, SBOXATRBCS motif, SP8BFIBSP8BIB motif, SPH-COREZMC1 motif, TATABOX1 motif, TATABOX2 motif, TATABOX4 motif, TATABOXOSPAL motif, TATCCAYMOTIFOSRAMY3D motif, TE2F2NTPCNA motif, TRANSINITMONOCOTS motif, UP2ATMSD motif, and UPRMOTIFIIAT motif.

This document also features a vector construct that includes a first nucleic acid that includes a regulatory region having 90 percent or greater sequence identity (e.g., 95 percent or greater, or 98 percent or greater) to any one of SEQ ID NOs. 1-18 or a fragment thereof, wherein the regulatory region directs transcription of an operably linked heterologous polynucleotide; and a second nucleic acid to be transcribed, wherein the first and second nucleic acids are heterologous to each other and are operably linked. In some embodiments, the first nucleic acid consists of the nucleic acid set forth in any one of SEQ ID NOs: 1-18. In some embodiments, the second nucleic acid includes a nucleic acid sequence that encodes a polypeptide. The second nucleic acid can be operably linked to the first nucleic acid in sense orientation. In some embodiments, the second nucleic acid can be transcribed into an RNA molecule that expresses the polypeptide encoded by the second nucleic acid. The second nucleic acid can be operably linked to the first nucleic acid in antisense orientation. The second nucleic acid can be transcribed into an antisense RNA molecule. The second nucleic acid can be transcribed into an interfering RNA against an endogenous gene.

In another aspect, this document features a transgenic plant or plant cell transformed with an isolated nucleic acid described herein that is operably linked to a heterologous polynucleotide, or a vector construct described herein. This document also features seeds of such a plant. In some embodiments, the heterologous nucleic acid encodes a polypeptide of agronomic interest.

This document also features a method of directing transcription by combining, in an environment suitable for transcription: a first nucleic acid that includes a regulatory region having 90 percent or greater sequence identity (e.g., 95 percent or greater, or 98 percent or greater) to any one of SEQ ID NOs. 1-18 or a fragment thereof; and a second nucleic acid to be transcribed; wherein the first and second nucleic acids are heterologous to each other and operably linked. The first nucleic acid molecule can consist of a sequence according to any one of SEQ ID NOs: 1-18. The operably linked first and second nucleic acids can be inserted into a plant cell and the plant cell regenerated into a plant.

In yet another aspect, this document features a method of expressing an exogenous coding region in a plant. The method includes transforming a plant cell with a vector described herein; regenerating a stably transformed plant from the transformed plant cell; and selecting plants containing a transformed plant cell, wherein expression of the vector results in production of a polypeptide encoded by the second nucleic acid.

This document also features a method of altering the expression of a gene in a plant. The method includes transforming a plant cell with a nucleic acid described herein that is operably linked to a heterologous polynucleotide, and regenerating stably transformed plants from the transformed plant cell. Plants prepared according to such a method also are featured, as well as seeds obtained from such plants.

In another aspect, this document features a method of producing a transgenic plant. The method introducing into a plant cell (i) an isolated polynucleotide described herein that is operably linked to a heterologous polynucleotide, or (ii) a vector described herein, and growing a plant from the plant cell. The heterologous polynucleotide can include a nucleic acid sequence encoding a polypeptide. The heterologous polynucleotide can be operably linked to the regulatory region in the antisense orientation. The heterologous polynucleotide can be transcribed into an interfering RNA.

In another embodiment, the present promoter control elements are capable of serving as or fulfilling the function, for example, as a core promoter, a TATA box, a polymerase binding site, an initiator site, a transcription binding site, an enhancer, an inverted repeat, a locus control region, and/or a scaffold/matrix attachment region.

It is yet another object of the present document to provide a polynucleotide that includes at least a first and a second promoter control element. The first promoter control element is a promoter control element sequence as discussed above, and the second promoter control element is heterologous to the first control element; wherein, the first and second control elements are operably linked. Such promoters may modulate transcript levels preferentially in a particular tissue or under particular conditions.

In another embodiment, the present isolated polynucleotide comprises a promoter or a promoter control element as described above, wherein the promoter or promoter control element is operably linked to a polynucleotide to be transcribed.

In another embodiment of the present document, the promoter and promoter control elements of the instant document are operably linked to a heterologous polynucleotide that is a regulatory sequence.

It is another object of the present document to provide a host cell comprising an isolated polynucleotide or vector as described above or fragment thereof. Host cells include, for instance, bacterial, yeast, insect, mammalian, fungus, algae, and plant. The host cell can comprise a promoter or promoter control element exogenous to the genome. Such a promoter can modulate transcription in cis- and in trans-. In yet another embodiment, the host cell is a plant cell capable of regenerating into a plant.

It is another object of the present document to provide a method of modulating transcription in a sample that contains either a cell-free system of transcription or host cell. This method comprises providing a polynucleotide or vector according to the present document as described above, and contacting the sample of the polynucleotide or vector with conditions that permit transcription.

In another embodiment of the present method, the polynucleotide or vector preferentially modulates, depending upon the function of the particular promoter, constitutive transcription, stress induced transcription, light induced transcription, dark induced transcription, leaf transcription, root transcription, stem or shoot transcription, silique or fruit transcription, callus transcription, rhizome transcription, stem node transcription, gamete tissue transcription, flower transcription, immature bud or floret and inflorescence specific transcription, senescing induced transcription, germination transcription and/or drought transcription.

Other and further objects of the present document will be made clear or become apparent from the following description.

BRIEF DESCRIPTION OF THE TABLES AND FIGURES

The Tables consist of the Expression Reports) for each promoter described herein and provide the nucleotide sequence for each promoter and details for expression driven by each of the nucleic acid promoter sequences as observed in transgenic plants. The results are presented as summaries of the spatial expression, which provides information as to gross and/or specific expression in various plant organs and tissues. The observed expression pattern is also presented, which gives details of expression during different generations or different developmental stages within a generation. Additional information is provided regarding the source organism of the promoter, and the vector and marker genes used for the construct. The following symbols are used consistently throughout the Tables:

T0: First generation transformant

T1: Second generation transformant

Each row of the table begins with heading of the data to be found in the section. The following provides a description of the data to be found in each section:

| Heading in Tables | Description |
| --- | --- |
| 1. Promoter tested in: | Identifies the organism in which the promoter-marker vector was tested. |
| 2. Construct: | Identifies the promoter by its construct ID |
| 3. Line: | Identifies the transgenic line that contains the promoter construct |
| 4. Promoter Candidate: | Provides an internal ID number for the promoter. |
| 5. Event Expressing: | Identifies the event numbers that expressed under the promoter. |
| 6. Spatial expression summary: | Identifies the specific parts of the plant where various levels of GFP expression are observed. |
| 7. Observed expression pattern: | Provides a general explanation of where GFP expression in different generations of plants was observed. |
| 8. Gene: | Identifies genomic annotation of the coding sequence that corresponds to the promoter candidate |
| 9. cDNA I.D.: | Internal predicted gene model corresponding to the genomic annotation |
| 10. GenBank: | pFAM annotation predicted by GenBank |
| 11. Source Promoter Organism | Identifies the plant species from which the promoter was derived. |
| 12. Vector: | Identifies the vector into which a promoter was cloned. |

| Heading in Tables | Description |
| --- | --- |
| 13. Marker Type: | Identifies the type of marker linked to the promoter. The marker is used to determine patterns of gene expression in plant tissue. |
| 14. Generation screened: T0 Seedling T0 Mature T1 Seedling | Identifies the plant generation(s) used in the screening process. T0 plants are primary transformants regenerated directly from tissue culture while the T1 generation plants are from the seeds collected from the T0 plants. |
| 16. T0 Seedling Expression: | Identifies plant tissues that were observed for possible expression. |
| 17. T0 Mature Plant Expression: | Identifies plant tissues that were observed for possible expression |
| 18. T1 Mature Plant Expression: | Identifies plant tissues that were observed for possible expression |
| 19. Promoter Utility | Provides a description of the utility of the sequence. |

FIG. 1—CRS380—Promoter_EGFP

FIG. 1 is a schematic representation of a vector that is useful to insert promoters described herein into a plant. The definitions of the abbreviations used in the vector map are as follows: Ori—the origin of replication used by an *E. coli* host; RB—sequence for the right border of the T-DNA from pMOG800; SfiI—restriction enzyme cleavage site used for cloning; EGFP—an enhanced version of the green fluorescent protein gene; OCS—the terminator sequence from the octopine synthase gene; p28716 (a.k.a 28716 short)—promoter used to drive expression of the PAT (BAR) gene; PAT (BAR)—a marker gene conferring herbicide resistance; LB—sequence for the left border of the T-DNA from pMOG800; Spec—a marker gene conferring spectinomycin resistance; TrfA—transcription repression factor gene; RK2-OriV—origin of replication for *Agrobacterium*.

FIG. 2—Promoter Expression Reports

FIG. 2 represents the Promoter Expression Reports of the Tables that present the results of the GFP assays as reported by their corresponding construct number and line number.

DETAILED DESCRIPTION

The following definitions and methods are provided to better define the present invention and to guide those of ordinary skill in the art in the practice of the present invention. Unless otherwise noted, terms are to be understood according to conventional usage by those of ordinary skill in the relevant art.

The document disclosed herein provides promoters capable of driving the expression of an operably linked transgene. The design, construction, and use of these promoters is one object of this document. The promoter sequences, SEQ ID NOs: 1-18, are capable of transcribing operably linked nucleic acid molecules in particular plant tissues/organs or during particular plant growth stages, and therefore can selectively regulate expression of transgenes in these tissues/organs or at these times of plant development.

1. Definitions

The terms "nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded, i.e., a sense strand or an antisense strand. Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

An isolated nucleic acid can be, for example, a naturally-occurring DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences, e.g., a chemically synthesized nucleic acid, or a cDNA or genomic DNA fragment produced by the polymerase chain reaction (PCR) or restriction endonuclease treatment. An isolated nucleic acid also refers to a DNA molecule that is incorporated into a vector, an autonomously replicating plasmid, or a virus, or transformed into the genome of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Chimeric: The term "chimeric" is used to describe polynucleotides or genes, or constructs wherein at least two of the elements of the polynucleotide or gene or construct, such as the promoter and the polynucleotide to be transcribed and/or other regulatory sequences and/or filler sequences and/or complements thereof, are heterologous to each other.

Broadly Expressing Promoter: Promoters referred to herein as "broadly expressing promoters" actively promote transcription under most, but not necessarily all, environmental conditions and states of development or cell differentiation. Examples of broadly expressing promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

Domain: Domains are fingerprints or signatures that can be used to characterize protein families and/or parts of proteins. Such fingerprints or signatures can comprise conserved (1) primary sequence, (2) secondary structure, and/or (3) three-dimensional conformation. A similar analysis can be applied to polynucleotides. Generally, each domain has been associated with either a conserved primary sequence or a sequence motif Generally these conserved primary sequence motifs have been correlated with specific in vitro and/or in vivo activities. A domain can be any length, including the entirety of the polynucleotide to be transcribed. Examples of domains include, without limitation, AP2, helicase, homeobox, zinc finger, etc.

Endogenous: The term "endogenous," within the context of the current document refers to any polynucleotide, polypeptide or protein sequence which is a natural part of a cell or organism(s) regenerated from said cell. In the context of promoter, the term "endogenous coding region" or "endogenous cDNA" refers to the coding region that is naturally operably linked to the promoter.

Enhancer/Suppressor: An "enhancer" is a DNA regulatory element that can increase the steady state level of a transcript, usually by increasing the rate of transcription initiation. Enhancers usually exert their effect regardless of the distance, upstream or downstream location, or orientation of the enhancer relative to the start site of transcription. In contrast, a "suppressor" is a corresponding DNA regulatory element that decreases the steady state level of a transcript, again usually by affecting the rate of transcription initiation. The essential activity of enhancer and suppressor elements is to bind a protein factor(s). Such binding can be assayed, for example, by methods described below. The binding is typically in a manner that influences the steady state level of a transcript in a cell or in an in vitro transcription extract.

Exogenous: As referred to within, "exogenous" is any polynucleotide, polypeptide or protein sequence, whether chimeric or not, that is introduced into the genome of a host cell or organism regenerated from said host cell by any means other than by a sexual cross. Examples of means by which this can be accomplished are described below, and include *Agrobacterium*-mediated transformation (of dicots—e.g. Salomon et al. (1984) *EMBO J.* 3:141; Herrera-Estrella et al. (1983) *EMBO J.* 2:987; of monocots, representative papers are those by Escudero et al. (1996) *Plant J.* 10:355), Ishida et al. (1996) *Nature Biotech* 14:745, May et al. (1995) *Bio/Technology* 13:486), biolistic methods (Armaleo et al. (1990) Current Genetics 17:97), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Homologous: In the current document, a "homologous" polynucleotide refers to a polynucleotide that shares sequence similarity with the polynucleotide of interest. This similarity may be in only a fragment of the sequence and often represents a functional domain such as, examples including, without limitation, a DNA binding domain or a domain with tyrosine kinase activity. The functional activities of homologous polynucleotides are not necessarily the same.

Inducible Promoter: An "inducible promoter" in the context of the current document refers to a promoter, the activity of which is influenced by certain conditions, such as light, temperature, chemical concentration, protein concentration, conditions in an organism, cell, or organelle, etc. A typical example of an inducible promoter, which can be utilized with the polynucleotides of the present document, is PARSK1, the promoter from an *Arabidopsis* gene encoding a serine-threonine kinase enzyme, and which promoter is induced by dehydration, abscissic acid and sodium chloride (Wang and Goodman (1995) *Plant J.* 8:37). Examples of environmental conditions that may affect transcription by inducible promoters include anaerobic conditions, elevated temperature, the presence or absence of a nutrient or other chemical compound or the presence of light.

Misexpression: The term "misexpression" refers to an increase or a decrease in the transcription of a coding region into a complementary RNA sequence as compared to the wild-type. This term also encompasses expression and/or translation of a gene or coding region or inhibition of such transcription and/or translation for a different time period as compared to the wild-type and/or from a non-natural location within the plant genome, including a gene or coding region from a different plant species or from a non-plant organism.

Modulate Transcription Level: As used herein, the phrase "modulate transcription" describes the biological activity of a promoter sequence or promoter control element. Such modulation includes, without limitation, up- and down-regulation of initiation of transcription, rate of transcription, and/or transcription levels.

Operable Linkage: An "operable linkage" is a linkage in which a promoter sequence or promoter control element is connected to a polynucleotide sequence (or sequences) in such a way as to place transcription of the polynucleotide sequence under the influence or control of the promoter or promoter control element. Two DNA sequences (such as a polynucleotide to be transcribed and a promoter sequence linked to the 5' end of the polynucleotide to be transcribed) are said to be operably linked if induction of promoter function results in the transcription of mRNA encoding the polynucleotide and if the nature of the linkage between the two DNA sequences does not (1) result in the introduction of a frame-shift mutation, (2) interfere with the ability of the promoter sequence to direct the expression of the protein, antisense RNA, RNAi or ribozyme, or (3) interfere with the ability of the DNA template to be transcribed. Thus, a promoter sequence would be operably linked to a polynucleotide sequence if the promoter was capable of effecting transcription of that polynucleotide sequence.

Percentage of sequence identity As used herein, the term "percent sequence identity" refers to the degree of identity between any given query sequence and a subject sequence. A subject sequence typically has a length that is from about 80 percent to 250 percent of the length of the query sequence, e.g., 82, 85, 87, 89, 90, 93, 95, 97, 99, 100, 105, 110, 115, or 120, 130, 140, 150, 160, 170, 180, 190, 200, 210, 220, 230, 240, or 250 percent of the length of the query sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment). Chenna et al. (2003) *Nucleic Acids Res*. 31(13):3497-500.

ClustalW calculates the best match between a query and one or more subject sequences, and aligns them so that identities, similarities and differences can be determined Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For an alignment of multiple nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher website and at the European Bioinformatics Institute website on the World Wide Web.

To determine a percent identity for polypeptide or nucleic acid sequences between a query and a subject sequence, the sequences are aligned using Clustal W and the number of identical matches in the alignment is divided by the query length, and the result is multiplied by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Plant Promoter: A "plant promoter" is a promoter capable of initiating transcription in plant cells and can modulate transcription of a polynucleotide. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter known to those of skill in the art.

Plant Tissue: The term "plant tissue" includes differentiated and undifferentiated tissues or plants, including but not limited to roots, stems, shoots, rhizomes, cotyledons, epicotyl, hypocotyl, leaves, pollen, seeds, gall tissue and various forms of cells in culture such as single cells, protoplast, embryos, and callus tissue. The plant tissue may be in plants or in organ, tissue or cell culture.

Preferential Transcription: "Preferential transcription" is defined as transcription that occurs in a particular pattern of cell types or developmental times or in response to specific stimuli or combination thereof. Non-limitive examples of preferential transcription include: high transcript levels of a desired sequence in root tissues; detectable transcript levels of a desired sequence in certain cell types during embryogenesis; and low transcript levels of a desired sequence under drought conditions. Such preferential transcription can be determined by measuring initiation, rate, and/or levels of transcription.

Promoter: A "promoter" is a DNA sequence that directs the transcription of a polynucleotide. Typically a promoter is located in the 5' region of a polynucleotide to be transcribed, proximal to the transcriptional start site of such polynucleotide. More typically, promoters are defined as the region upstream of the first exon; more typically, as a region upstream of the first of multiple transcription start sites; more typically, as the region downstream of the preceding gene and upstream of the first of multiple transcription start sites; more typically, the region downstream of the polyA signal and upstream of the first of multiple transcription start sites; even more typically, about 3,000 nucleotides upstream of the ATG of the first exon; even more typically, 2,000 nucleotides upstream of the first of multiple transcription start sites. The promoters of the document comprise at least a core promoter as defined above. Frequently promoters are capable of directing transcription of genes located on each of the complementary DNA strands that are 3' to the promoter. Stated differently, many promoters exhibit bidirectionality and can direct transcription of a downstream gene when present in either orientation (i.e. 5' to 3' or 3' to 5' relative to the coding region of the gene). Additionally, the promoter may also include at least one control element such as an upstream element. Such elements include UARs and optionally, other DNA sequences that affect transcription of a polynucleotide such as a synthetic upstream element.

Promoter Control Element: The term "promoter control element" as used herein describes elements that influence the activity of the promoter. Promoter control elements include transcriptional regulatory sequence determinants such as, but not limited to, enhancers, scaffold/matrix attachment regions, TATA boxes, transcription start locus control regions, UARs, URRs, other transcription factor binding sites and inverted repeats.

Public sequence: The term "public sequence," as used in the context of the instant application, refers to any sequence that has been deposited in a publicly accessible database prior to the filing date of the present application. This term encompasses both amino acid and nucleotide sequences. Such sequences are publicly accessible, for example, on the BLAST databases on the NCBI FTP web site (accessible via the internet). The database at the NCBI FTP site utilizes "gi" numbers assigned by NCBI as a unique identifier for each sequence in the databases, thereby providing a non-redundant database for sequence from various databases, including GenBank, EMBL, DBBJ (DNA Database of Japan) and PDB (Brookhaven Protein Data Bank).

Regulatory Regions: The term "regulatory region" refers to nucleotide sequences that, when operably linked to a sequence, influence transcription initiation or translation initiation or transcription termination of said sequence and the rate of said processes, and/or stability and/or mobility of a transcription or translation product. As used herein, the term "operably linked" refers to positioning of a regulatory region and said sequence to enable said influence. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Regulatory regions can be classified in two categories, promoters and other regulatory regions.

Regulatory Sequence: The term "regulatory sequence," as used in the current document, refers to any nucleotide sequence that influences transcription or translation initiation and rate, or stability and/or mobility of a transcript or polypeptide product. Regulatory sequences include, but are not limited to, promoters, promoter control elements, protein binding sequences, 5' and 3' UTRs, transcriptional start sites, termination sequences, polyadenylation sequences, introns, certain sequences within amino acid coding sequences such as secretory signals, protease cleavage sites, etc.

Specific Promoters: In the context of the current document, "specific promoters" refers to a subset of promoters that have a high preference for modulating transcript levels in a specific tissue, or organ or cell and/or at a specific time during development of an organism. By "high preference" is meant at least 3-fold, preferably 5-fold, more preferably at least 10-fold still more preferably at least 20-fold, 50-fold or 100-fold increase in transcript levels under the specific condition over the transcription under any other reference condition considered. Typical examples of temporal and/or tissue or organ specific promoters of plant origin that can be used with the polynucleotides of the present document, are: PTA29, a promoter which is capable of driving gene transcription specifically in tapetum and only during another development (Koltonow et al. (1990) Plant Cell 2:1201; RCc2 and RCc3, promoters that direct root-specific gene transcription in rice (Xu et al. (1995) Plant Mol. Biol. 27:237; TobRB27, a root-specific promoter from tobacco (Yamamoto et al. (1991) Plant Cell 3:371). Examples of tissue-specific promoters under developmental control include promoters that initiate transcription only in certain tissues or organs, such as root, ovule, fruit, seeds, or flowers. Other specific promoters include those from genes encoding seed storage proteins or the lipid body membrane protein, oleosin. A few root-specific promoters are noted above. See also "Preferential transcription."

Stringency: "Stringency," as used herein is a function of nucleic acid molecule probe length, nucleic acid molecule probe composition (G+C content), salt concentration, organic solvent concentration and temperature of hybridization and/or wash conditions. Stringency is typically measured by the parameter $T_m$, which is the temperature at which 50% of the complementary nucleic acid molecules in the hybridization assay are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship between hybridization conditions and $T_m$ (in ° C.) is expressed in the mathematical equation:

$$T_m = 81.5 - 16.6(\log 10[Na^+]) + 0.41(\% \; G+C) - (600/N) \quad (I)$$

where N is the number of nucleotides of the nucleic acid molecule probe. This equation works well for probes 14 to 70 nucleotides in length that are identical to the target sequence. The equation below, for $T_m$ of DNA-DNA hybrids, is useful for probes having lengths in the range of 50 to greater than 500 nucleotides, and for conditions that include an organic solvent (formamide):

$$T_m = 81.5 + 16.6 \log\{[Na^+]/(1+0.7[Na^+])\} + 0.41(\% \; G+C) - 500/L \; 0.63(\% \text{ formamide}) \quad (II)$$

where L represents the number of nucleotides in the probe in the hybrid (21). The $T_m$ of Equation II is affected by the nature of the hybrid: for DNA-RNA hybrids, $T_m$ is 10-15° C. higher than calculated; for RNA-RNA hybrids, $T_m$ is 20-25° C. higher. Because the $T_m$ decreases about 1° C. for each 1% decrease in homology when a long probe is used (Frischauf et al. (1983) J. Mol Biol, 170: 827-842), stringency conditions can be adjusted to favor detection of identical genes or related family members.

Equation II is derived assuming the reaction is at equilibrium. Therefore, hybridizations according to the present document are most preferably performed under conditions of probe excess and allowing sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction, or after hybridization has occurred, by altering the salt and temperature conditions of the wash solutions. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

$T_0$: The term "$T_0$" refers to the whole plant, explant or callus tissue, inoculated with the transformation medium.

$T_1$: The term $T_1$ refers to either the progeny of the $T_0$ plant, in the case of whole-plant transformation, or the regenerated seedling in the case of explant or callous tissue transformation.

$T_2$: The term $T_2$ refers to the progeny of the $T_1$ plant. $T_2$ progeny are the result of self-fertilization or cross-pollination of a $T_1$ plant.

$T_3$: The term $T_3$ refers to second generation progeny of the plant that is the direct result of a transformation experiment. $T_3$ progeny are the result of self-fertilization or cross-pollination of a $T_2$ plant.

TATA to start: "TATA to start" shall mean the distance, in number of nucleotides, between the primary TATA motif and the start of transcription.

Transgenic plant: A "transgenic plant" is a plant having one or more plant cells that contain at least one exogenous polynucleotide introduced by recombinant nucleic acid methods.

Translational start site: In the context of the present document, a "translational start site" is usually an ATG or AUG in a transcript, often the first ATG or AUG. A single protein encoding transcript, however, may have multiple translational start sites.

Transcription start site: "Transcription start site" is used in the current document to describe the point at which transcription is initiated. This point is typically located about 25 nucleotides downstream from a TFIID binding site, such as a TATA box. Transcription can initiate at one or more sites within the gene, and a single polynucleotide to be transcribed may have multiple transcriptional start sites, some of which may be specific for transcription in a particular cell-type or tissue or organ. "+1" is stated relative to the transcription start site and indicates the first nucleotide in a transcript.

Upstream Activating Region (UAR): An "Upstream Activating Region" or "UAR" is a position or orientation dependent nucleic acid element that primarily directs tissue, organ, cell type, or environmental regulation of transcript level, usually by affecting the rate of transcription initiation. Corresponding DNA elements that have a transcription inhibitory effect are called herein "Upstream Repressor Regions" or "URR"s. The essential activity of these elements is to bind a protein factor. Such binding can be assayed by methods described below. The binding is typically in a manner that influences the steady state level of a transcript in a cell or in vitro transcription extract.

Untranslated region (UTR): Untranslated region (UTR): A "UTR" is any contiguous series of nucleotide bases that is transcribed, but is not translated. A 5' UTR lies between the start site of the transcript and the translation initiation codon (ATG codon) and includes the +1 nucleotide of the messenger RNA or cDNA. Alternately, 5' UTR can be synthetically produced or manipulated DNA elements. A "plant 5' UTR" can be a native or non-native 5' UTR that is functional in plant cells. A 5' UTR can be used as a 5' regulatory element for modulating expression of an operably linked transcribable polynucleotide molecule. For example, 5' UTRs derived from heat shock protein genes have been demonstrated to enhance gene expression in plants (see for example, U.S. Pat. No. 5,659,122 and U.S. Pat. No. 5,362,865, all of which are incorporated herein by reference). Examples of 5' UTRs include those shown in SEQ ID NOs:1-7, 9-12, 16-18. A 3' UTR lies between the translation termination codon and the end of the transcript. UTRs can have particular functions such as increasing mRNA message stability or translation attenuation. Examples of 3' UTRs include, but are not limited to polyadenylation signals and transcription termination sequences.

2. Use of the Promoters

The promoters and promoter control elements of this document are capable of modulating transcription. Such promoters and promoter control elements can be used in combination with native or heterologous promoter fragments, control elements or other regulatory sequences to modulate transcription and/or translation.

Specifically, promoters and control elements of the document can be used to modulate transcription of a desired polynucleotide, which includes without limitation:
a) antisense;
b) ribozymes;
c) coding sequences; or
d) fragments thereof.

The promoter also can modulate transcription in a host genome in cis- or in trans-.

In an organism, such as a plant, the promoters and promoter control elements of the instant document are useful to produce preferential transcription which results in a desired pattern of transcript levels in a particular cells, tissues, or organs, or under particular conditions.

3. Identifying and Isolating Promoter Sequences

The promoters and promoter control elements of the present document are presented in the Promoter Reports of the Tables and were identified from *Sorghum bicolor*. Isolation from genomic libraries of polynucleotides comprising the sequences of the promoters and promoter control elements of the present document is possible using known techniques. For example, polymerase chain reaction (PCR) can amplify the desired polynucleotides utilizing primers designed from SEQ ID NOs: 1-18. Polynucleotide libraries comprising genomic sequences can be constructed according to Sambrook et al., *Molecular Cloning: A Laboratory Manual*, $2^{nd}$ Ed. (1989) Cold Spring Harbor Press, Cold Spring Harbor, N.Y.), for example.

Other procedures for isolating polynucleotides comprising the promoter sequences of the document include, without limitation, tail-PCR, and 5' rapid amplification of cDNA ends (RACE). See, for tail-PCR, for example, Liu et al. (1995) *Plant J* 8(3): 457-463; Liu et al. (1995) *Genomics* 25: 674-681; Liu et al. (1993) *Nucl. Acids Res.* 21(14): 3333-3334; and Zoe et al. (1999) *BioTechniques* 27(2: 240-248; for RACE, see, for example, PCR *Protocols: A Guide to Methods and Applications*, (1990) Academic Press, Inc.

In addition, the promoters and promoter control elements described in the Promoter Reports in the Tables (SEQ. ID. Nos. 1-18) can be chemically synthesized according to techniques in common use. See, for example, Beaucage et al. (1981) *Tet. Lett.* 22: 1859 and U.S. Pat. No. 4,668,777. Such chemical oligonucleotide synthesis can be carried out using commercially available devices, such as, Biosearch 4600 or 8600 DNA synthesizer, by Applied Biosystems, a division of Perkin-Elmer Corp., Foster City, Calif., USA; and Expedite by Perceptive Biosystems, Framingham, Mass., USA.

Included in the present document are promoters exhibiting nucleotide sequence identity to SEQ. ID. Nos. 1-18. In particular, promoters of this document can exhibit at least 80% sequence identity (e.g., at least 85%, at least 90%, at least 95%, 96%, 97%, 98% or 99% sequence identity) compared to the nucleotide sequence set forth in any one of SEQ. ID. Nos. 1-18. Sequence identity can be calculated by the algorithms and computers programs described above. Furthermore, promoters described herein also can be a fragment of any one of SEQ ID NO:1-18 as long as the fragment retains the ability to direct transcription of a polynucleotide. Suitable fragments can be, for example at least 80% (e.g., at least 85, 90, 95, 96, 97, 98, or 99%) of the length of the nucleotide sequence set forth in any one of SEQ ID NOs:1-18. For example, a regulatory region can be a fragment of anyone of SEQ ID NOs:1-18 that is 100, 200, 300, 400, 500, 600, 700, 800, 900, 1000, 1100, 1200, 1300, 1400, 1500, 1600, 1700, 1800, 1900, 2000, 2100, 2200, or 2400 nucleotides in length that retains the ability to direct expression of an operably linked nucleic acid.

A regulatory region can contain conserved regulatory motifs. Such a regulatory region can be have a nucleotide sequence set forth in anyone of SEQ ID NOs:1-18, or a regulatory region having a nucleotide sequence that deviates from that set forth in SEQ ID NOs:1-18, while retaining the ability to direct expression of an operably linked nucleic acid. For example, a regulatory region can contain a CAAT box or a TATA box. A CAAT box is a conserved nucleotide sequence involved in initiation of transcription. A CAAT box functions as a recognition and binding site for regulatory proteins called transcription factors. A TATA box is another conserved nucleotide sequence involved in transcription initiation. A TATA box seems to be important in determining accurately the position at which transcription is initiated.

Other conserved regulatory motifs can be identified using methods known in the art. For example, a regulatory region can be analyzed using the PLACE (PLAnt Cis-acting regulatory DNA Elements) Web Signal Scan program on the world wide web at dna.affrc.gojp/PLACE/signalscan.html. See, Higo et al., *Nucleic Acids Research*, 27(1):297-300 (1999); and Prestridge, *CABIOS*, 7:203-206 (1991). Examples of conserved regulatory motifs can be found in the PLACE database on the world wide web at dna.affrc.go.jp/PLACE/. See, Higo et al., supra.

A regulatory region having a nucleotide sequence set forth in anyone of SEQ ID NOs:1-18, or a regulatory region having a nucleotide sequence that deviates from that set forth in SEQ ID NOs:1-18, while retaining the ability to direct expression of an operably linked nucleic acid, can contain one or more conserved regulatory motifs, which can be found in the PLACE database. For example, a regulatory region can contain an ABRE motif having the consensus sequence ACGTG. See, Simpson et al., *Plant J.* 33: 259-270 (2003); Nakashima et al., *Plant Mol. Biol.* 60:51-68 (2006). A regulatory region can contain an ABREATRD22 motif having the consensus sequence RYACGTGGYR (SEQ ID NO:19). See, Iwasaki et al., *Mol Gen Genet.* 247:391-398 (1995); Bray, *Trends Plant Sci.* 2:48-54 (1997); Busk and Pages, *Plant Mol Biol* 37:425-435 (1998). A regulatory region can contain an ABRERATCAL motif having the consensus sequence MACGYGB. See, Kaplan et al., *Plant Cell.* 18:2733-2748 (2006). A regulatory region can contain an ABREZMRAB28 motif having the consensus sequence CCACGTGG. See, Suzuki et al., *Plant Physiol.* 139: 437-447 (2005); Busk and Pages, *Plant Mol Biol* 37:425-435 (1998); Alonso-Blanco et al., *Plant Physiology* 139: 1304-1312 (2005); Guan et al., *Plant J* 22: 87-95 (2000); Benedict et al., *Plant Cell Environ.* 29:1259-1272 (2006); Jaglo-Ottosen et al., *Science* 1998 3: 104-106 (1998); and Gilmour et al., *Plant J* 16: 433-442 (1998). A regulatory region can contain an ACGTABREMOTIFA2OSEM motif having the consensus sequence ACGTGKC. See, Hattori et al., *Plant Cell Physiol* 43: 136-140 (2002); and Narusaka et al., *Plant J.* 34: 137-148 (2003). A regulatory region can contain an ACIIPVPAL2 motif having the consensus sequence CCAC-CAACCCCC (SEQ ID NO:20). See, Patzlaff et al., *Plant Mol. Biol.* 53:597-608 (2003); Hatton et al., *Plant J* 7:859-876 (1995); and Gomez-Maldonado et al., *Plant J.* 39:513-526 (2004). A regulatory region can contain an AGCBOX-NPGLB motif having the consensus sequence TATTCT. See, Hart et al., *Plant Mol Biol* 21:121-131 (1993); Fujimoto et al., *Plant Cell* 12:393-404 (2000); Sato et al., *Plant Cell Physiol* 37: 249-255 (1996); Ohme-Takagi et al., *Plant Cell Physiol* 41: 1187-1192 (2000); Rushton et al., *Plant Cell* 14: 749-762 (2002); Cheong et al., *Plant Physiol.* 132: 1961-1972 (2003); and Zhang et al., *Planta.* 220: 262-270 (2004). A regulatory region can contain an AMYBOX1 motif having the consensus sequence TAACARA. See, Huang et al., *Plant Mol Biol* 14:655-668 (1990). A regulatory region can contain an ARE1 motif having the consensus sequence RGT-GACNNNGC (SEQ ID NO:21). See, Rushmore et al., *J Biol Chem* 266:11632-11639 (1991). A regulatory region can contain an ATHB1ATCONSENSUS motif having the consensus sequence CAATWATTG. See, Sessa et al., *EMBO J.* 12:3507-3517 (1993). A regulatory region can contain an ATHB6COREAT motif having the consensus sequence CAATTATTA. See, Himmelbach et al., *EMBO J.* 21:3029-3038 (2002). A regulatory region can contain an AUXRETGA2GMGH3 motif having the consensus sequence TGACGTAA. See, Liu et al., *Plant Cell* 6:645-657 (1994); Liu et al., *Plant Physiol* 115:397-407 (1997); and Guilfoyle et al., *Plant Physiol* 118: 341-347 (1998). A regulatory region can contain a BOXIIPCCHS motif having the consensus sequence ACGTGGC. See, Block et al., *Proc Natl Acad Sci USA* 87:5387-5391 (1990); Terzaghi and Cashmore, *Annu Rev Plant Physiol Plant Mol Biol* 46:445-474 (1995); and Nakashima et al., *Plant Mol. Biol.* 60: 51-68 (2006). A regulatory region can contain a CAATBOX1 motif having the consensus sequence CCAAT. See, Shirsat et al., *Mol Gen Genet.* 215:326-331 (1989). A regulatory region can contain a CACGCAATGMGH3 motif having the consensus sequence CACGCAAT. See, Ulmasov et al., *Plant Cell* 7: 1611-1623 (1995). A regulatory region can contain a CARGCW8GAT motif having the consensus sequence CWWWWWWWWG (SEQ ID NO:22). See, Tang and Perry, *J Biol. Chem.* 278:28154-28159 (2003); Folter and Angenent, *Trends Plant Sci.* 11:224-231 (2006). A regulatory region can contain a CCA1ATLHCB1 motif having the consensus sequence AAMAATCT. See, Wang et al., *Plant Cell* 9:491-507 (1997). A regulatory region can contain a CEREGLUBOX2PSLEGA motif having the consensus sequence TGAAAACT. See, Shirsat et al., supra. A regulatory region can contain an E2FAT motif having the consensus sequence TYTCCCGCC. See, Ramirez-Parra et al., *Plant J.* 33: 801-811 (2003). A regulatory region can contain an E2FCONSENSUS motif having the consensus sequence WTTSSCSS. See, Vandepoele et al., *Plant Physiol.* 139: 316-328 (2005). A regulatory region can contain an ERELEE4 motif having the consensus sequence AWT-TCAAA. See, Itzhaki et al., *Proc Natl Acad Sci USA* 91:8925-8929 (1994); Montgomery et al., *Proc Natl Acad Sci USA* 90:5939-5943 (1993); Tapia et al., *Plant Physiol.* 138:2075-2086 (2005); and Rawat et al., *Plant Mol. Biol.* 57: 629-643 (2005). A regulatory region can contain a GADOWNAT motif having the consensus sequence ACGT-GTC. See, Ogawa et al., *Plant Cell* 15: 1591-1604 (2003); and Nakashima et al., *Plant Mol. Biol.* 60: 51-68 (2006). A regulatory region can contain a GARE1OSREP1 motif having the consensus sequence TAACAGA. See, Sutoh and Yamauchi, *Plant J.* 34: 636-645 (2003). A regulatory region can contain a GAREAT motif having the consensus sequence TAACAAR. See, Ogawa et al., *Plant Cell* 15: 1591-1604 (2003). A regulatory region can contain an IBOXCORENT motif having the consensus sequence GATAAGR. See, Martinez-Hernandez et al., *Plant Physiol.* 128:1223-1233 (2002). A regulatory region can contain an INRNTPSADB motif having the consensus sequence YTCANTYY. See, Nakamura et al., *Plant J* 29: 1-10 (2002). A regulatory region can contain a LRENPCABE motif having the consensus sequence ACGTGGCA. See, Castresana et al., *EMBO J.* 7:1929-1936 (1988). A regulatory region can contain a MARTBOX motif having the consensus sequence TTWTWTTWTT (SEQ ID NO:23). See, Gasser et al., *Int Rev Cyto* 119:57-96 (1989). A regulatory region can contain a MYBGAHV motif having the consensus sequence TAACAAA. See, Gubler et al., *Plant Cell* 7:1879-1891 (1995); Morita et al., *FEBS Lett* 423:81-85 (1998); Gubler et al., *Plant J.* 17:1-9 (1999). A regulatory region can contain a MYBPLANT motif having the consensus sequence MACCWAMC. See, Sablowski et al., *EMBO J.* 13:128-137 (1994); Tamagnone et al., *Plant Cell* 10: 135-154 (1998). A regulatory region can contain a NRRB-NEXTA motif having the consensus sequence TAGTGGAT. See, Elliott and Shirsat, *Plant Mol Biol* 37:675-687 (1998). A regulatory region can contain a P1BS motif having the consensus sequence GNATATNC. See, Rubio et al., *Genes Dev.* 15: 2122-2133. (2001); Shunmann et al., *J Exp Bot.* 55: 855-865. (2004); and Shunmann et al., *Plant Physiol.* 136: 4205-4214 (2004). A regulatory region can contain a PRECONSCRHSP70A motif having the consensus sequence SCGAYNRNNNNNNNNNNNNNNNHD (SEQ ID NO:24). See, von Gromoff et al., *Nucleic Acids Res.* 34:4767-4779 (2006). A regulatory region can contain a ROOTMOTIFTAPDX1 motif having the consensus sequence ATATT. See, Elmayan and Tepfer, *Transgenic Res* 4:388-396 (1995). A regulatory region can contain a RYREPEATGMGY2 motif having the consensus sequence CATGCAT. See, Lelievre et al., *Plant Physiol* 98:387-391 (1992). A regulatory region can contain a RYREPEATVFLEB4 motif having the consensus sequence CATGCATG. See, Curaba et al., *Plant Physiol.* 136: 3660-3669 (2004); and Nag et al., *Plant Mol. Biol.* 59: 821-838 (2005). A regulatory region can contain a SBOXATRBCS motif having the consensus sequence CACCTCCA. See, Acevedo-Hernandez et al., *Plant J.* 43:506-519 (2005). A regulatory region can contain a SP8BFIBSP8BIB motif having the consensus sequence TACTATT. See, Ishiguro and Nakamura, *Plant Mol Biol* 18:97-108 (1992); Ishiguro and Nakamura, *Mol Gen Genet.* 244: 563-571 (1994). A regulatory region can contain a TATABOX1, TATABOX2, or TATABOX4 motif having the consensus sequence CTATAAATAC (SEQ ID NO:25), TATAAAT, and TATATAA, respectively. See, Grace et al., *J Biol. Chem.* 279:8102-8110 (2004); and Shirsat et al., supra. A regulatory region can contain a TATABOXOSPAL motif having the consensus sequence TATTTAA. See, Zhu et al., *Plant Cell* 14: 795-803 (2002). A regulatory region can contain a TATCCAYMOTIFOSRAMY3D motif having the consensus sequence TATCCAY. See, Toyofuku et al., *FEBS Lett* 428:275-280 (1998); and Rubio-Somoza et al., Plant J. 47: 269-281 (2006). A regulatory region can contain a TE2F2NTPCNA motif having the consensus sequence ATTCCCGC. See, Kosugi and Ohashi, *Plant J* 29: 45-59 (2002). A regulatory region can contain a TRANSINITMONOCOTS motif having the consensus sequence RMNAUGGC. See, Joshi et al., *Plant Mol Biol* 35:993-1001 (1997). A regulatory region can contain a UP2ATMSD motif having the consensus sequence AAACCCTA. See, Tatematsu et al., *Plant Physiol.* 138: 757-766 (2005). A regulatory region can contain an UPRMOTIFIIAT motif having the consensus sequence CCNNNNNNNNNNNNC-CACG (SEQ ID NO:26). See, Martinez and Chrispeels, *Plant Cell.* 15:561-576 (2003); and Oh et al., *Biochem Biophys Res Commun.* 301:225-230 (2003).

In some embodiments, a regulatory region has a nucleotide sequence with 90% or greater sequence identity to the polynucleotide sequence set forth in SEQ ID NO:1 or a fragment thereof, wherein the nucleic acid contains a GARE1OSREP1, ACIIPVPAL2, ABRERATCAL, and TATABOX motif. The GARE1OSREP1 motif can be the motif at nucleotides 80 to 86 or nucleotides 122 to 128 of SEQ ID NO:1 or a GARE1OSREP1 motif heterologous to those in SEQ ID NO:1. The ACIIPVPAL2 motif can be the motif at nucleotides 201 to 212 of SEQ ID NO:1 or an ACIIPVPAL2 motif heterologous to that in SEQ ID NO:1. The ABRERATCAL motif can be the motif at nucleotides 327 to 333 of SEQ ID NO:1 or an ABRERATCAL motif heterologous to that in SEQ ID NO:1. The TATABOX can be the motif at nucleotides 461 to 467 of SEQ ID NO:1 or a TATABOX heterologous to that in SEQ ID NO:1. In some cases, such a regulatory region can also include a 5' UTR. The 5' UTR can be the 5' UTR at nucleotides 501 to 561 or 1069 to 1100 of SEQ ID NO:1 or can be a heterologous UTR.

In some embodiments, a regulatory region has a nucleotide sequence with 90% or greater sequence identity to the polynucleotide sequence set forth in SEQ ID NO:2 or a fragment thereof, wherein the nucleic acid contains an AUXRETGA2GMGH3, ACGTABREMOTIFA2OSEM, TATCCAYMOTIFOSRAMY3D, AMYBOX1, and GAREAT motif. The AUXRETGA2GMGH3 motif can be the motif at nucleotides 24 to 32 of SEQ ID NO:2 or an AUXRETGA2GMGH3 motif heterologous to that in SEQ ID NO:2. The ACGTABREMOTIFA2OSEM motif can be the motif at nucleotides 24 to 30 of SEQ ID NO:2 or an ACGTABREMOTIFA2OSEM motif heterologous to that in SEQ ID NO:2. The TATCCAYMOTIFOSRAMY3D motif can be the motif at nucleotides 52 to 58 of SEQ ID NO:2 or a TATCCAYMOTIFOSRAMY3D motif heterologous to that in SEQ ID NO:2. The AMYBOX1 motif can be the motif at nucleotides 135 to 141 of SEQ ID NO:2 or an AMYBOX1 motif heterologous to that in SEQ ID NO:2. The GAREAT motif can be the motif at nucleotides 135 to 141 of SEQ ID NO:2 or a GAREAT motif heterologous to that in SEQ ID NO:1. In some cases, such a regulatory region can also include a 5' UTR. The 5' UTR can be the 5' UTR at nucleotides 140 to 219 of SEQ ID NO:2 or can be a heterologous UTR.

In some embodiments, a regulatory region has a nucleotide sequence with 90% or greater sequence identity to the polynucleotide sequence set forth in SEQ ID NO:3 or a fragment thereof, wherein the nucleic acid contains an ARE1, SBOXATRBCS, TE2F2NTPCNA, GADOWNAT, ACGTABREMOTIFA2OSEM, and TATABOX motif. The ARE1 motif can be the motif at nucleotides 124 to 134 of SEQ ID NO:3 or an ARE1 motif heterologous to that in SEQ ID NO:3. The SBOXATRBCS motif can be the motif at nucleotides 202 to 209 of SEQ ID NO:3 or a SBOXATRBCS motif heterologous to that in SEQ ID NO:3. The TE2F2NTPCNA motif can be the motif at nucleotides 240 to 247 of SEQ ID NO:3 or a TE2F2NTPCNA motif heterologous to that in SEQ ID NO:3. The GADOWNAT motif can be the motif at nucleotides 308 to 314 of SEQ ID NO:3 or a GADOWNAT motif heterologous to that in SEQ ID NO:3. The ACGTABREMOTIFA2OSEM motif can be the motif at nucleotides 308 to 314 of SEQ ID NO:3 or an ACGTABREMOTIFA2OSEM motif heterologous to that in SEQ ID NO:3. The TATABOX can be the motif at nucleotides 280 to 286 of SEQ ID NO:3 or a TATABOX heterologous to that in SEQ ID NO:3. In some cases, such a regulatory region can also include a 5' UTR. The 5' UTR can be the 5' UTR at nucleotides 311 to 400 of SEQ ID NO:3 or can be a heterologous UTR.

In some embodiments, a regulatory region has a nucleotide sequence with 90% or greater sequence identity to the polynucleotide sequence set forth in SEQ ID NO:4 or a fragment thereof, wherein the nucleic acid contains a ROOTMOTIFTAPDX1, RYREPEATVFLEB4, and TATABOX motif. The ROOTMOTIFTAPDX1 motif can be the motif at nucleotides 179 to 183 or 182 to 186 of SEQ ID NO:4 or a ROOTMOTIFTAPDX1 motif heterologous to those in SEQ ID NO:4. The RYREPEATVFLEB4 motif can be the motif at nucleotides 225 to 232 or 229 to 236 of SEQ ID NO:4 or a RYREPEATVFLEB4 motif heterologous to those in SEQ ID NO:4. The TATABOX can be the motif at nucleotides 292 to 299 of SEQ ID NO:4 or a TATABOX motif heterologous to that in SEQ ID NO:4. In some cases, such a regulatory region can also include a 5' UTR. The 5' UTR can be the 5' UTR at nucleotides 324 to 420 of SEQ ID NO:4 or can be a heterologous UTR.

In some embodiments, a regulatory region has a nucleotide sequence with 90% or greater sequence identity to the polynucleotide sequence set forth in SEQ ID NO:5 or a fragment thereof, wherein the nucleic acid contains a CARGCW8GAT, INRNTPSADB, and TATABOX2motif. The CARGCW8GAT motif can be the motif at nucleotides 415 to 424 of SEQ ID NO:5 or a CARGCW8GAT motif heterologous to that in SEQ ID NO:5. The INRNTPSADB motif can be the motif at nucleotides 580 to 587 of SEQ ID NO:5 or an INRNTPSADB motif heterologous to that in SEQ ID NO:5. The TATABOX2 motif can be the motif at nucleotides 417 to 423 of SEQ ID NO:5 or a TATABOX2 motif heterologous to that in SEQ ID NO:5. In some cases, such a regulatory region can also include a 5' UTR. The 5' UTR can be the 5' UTR at nucleotides 630 to 759 of SEQ ID NO:5 or can be a heterologous UTR.

In some embodiments, a regulatory region has a nucleotide sequence with 90% or greater sequence identity to the polynucleotide sequence set forth in SEQ ID NO:6 or a fragment thereof, wherein the nucleic acid contains a MARTBOX, RYREPEATVFLEB4, NRRBNEXTA, TRANSINITMONOCOTS, TATABOXOSPAL, and P1BS motif. The MARTBOX motif can be the motif at nucleotides 453 to 462 of SEQ ID NO:6 or a MARTBOX motif heterologous to that in SEQ ID NO:6. The RYREPEATVFLEB4 motif can be the motif at nucleotides 480 to 487 or 832 to 839 of SEQ ID NO:6 or a RYREPEATVFLEB4 motif heterologous to those in SEQ ID NO:6. The NRRBNEXTA motif can be the motif at nucleotides 693 to 700 of SEQ ID NO:6 or a NRRBNEXTA motif heterologous to that in SEQ ID NO:6. The TRANSINITMONOCOTS motif can be the motif at nucleotides 853 to 860 of SEQ ID NO:6 or a TRANSINITMONOCOTS motif heterologous to that in SEQ ID NO:6. The TATABOXOSPAL motif can be the motif at nucleotides 884 to 890 of SEQ ID NO:6 or a TATABOXOSPAL motif heterologous to that in SEQ ID NO:6. The P1BS motif can be the motif at nucleotides 907 to 914 of SEQ ID NO:6 or a P1BS motif heterologous to that in SEQ ID NO:6. In some cases, such a regulatory region can also include a 5' UTR. The 5' UTR can be the 5' UTR at nucleotides 914 to 1020 of SEQ ID NO:6 or can be a heterologous UTR.

In some embodiments, a regulatory region has a nucleotide sequence with 90% or greater sequence identity to the polynucleotide sequence set forth in SEQ ID NO:7 or a fragment thereof, wherein the nucleic acid contains a CARGCW8GAT, P1BS, and TATABOX motif. The CARGCW8GAT motif can be the motif at nucleotides 294 to 303 or 394 to 403 of SEQ ID NO:7 or a CARGCW8GAT motif heterologous to those in SEQ ID NO:7. The P1BS motif can be the motif at nucleotides 666 to 673 of SEQ ID NO:7 or a P1BS motif heterologous to that in SEQ ID NO:7. The TATABOX can be the motif at nucleotides 883 to 891 of SEQ ID NO:7 or a TATABOX motif heterologous to that in SEQ ID NO:7. In some cases, such a regulatory region can also include a 5' UTR. The 5' UTR can be the 5' UTR at nucleotides 917 to 1075 of SEQ ID NO:7 or can be a heterologous UTR.

In some embodiments, a regulatory region has a nucleotide sequence with 90% or greater sequence identity to the polynucleotide sequence set forth in SEQ ID NO:8 or a fragment thereof, wherein the nucleic acid contains a ROOTMOTIFTAPDX1, ATHB6COREAT, TATABOX2, and UP2ATMSD motif. The ROOTMOTIFTAPDX1 motif can be the motif at nucleotides 120 to 124, 392 to 396, or 522 to 526 of SEQ ID NO:8 or a ROOTMOTIFTAPDX1 motif heterologous to those in SEQ ID NO:8. The ATHB6COREAT motif can be the motif at nucleotides 779 to 787 of SEQ ID NO:8 or an ATHB6COREAT motif heterologous to that in SEQ ID NO:8. The TATABOX2 motif can be the motif at nucleotides 813 to 819 of SEQ ID NO:8 or a TATABOX2 motif heterologous to that in SEQ ID NO:8. The UP2ATMSD motif can be the motif at nucleotides 951 to 958 of SEQ ID NO:8 or an UP2ATMSD motif heterologous to that in SEQ ID NO:8. In some cases, such a regulatory region can also include a 5' UTR.

In some embodiments, a regulatory region has a nucleotide sequence with 90% or greater sequence identity to the polynucleotide sequence set forth in SEQ ID NO:9 or a fragment thereof, wherein the nucleic acid contains a PRECONSCRHSP70A, IBOXCORENT, AGCBOXNPGLB, UP2ATMSD, and TATABOX4 motif. The PRECONSCRHSP70A motif can be the motif at nucleotides 22 to 45, 38 to 61, or 60 to 83 of SEQ ID NO:9 or a PRECONSCRHSP70A motif heterologous to those in SEQ ID NO:9. The IBOXCORENT motif can be the motif at nucleotides 153 to 159 of SEQ ID NO:9 or an IBOXCORENT motif heterologous to that in SEQ ID NO:9. The AGCBOXNPGLB motif can be the motif at nucleotides 216 to 222 or 306 to 312 of SEQ ID NO:9 or an AGCBOXNPGLB motif heterologous to those in SEQ ID NO:9. The UP2ATMSD motif can be the motif at nucleotides 306 to 312 of SEQ ID NO:9 or an UP2ATMSD motif heterologous to that in SEQ ID NO:9. The TATABOX4 motif can be the motif at nucleotides 359 to 365 of SEQ ID NO:9 or a TATABOX4 motif heterologous to that in SEQ ID NO:9. In some cases, such a regulatory region can also include a 5' UTR. The 5' UTR can be the 5' UTR at nucleotides 390 to 1428 of SEQ ID NO:9 or can be a heterologous UTR.

In some embodiments, a regulatory region has a nucleotide sequence with 90% or greater sequence identity to the polynucleotide sequence set forth in SEQ ID NO:10 or a fragment thereof, wherein the nucleic acid contains an IBOXCORENT, ERELEE4, ABREATRD22, P1BS, and TATABOX motif. The IBOXCORENT motif can be the motif at nucleotides 1472 to 1478 of SEQ ID NO:10 or an IBOXCORENT motif heterologous to that in SEQ ID NO:10. The ERELEE4 motif can be the motif at nucleotides 1565 to 1572 or 2270 to 2277 of SEQ ID NO:10 or an ERELEE4 motif heterologous to those in SEQ ID NO:10. The ABREATRD22 motif can be the motif at nucleotides 2193 to 2202 of SEQ ID NO:10 or an ABREATRD22 motif heterologous to that in SEQ ID NO:10. The P1BS motif can be the motif at nucleotides 2353 to 2360 of SEQ ID NO:10 or a P1BS motif heterologous to that in SEQ ID NO:10. The TATABOX motif can be the motif at nucleotides 2391 to 2396 of SEQ ID NO:10 or a TATABOX motif heterologous to that in SEQ ID NO:10. In some cases, such a regulatory region can also include a 5' UTR. The 5' UTR can be the 5' UTR at nucleotides 2426 to 2485 of SEQ ID NO:10 or can be a heterologous UTR.

In some embodiments, a regulatory region has a nucleotide sequence with 90% or greater sequence identity to the polynucleotide sequence set forth in SEQ ID NO:11 or a fragment thereof (e.g., a fragment containing nucleotides 1 to 896 of SEQ ID NO:11), wherein the nucleic acid contains a CACGCAATGMGH3 and UPRMOTIFIIAT motif. The CACGCAATGMGH3 motif can be the motif at nucleotides 716 to 723 of SEQ ID NO:11 or a CACGCAATGMGH3 motif heterologous to that in SEQ ID NO:11. The UPRMOTIFIIAT motif can be the motif at nucleotides 770 to 788 of SEQ ID NO:11 or an UPRMOTIFIIAT motif heterologous to that in SEQ ID NO:11. In some cases, such a regulatory region can also include a 5' UTR. The 5' UTR can be the 5' UTR at nucleotides 837 to 896 of SEQ ID NO:11 or can be a heterologous UTR.

In some embodiments, a regulatory region has a nucleotide sequence with 90% or greater sequence identity to the polynucleotide sequence set forth in SEQ ID NO:12 or a fragment thereof (e.g., a fragment containing nucleotides 501 to 2000 of SEQ ID NO:12, referred to as PD3777 herein), wherein the nucleic acid contains a PRECONSCRHSP70A, ACIIPVPAL2, TATABOX4, and CAAT-box motif. The PRECONSCRHSP70A motif can be the motif at nucleotides 535 to 558 of SEQ ID NO:12 or a PRECONSCRHSP70A motif heterologous to that in SEQ ID NO:12. The ACIIPVPAL2 motif can be the motif at nucleotides 765 to 776 of SEQ ID NO:12 or an ACIIPVPAL2 motif heterologous to that in SEQ ID NO:12. The TATABOX4 motif can be the motif at nucleotides 954 to 960 of SEQ ID NO:12 or a TATABOX4 motif heterologous to that in SEQ ID NO:12. The CAAT-box motif can be the motif at nucleotides 986 to 990 of SEQ ID NO:12 or a CAAT-box motif heterologous to that in SEQ ID NO:12. In some embodiments, such regulatory region also contains a CAATBOX1 and UPRMOTIFIIAT motif. The CAATBOX1 motif can be the motif at nucleotides 11 to 15 of SEQ ID NO:12 or a CAATBOX1 motif heterologous to that in SEQ ID NO:12. The UPRMOTIFIIAT motif can be the motif at nucleotides 326 to 344 of SEQ ID NO:12 or an UPRMOTIFIIAT motif heterologous to that in SEQ ID NO:12. In some cases, such regulatory regions can also include a 5' UTR. The 5' UTR can be the 5' UTR at nucleotides 984 to 1043 of SEQ ID NO:12 or can be a heterologous UTR.

In some embodiments, a regulatory region has a nucleotide sequence with 90% or greater sequence identity to the polynucleotide sequence set forth in SEQ ID NO:13 or a fragment thereof, wherein the nucleic acid contains a RYREPEATVFLEB4, SPHCOREZMC1, and AGCBOXNPGLB motif. The RYREPEATVFLEB4 motif can be the motif at nucleotides 786 to 793 of SEQ ID NO:13 or a RYREPEATVFLEB4 motif heterologous to that in SEQ ID NO:13. The SPHCOREZMC1 motif can be the motif at nucleotides 787 to 795 of SEQ ID NO:13 or a SPHCOREZMC1 motif heterologous to that in SEQ ID NO:13. The AGCBOXNPGLB motif can be the motif at nucleotides 1082 to 1088 of SEQ ID NO:13 or an AGCBOXNPGLB motif heterologous to that in SEQ ID NO:13. In some cases, such a regulatory region can also include a 5' UTR.

In some embodiments, a regulatory region has a nucleotide sequence with 90% or greater sequence identity to the polynucleotide sequence set forth in SEQ ID NO:14 or a fragment thereof (e.g., nucleotides 501 to 990 of SEQ ID NO:14), wherein the nucleic acid contains a RYREPEATVFLEB4, P1BS, and TATABOX1 motif. The RYREPEATVFLEB4 motif can be the motif at nucleotides 707 to 713 or 795 to 801 of SEQ ID NO:14 or a RYREPEATVFLEB4 motif heterologous to those in SEQ ID NO:14. The P1BS motif can be the motif at nucleotides 798 to 805 of SEQ ID NO:14 or a P1BS motif heterologous to that in SEQ ID NO:14. The TATABOX1 motif can be the motif at nucleotides 855 to 864 of SEQ ID NO:14 or a TATABOX1 motif heterologous to that in SEQ ID NO:14. In some embodiments, such a regulatory region also includes a ROOTMOTIFTAPDX1 motif. For example, the ROOTMOTIFTAPDX1 motif can be the motif at nucleotides 27 to 31, 77 to 81, or 145 to 149 of SEQ ID NO:14 or a ROOTMOTIFTAPDX1 motif heterologous to those in SEQ ID NO:14. In some cases, such regulatory regions can also include a 5' UTR.

In some embodiments, a regulatory region has a nucleotide sequence with 90% or greater sequence identity to the polynucleotide sequence set forth in SEQ ID NO:15 or a fragment thereof (e.g., nucleotides 702 to 1500 of SEQ ID NO:15), wherein the nucleic acid contains a SBOXATRBCS, MYBbindingsite, and ATHB1ATCONSENSUS motif. The SBOXATRBCS motif can be the motif at nucleotides 846 to 853 of SEQ ID NO:15 or a SBOXATRBCS motif heterologous to those in SEQ ID NO:15. The MYBbindingsite motif can be the motif at nucleotides 994 to 999 of SEQ ID NO:15 or a MYBbindingsite motif heterologous to that in SEQ ID NO:15. The ATHB1ATCONSENSUS motif can be the motif at nucleotides 1315 to 1323 of SEQ ID NO:15 or a ATHB1ATCONSENSUS motif heterologous to that in SEQ ID NO:15. In some embodiments, such a regulatory region also includes an ABRE, E2FAT, PRECONSCRHSP70A, MYBPLANT, and E2FCONSENSUS motif. For example, the ABRE motif can be the motif at nucleotides 80 to 85 of SEQ ID NO:15 or an ABRE motif heterologous to those in SEQ ID NO:15. The E2FAT motif can be the motif at nucleotides 139 to 147 of SEQ ID NO:15 or an E2FAT motif heterologous to that in SEQ ID NO:15. The PRECONSCRHSP70A motif can be the motif at nucleotides 167 to 190 or 297 to 320 of SEQ ID NO:15 or a PRECONSCRHSP70A motif heterologous to those in SEQ ID NO:15. The MYBPLANT motif can be the motif at nucleotides 269 to 276 of SEQ ID NO:15 or a MYBPLANT motif heterologous to that in SEQ ID NO:15. The E2FCONSENSUS motif can be the motif at nucleotides 526 to 533 of SEQ ID NO:15 or a E2FCONSENSUS motif heterologous to that in SEQ ID NO:15. In some cases, such regulatory regions can also include a 5' UTR.

In some embodiments, a regulatory region has a nucleotide sequence with 90% or greater sequence identity to the polynucleotide sequence set forth in SEQ ID NO:16 or a fragment thereof, wherein the nucleic acid contains a P1BS, ABREZMRAB28, SP8BFIBSP8BIB, CCA1ATLHCB1, BOXIIPCCHS, and LRENPCABE motif. The P1BS motif can be the motif at nucleotides 739 to 746 of SEQ ID NO:16 or a P1BS motif heterologous to that in SEQ ID NO:16. The ABREZMRAB2 motif can be the motif at nucleotides 349 to 356 of SEQ ID NO:16 or an ABREZMRAB2 motif heterologous to that in SEQ ID NO:16. The SP8BFIBSP8BIB motif can be the motif at nucleotides 1168 to 1174, 1347 to 1353, or 1377 to 1383 of SEQ ID NO:16 or an SP8BFIBSP8BIB motif heterologous to those in SEQ ID NO:16. The CCA1ATLHCB1 motif can be the motif at nucleotides 1509 to 1516 of SEQ ID NO:16 or a CCA1ATLHCB1 motif heterologous to that in SEQ ID NO:16. The BOXIIPCCHS motif can be the motif at nucleotides 1624 to 1630 of SEQ ID NO:16 or a BOXIIPCCHS motif heterologous to that in SEQ ID NO:16. The LRENPCABE motif can be the motif at nucleotides 1624 to 1631 of SEQ ID NO:16 or a LRENPCABE motif heterologous to that in SEQ ID NO:16. In some cases, such a regulatory region can also include a 5' UTR. The 5' UTR can be the 5' UTR at nucleotides 1857 to 1989 of SEQ ID NO:16 or can be a heterologous UTR.

In some embodiments, a regulatory region has a nucleotide sequence with 90% or greater sequence identity to the polynucleotide sequence set forth in SEQ ID NO:17 or a fragment thereof, wherein the nucleic acid contains a P1BS, MYBGAHV, and CEREGLUBOX2PSLEGA motif. The P1BS motif can be the motif at nucleotides 261 to 268 or 716 to 723 of SEQ ID NO:17 or a P1BS motif heterologous to that in SEQ ID NO:17. The MYBGAHV motif can be the motif at nucleotides 430 to 436 of SEQ ID NO:17 or a MYBGAHV motif heterologous to that in SEQ ID NO:17. The CEREGLUBOX2PSLEGA motif can be the motif at nucleotides 484 to 491 of SEQ ID NO:17 or a CEREGLUBOX2PSLEGA motif heterologous to that in SEQ ID NO:17. In some cases, such a regulatory region can also include a 5' UTR. The 5' UTR can be the 5' UTR at nucleotides 930 to 1000 of SEQ ID NO:17 or can be a heterologous UTR.

In some embodiments, a regulatory region has a nucleotide sequence with 90% or greater sequence identity to the polynucleotide sequence set forth in SEQ ID NO:18 or a fragment thereof (nucleotides 353 to 1248 of SEQ ID NO:18), wherein the nucleic acid contains a CACGCAATGMGH3 or UPRMOTIFIIAT motif. It is noted that nucleotides 353 to 1500 of SEQ ID NO:18 are identical to nucleotides 1 to 1148 of SEQ ID NO:11. The CACGCAATGMGH3 motif can be the motif at nucleotides 1068 to 1075 of SEQ ID NO:18 or a CACGCAATGMGH3 motif heterologous to that in SEQ ID NO:18. The UPRMOTIFIIA motif can be the motif at nucleotides 1122 to 1140 of SEQ ID NO:18 or an UPRMOTIFIIA motif heterologous to that in SEQ ID NO:18. In some cases, such a regulatory region can also include a 5' UTR. The 5' UTR can be the 5' UTR at nucleotides 1189 to 1248 of SEQ ID NO:18 or can be a heterologous UTR.

4. Testing of Promoters

Promoters of the document were tested for activity by cloning the sequence into an appropriate vector, transforming plants with the construct and assaying for marker gene expression. Recombinant DNA constructs were prepared which comprise the promoter sequences of the document inserted into a vector suitable for transformation of plant cells. The construct can be made using standard recombinant DNA techniques (Sambrook et al. 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al. (1992) *Proc. Natl. Acad. Sci. USA* 89: 8794-8797; Hamilton et al. (1996) *Proc. Natl. Acad. Sci. USA* 93: 9975-9979;
(b) YAC: Burke et al. (1987) *Science* 236:806-812;
(c) PAC: Sternberg N. et al. (1990) Proc Natl Acad Sci USA. 87(1):103-7;
(d) Bacteria-Yeast Shuttle Vectors: Bradshaw et al. (1995) *Nucl Acids Res* 23: 4850-4856;
(e) Lambda Phage Vectors: Replacement Vector, e.g., Frischauf et al. (1983) *J. Mol Biol* 170: 827-842; or Insertion vector, e.g., Huynh et al. (1985) In: Glover N M (ed) *DNA Cloning: A practical Approach*, Vol. 1 Oxford: IRL Press; T-DNA gene fusion vectors: Walden et al. (1990) *Mol Cell Biol* 1: 175-194; and
(g) Plasmid vectors: Sambrook et al., infra.

Typically, the construct comprises a vector containing a promoter sequence of the present document operationally linked to any marker gene. The promoter was identified as a promoter by the expression of the marker gene. Although many marker genes can be used, Green Fluorescent Protein (GFP) is preferred. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron or phosphinotricin. Vectors can also include origins of replication, scaffold attachment regions (SARs), markers, homologous sequences, introns, etc.

5. Constructing Promoters with Control Elements 5.1 Combining Promoters and Promoter Control Elements The promoter and promoter control elements of the present document, both naturally occurring and synthetic, can be used alone or combined with each other to produce the desired preferential transcription. Also, the promoters of the document can be combined with other known sequences to obtain other useful promoters to modulate, for example, tissue transcription specific or transcription specific to certain conditions. Such preferential transcription can be determined using the techniques or assays described above.

Promoters can contain any number of control elements. For example, a promoter can contain multiple transcription binding sites or other control elements. One element may confer tissue or organ specificity; another element may limit transcription to specific time periods, etc. Typically, promoters will contain at least a basal or core promoter as described above. Any additional element can be included as desired. For example, a fragment comprising a basal or "core" promoter can be fused with another fragment with any number of additional control elements.

The following are promoters that are induced under stress conditions and can be combined with those of the present document: ldhl (oxygen stress; tomato; see Germain and Ricard (1997) *Plant Mol Biol* 35:949-54), GPx and CAT (oxygen stress; mouse; see Franco et al. (1999) *Free Radic Biol Med* 27:1122-32), ci7 (cold stress; potato; see Kirch et al. (1997) *Plant Mol. Biol.* 33:897-909), Bz2 (heavy metals; maize; see Marrs and Walbot (1997) *Plant Physiol* 113:93-102), HSP32 (hyperthermia; rat; see Raju and Maines (1994) *Biochim Biophys Acta* 1217:273-80), and MAP-KAPK-2 (heat shock; *Drosophila*; see Larochelle and Suter (1995) Gene 163:209-14).

In addition, the following examples of promoters are induced by the presence or absence of light can be used in combination with those of the present document: Topoisomerase II (pea; see Reddy et al. (1999) *Plant Mol Biol* 41:125-37), chalcone synthase (soybean; see Wingender et al. (1989) *Mol Gen Genet.* 218:315-22) mdm2 gene (human tumor; see Saucedo et al. (1998) *Cell Growth Differ* 9:119-30), Clock and BMAL1 (rat; see Namihira et al. (1999) *Neurosci Lett* 271:1-4, PHYA (Arabidopsis; see Canton and Quail (1999) *Plant Physiol* 121:1207-16), PRB-1b (tobacco; see Sessa et al. (1995) *Plant Mol Biol* 28:537-47) and Ypr10 (common bean; see Walter et al. (1996) *Eur J Biochem* 239:281-93).

The promoters and control elements of the following genes can be used in combination with the present document to confer tissue specificity: MipB (iceplant; Yamada et al. (1995) *Plant Cell* 7:1129-42) and SUCS (root nodules; broadbean; Kuster et al. (1993) *Mol Plant Microbe Interact* 6:507-14) for roots, OsSUT1 (rice; Hirose et al. (1997) *Plant Cell Physiol* 38:1389-96) for leaves, Msg (soybean; Stomvik et al. (1999) *Plant Mol Biol* 41:217-31) for siliques, cell (Arabidopsis; Shani et al. (1997) *Plant Mol Biol* 34(6):837-42) and ACT11 (Arabidopsis; Huang et al. (1997) *Plant Mol Biol* 33:125-39) for inflorescence.

Still other promoters are affected by hormones or participate in specific physiological processes, which can be used in combination with those of present document. Some examples are the ACC synthase gene that is induced differently by ethylene and brassinosteroids (mung bean; Yi et al. (1999) *Plant Mol Biol* 41:443-54), the TAPG1 gene that is active during abscission (tomato; Kalaitzis et al. (1995) *Plant Mol Biol* 28:647-56), and the 1-aminocyclopropane-1-carboxylate synthase gene (carnation; Jones et al. (1995) *Plant Mol Biol* 28:505-12) and the CP-2/cathepsin L gene (rat; Kim and Wright (1997) *Biol Reprod* 57:1467-77), both active during senescence.

Spacing between control elements or the configuration or control elements can be determined or optimized to permit the desired protein-polynucleotide or polynucleotide interactions to occur.

For example, if two transcription factors bind to a promoter simultaneously or relatively close in time, the binding sites are spaced to allow each factor to bind without steric hindrance. The spacing between two such hybridizing control elements can be as small as a profile of a protein bound to a control element. In some cases, two protein binding sites can be adjacent to each other when the proteins bind at different times during the transcription process.

Further, when two control elements hybridize the spacing between such elements will be sufficient to allow the promoter polynucleotide to hairpin or loop to permit the two elements to bind. The spacing between two such hybridizing control elements can be as small as a t-RNA loop, to as large as 10 kb.

Typically, the spacing is no smaller than 5 bases; more typically, no smaller than 8; more typically, no smaller than 15 bases; more typically, no smaller than 20 bases; more typically, no smaller than 25 bases; even more typically, no smaller than 30, 35, 40 or 50 bases.

Usually, the fragment size in no larger than 5 kb bases; more usually, no larger than 2 kb; more usually, no larger than 1 kb; more usually, no larger than 800 bases; more usually, no larger than 500 bases; even more usually, no more than 250, 200, 150 or 100 bases.

Such spacing between promoter control elements can be determined using the techniques and assays described above.

5.2 Vectors Used to Transform Cells/Hosts

A plant transformation construct containing a promoter of the present document may be introduced into plants by any plant transformation method. Methods and materials for transforming plants by introducing a plant expression construct into a plant genome in the practice of this document can include any of the well-known and demonstrated methods including electroporation (U.S. Pat. No. 5,384,253); microprojectile bombardment (U.S. Pat. No. 5,015,580; U.S. Pat. No. 5,550,318; U.S. Pat. No. 5,538,880; U.S. Pat. No. 6,160,208; U.S. Pat. No. 6,399,861; and U.S. Pat. No. 6,403,865); *Agrobacterium*-mediated transformation (U.S. Pat. No. 5,824,877; U.S. Pat. No. 5,591,616; U.S. Pat. No. 5,981,840; and U.S. Pat. No. 6,384,301); and protoplast transformation (U.S. Pat. No. 5,508,184).

The present promoters and/or promoter control elements may be delivered to a system such as a cell by way of a vector. For the purposes of this document, such delivery may range from simply introducing the promoter or promoter control element by itself randomly into a cell to integration of a cloning vector containing the present promoter or promoter control element. Thus, a vector need not be limited to a DNA molecule such as a plasmid, cosmid or bacterial phage that has the capability of replicating autonomously in a host cell. All other manner of delivery of the promoters and promoter control elements of the document are envisioned. The various T-DNA vector types are a preferred vector for use with the present document. Many useful vectors are commercially available.

It may also be useful to attach a marker sequence to the present promoter and promoter control element in order to determine activity of such sequences. Marker sequences typically include genes that provide antibiotic resistance, such as tetracycline resistance, hygromycin resistance or ampicillin resistance, or provide herbicide resistance. Specific selectable marker genes may be used to confer resistance to herbicides such as glyphosate, glufosinate or bromoxynil (Comai et al. (1985) *Nature* 317: 741-744; Gordon-Kamm et al. (1990) *Plant Cell* 2: 603-618; and Stalker et al. (1988) *Science* 242: 419-423). Other marker genes exist which provide hormone responsiveness.

The promoter or promoter control element of the present document may be operably linked to a polynucleotide to be transcribed. In this manner, the promoter or promoter control element may modify transcription by modulating transcript levels of that polynucleotide when inserted into a genome.

However, prior to insertion into a genome, the promoter or promoter control element need not be linked, operably or otherwise, to a polynucleotide to be transcribed. For example, the promoter or promoter control element may be inserted alone into the genome in front of a polynucleotide already present in the genome. In this manner, the promoter or promoter control element may modulate the transcription of a polynucleotide that was already present in the genome. This polynucleotide may be native to the genome or inserted at an earlier time.

Alternatively, the promoter or promoter control element may be inserted into a genome alone to modulate transcription. See, for example, Vaucheret, H et al. (1998) *Plant J* 16: 651-659. Rather, the promoter or promoter control element may be simply inserted into a genome or maintained extrachromosomally as a way to divert transcription resources of the system to itself. This approach may be used to downregulate the transcript levels of a group of polynucleotide(s).

The nature of the polynucleotide to be transcribed is not limited. Specifically, the polynucleotide may include sequences that will have activity as RNA as well as sequences that result in a polypeptide product. These sequences may include, but are not limited to antisense sequences, RNAi sequences, ribozyme sequences, spliceosomes, amino acid coding sequences, and fragments thereof. Specific coding sequences may include, but are not limited to endogenous proteins or fragments thereof, or heterologous proteins including marker genes or fragments thereof.

Constructs of the present document would typically contain a promoter operably linked to a transcribable nucleic acid molecule operably linked to a 3' transcription termination nucleic acid molecule. In addition, constructs may include but are not limited to additional regulatory nucleic acid molecules from the 3'-untranslated region (3' UTR) of plant genes (e.g., a 3' UTR to increase mRNA stability of the mRNA, such as the PI-II termination region of potato or the octopine or nopaline synthase 3' termination regions). Constructs may include but are not limited to the 5' untranslated regions (5' UTR) of an mRNA nucleic acid molecule which can play an important role in translation initiation and can also be a genetic component in a plant expression construct. For example, non-translated 5' leader nucleic acid molecules derived from heat shock protein genes have been demonstrated to enhance gene expression in plants (see for example, U.S. Pat. No. 5,659,122 and U.S. Pat. No. 5,362,865, all of which are hereby incorporated by reference). These additional upstream and downstream regulatory nucleic acid molecules may be derived from a source that is native or heterologous with respect to the other elements present on the promoter construct.

Thus, one embodiment of the document is a promoter such as provided in SEQ ID NOs: 1-18 or a fragment thereof, operably linked to a transcribable nucleic acid molecule so as to direct transcription of said transcribable nucleic acid molecule at a desired level or in a desired tissue or developmental pattern upon introduction of said construct into a plant cell. In some cases, the transcribable nucleic acid molecule comprises a protein-coding region of a gene, and the promoter provides for transcription of a functional mRNA molecule that is translated and expressed as a protein product. Constructs may also be constructed for transcription of antisense RNA molecules or other similar inhibitory RNA in order to inhibit expression of a specific RNA molecule of interest in a target host cell.

Exemplary transcribable nucleic acid molecules for incorporation into constructs of the present document include, for example, nucleic acid molecules or genes from a species other than the target gene species, or even genes that originate with or are present in the same species, but are incorporated into recipient cells by genetic engineering methods rather than classical reproduction or breeding techniques. Exogenous gene or genetic element is intended to refer to any gene or nucleic acid molecule that is introduced into a recipient cell. The type of nucleic acid molecule included in the exogenous nucleic acid molecule can include a nucleic acid molecule that is already present in the plant cell, a nucleic acid molecule from another plant, a nucleic acid molecule from a different organism, or a nucleic acid molecule generated externally, such as a nucleic acid molecule containing an antisense message of a gene, or a nucleic acid molecule encoding an artificial or modified version of a gene.

The promoters of the present document can be incorporated into a construct using marker genes as described, and tested in transient analyses that provide an indication of gene expression in stable plant systems. As used herein the term "marker gene" refers to any transcribable nucleic acid molecule whose expression can be screened for or scored in some way. Methods of testing for marker gene expression in transient assays are known to those of skill in the art.

Transient expression of marker genes has been reported using a variety of plants, tissues, plant cell(s), and DNA delivery systems. For example, types of transient analyses can include but are not limited to direct gene delivery via electroporation or particle bombardment of tissues in any transient plant assay using any plant species of interest. Such transient systems would include, but are not limited to, electroporation of protoplasts from a variety of tissue sources or particle bombardment of specific tissues of interest. The present document encompasses the use of any transient expression system to evaluate promoters or promoter fragments operably linked to any transcribable nucleic acid molecules, including but not limited to selected reporter genes, marker genes, or genes of agronomic interest. Examples of plant tissues envisioned to test in transients via an appropriate delivery system would include, but are not limited to, leaf base tissues, callus, cotyledons, roots, endosperm, embryos, floral tissue, pollen, and epidermal tissue.

Promoters and control elements of the present document are useful for modulating metabolic or catabolic processes. Such processes include, but are not limited to, secondary product metabolism, amino acid synthesis, seed protein storage, increased biomass, oil development, pest defense and nitrogen usage. Some examples of genes, transcripts and peptides or polypeptides participating in these processes, which can be modulated by the present document: are tryptophan decarboxylase (tdc) and strictosidine synthase (str1), dihydrodipicolinate synthase (DHDPS) and aspartate kinase (AK), 2S albumin and alpha-, beta-, and gamma-zeins, ricinoleate and 3-ketoacyl-ACP synthase (KAS), *Bacillus thuringiensis* (Bt) insecticidal protein, cowpea trypsin inhibitor (CpTI), asparagine synthetase and nitrite reductase. Alternatively, expression constructs can be used to inhibit expression of these peptides and polypeptides by incorporating the promoters in constructs for antisense use, co-suppression use or for the production of dominant negative mutations.

As explained above, several types of regulatory elements exist concerning transcription regulation. Each of these regulatory elements may be combined with the present vector if desired. Translation of eukaryotic mRNA is often initiated at the codon that encodes the first methionine. Thus, when constructing a recombinant polynucleotide according to the present document for expressing a protein product, it is preferable to ensure that the linkage between the 3' portion, preferably including the TATA box, of the promoter and the polynucleotide to be transcribed, or a functional derivative thereof, does not contain any intervening codons which are capable of encoding a methionine.

The vector of the present document may contain additional components. For example, an origin of replication allows for replication of the vector in a host cell. Additionally, homologous sequences flanking a specific sequence allow for specific recombination of the specific sequence at a desired location in the target genome. T-DNA sequences also allow for insertion of a specific sequence randomly into a target genome.

The vector may also be provided with a plurality of restriction sites for insertion of a polynucleotide to be transcribed as well as the promoter and/or promoter control elements of the present document. The vector may additionally contain selectable marker genes. The vector may also contain a transcriptional and translational initiation region, and a transcriptional and translational termination region functional in the host cell. The termination region may be native with the transcriptional initiation region, may be native with the polynucleotide to be transcribed, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; Joshi et al. (1987) *Nucleic Acid Res.* 15:9627-9639.

Where appropriate, the polynucleotide to be transcribed may be optimized for increased expression in a certain host cell. For example, the polynucleotide can be synthesized using preferred codons for improved transcription and translation. See U.S. Pat. Nos. 5,380,831, 5,436,391; see also and Murray et al. (1989) *Nucleic Acids Res.* 17:477-498.

Additional sequence modifications include elimination of sequences encoding spurious polyadenylation signals, exon intron splice site signals, transposon-like repeats, and other such sequences well characterized as deleterious to expression. The G-C content of the polynucleotide may be adjusted to levels average for a given cellular host, as calculated by reference to known genes expressed in the host cell. The polynucleotide sequence may be modified to avoid hairpin secondary mRNA structures.

A general description of expression vectors and reporter genes can be found in Gruber, et al. (1993) "Vectors for Plant Transformation" In *Methods in Plant Molecular Biology & Biotechnology*, Glich et al. Eds. pp. 89-119, CRC Press. Moreover GUS expression vectors and GUS gene cassettes are available from Clonetech Laboratories, Inc., Palo Alto, Calif. while luciferase expression vectors and luciferase gene cassettes are available from Promega Corp. (Madison, Wis.). GFP vectors are available from Aurora Biosciences.

5.3 Polynucleotide Insertion into a Host Cell

The promoters according to the present document can be inserted into a host cell. A host cell includes but is not limited to a plant, mammalian, insect, yeast, and prokaryotic cell, preferably a plant cell.

The method of insertion into the host cell genome is chosen based on convenience. For example, the insertion into the host cell genome may either be accomplished by vectors that integrate into the host cell genome or by vectors which exist independent of the host cell genome.

The promoters of the present document can exist autonomously or independent of the host cell genome. Vectors of these types are known in the art and include, for example, certain type of non-integrating viral vectors, autonomously replicating plasmids, artificial chromosomes, and the like.

Additionally, in some cases transient expression of a promoter may be desired.

The promoter sequences, promoter control elements or vectors of the present document may be transformed into host cells. These transformations may be into protoplasts or intact tissues or isolated cells. Preferably expression vectors are introduced into intact tissue. General methods of culturing plant tissues are provided for example by Maki et al. (1993) "Procedures for Introducing Foreign DNA into Plants" In *Methods in Plant Molecular Biology & Biotechnology*, Glich et al. Eds. pp. 67-88 CRC Press; and by Phillips et al. (1988) "Cell-Tissue Culture and In-Vitro Manipulation" In *Corn & Corn Improvement*, 3rd Edition Sprague et al. eds., pp. 345-387, American Society of Agronomy Inc. et al.

Methods of introducing polynucleotides into plant tissue include the direct infection or co-cultivation of plant cell with *Agrobacterium tumefaciens*, Horsch et al. (1985) *Science*, 227:1229. Descriptions of *Agrobacterium* vector systems and methods for *Agrobacterium*-mediated gene transfer provided by Gruber et al. supra.

Alternatively, polynucleotides are introduced into plant cells or other plant tissues using a direct gene transfer method such as microprojectile-mediated delivery, DNA injection, electroporation and the like. More preferably polynucleotides are introduced into plant tissues using the microprojectile media delivery with the biolistic device. See, for example, Tomes et al., "Direct DNA transfer into intact plant cells via microprojectile bombardment" In: Gamborg and Phillips (Eds.) Plant Cell, Tissue and Organ Culture: Fundamental Methods, Springer Verlag, Berlin (1995).

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), and members of the genus *Brassica*.

Methods for transforming monocots are well known to those skilled in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including indica and japonica varieties); sorghum (*Sorghum bicolor*); sugar cane (*Saccharum* sp); tall fescue (*Festuca arundinacea*); turfgrass species (e.g. species: *Agrostis stolonifera, Poa pratensis, Stenotaphrum secundatum*); wheat (*Triticum aestivum*), switchgrass (*Panicum vigatum*) and alfalfa (*Medicago sativa*). It is apparent to those of skill in the art that a number of transformation methodologies can be used and modified for production of stable transgenic plants from any number of target plants of interest.

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea*.

Suitable species include *Panicum* spp. or hybrids thereof, *Sorghum* spp. or hybrids thereof, sudangrass, *Miscanthus* spp. or hybrids thereof, *Saccharum* spp. or hybrids thereof, *Erianthus* spp., *Populus* spp., *Andropogon gerardii* (big bluestem), *Pennisetum purpureum* (elephant grass) or hybrids thereof (e.g., *Pennisetum purpureum*×*Pennisetum typhoidum*), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed) or hybrids thereof, *Secale cereale* (rye), *Salix* spp. (willow), *Eucalyptus* spp. (eucalyptus), *Triticosecale* (*Triticum*—wheat X rye), *Tripsicum dactyloides* (Eastern gammagrass), *Leymus cinereus* (basin wildrye), *Leymus condensatus* (giant wildrye), and bamboo.

In some embodiments, a suitable species can be a wild, weedy, or cultivated sorghum species such as, but not limited to, *Sorghum almum, Sorghum amplum, Sorghum angustum, Sorghum arundinaceum, Sorghum bicolor* (such as bicolor, guinea, caudatum, kafir, and durra), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare*, or hybrids such as *Sorghum*×*almum, Sorghum*×*sudangrass* or *Sorghum*×*rummondii*.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea*.

Suitable species also include *Beta vulgaris* (sugarbeet), and *Manihot esculenta* (cassava).

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, brusselsprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (=*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii*, and *Tanacetum parthenium*.

Suitable species also include *Parthenium argentatum* (guayule), *Hevea* spp. (rubber), *Mentha spicata* (mint), *Mentha piperita* (mint), *Bixa orellana*, and *Alstroemeria* spp.

Suitable species also include *Rosa* spp. (rose), *Dianthus caryophyllus* (carnation), *Petunia* spp. (petunia) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple, *Hordeum vulgare* (barley), *Poa pratensis* (bluegrass), *Lolium* spp. (ryegrass) and *Phleum pratense* (timothy).

Thus, the methods and compositions can be used over a broad range of plant species, including species from the dicot genera *Brassica, Carthamus, Glycine, Gossypium, Helianthus, Jatropha, Parthenium, Populus*, and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum*, and *Zea*. In some embodiments, a plant is a member of the species *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledonous plants and plant cell systems, wherein such plants are hybrids of different species or varieties of a specific species (e.g., *Saccharum* sp.×*Miscanthus* sp., *Panicum virgatum*×*Panicum amarum, Panicum virgatum*×*Panicum amarulum*, and *Pennisetum purpureum*×*Pennisetum typhoidum*).

In another embodiment of the current document, expression constructs can be used for gene expression in callus culture for the purpose of expressing marker genes encoding peptides or polypeptides that allow identification of transformed plants. Here, a promoter that is operatively linked to a polynucleotide to be transcribed is transformed into plant cells and the transformed tissue is then placed on callus-inducing media. If the transformation is conducted with leaf discs, for example, callus will initiate along the cut edges. Once callus growth has initiated, callus cells can be transferred to callus shoot-inducing or callus root-inducing media. Gene expression will occur in the callus cells developing on the appropriate media: callus root-inducing promoters will be activated on callus root-inducing media, etc. Examples of such peptides or polypeptides useful as transformation markers include, but are not limited to barstar, glyphosate, chloramphenicol acetyltransferase (CAT), kanamycin, spectinomycin, streptomycin or other antibiotic resistance enzymes, green fluorescent protein (GFP), and β-glucuronidase (GUS), etc. Some of the promoters provided in SEQ ID NOs: 1-18 will also be capable of sustaining expression in some tissues or organs after the initiation or completion of regeneration. Examples of these tissues or organs are somatic embryos, cotyledon, hypocotyl, epicotyl, leaf, stems, roots, flowers and seed.

Integration into the host cell genome also can be accomplished by methods known in the art, for example, by the homologous sequences or T-DNA discussed above or using the Cre-lox system (A. C. Vergunst et al. (1998) *Plant Mol. Biol.* 38:393).

6. Uses of the Promoters

6.1 Use of the Promoters to Study and Screen for Expression

The promoters of the present application can be used to further understand developmental mechanisms. For example, promoters that are specifically induced during callus formation, somatic embryo formation, shoot formation or root formation can be used to explore the effects of overexpression, repression or ectopic expression of target genes, or for isolation of trans-acting factors.

The vectors of the present application can be used not only for expression of coding regions but may also be used in exon-trap cloning, or promoter trap procedures to detect differential gene expression in various tissues (see Lindsey et al. (1993) *Transgenic Research* 2:3347. Auch and Reth (1990) *Nucleic Acids Research* 18: 6743).

Entrapment vectors, first described for use in bacteria (Casadaban and Cohen (1979) *Proc. Nat. Aca. Sci. U.S.A.* 76: 4530; Casadaban et al. (1980) *J. Bacteriol.* 143: 971) permit selection of insertional events that lie within coding sequences. Entrapment vectors can be introduced into pluripotent ES cells in culture and then passed into the germline via chimeras (Gossler et al. 1989) *Science* 244: 463; Skarnes (1990) *Biotechnology* 8: 827). Promoter or gene trap vectors often contain a reporter gene, e.g., lacZ, lacking its own promoter and/or splice acceptor sequence upstream. That is, promoter gene traps contain a reporter gene with a splice site but no promoter. If the vector lands in a gene and is spliced into the gene product, then the reporter gene is expressed.

Recently, the isolation of preferentially-induced genes has been made possible with the use of sophisticated promoter traps (e.g. IVET) that are based on conditional auxotrophy complementation or drug resistance. In one WET approach, various bacterial genome fragments are placed in front of a necessary metabolic gene coupled to a reporter gene. The DNA constructs are inserted into a bacterial strain otherwise lacking the metabolic gene, and the resulting bacteria are used to infect the host organism. Only bacteria expressing the metabolic gene survive in the host organism; consequently, inactive constructs can be eliminated by harvesting only bacteria that survive for some minimum period in the host. At the same time, broadly active constructs can be eliminated by screening only bacteria that do not express the reporter gene under laboratory conditions. The bacteria selected by such a method contain constructs that are selectively induced only during infection of the host. The IVET approach can be modified for use in plants to identify genes induced in either the bacteria or the plant cells upon pathogen infection or root colonization. For information on IVET see the articles by Mahan et al. (1993) *Science* 259:686-688, Mahan et al. (1995) *Proc. Natl. Acad. Sci. USA* 92:669-673, Heithoff et al. (1997) *Proc. Natl. Acad. Sci. USA* 94:934-939, and Wang et al. (1996) *Proc. Natl. Acad. Sci. USA* 93:10434.

6.2 Use of the Promoters to Transcribe Genes of Interest

In one embodiment of the document, a nucleic acid molecule as shown in SEQ ID NOs: 1-12 is incorporated into a construct such that a promoter of the present document is operably linked to a transcribable nucleic acid molecule that is a gene of agronomic interest. As used herein, the term "gene of agronomic interest" refers to a transcribable nucleic acid molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait. A gene of agronomic interest that provides a beneficial agronomic trait to crop plants may be, for example, including, but not limited to genetic elements comprising herbicide resistance, increased yield, increased biomass, insect control, fungal disease resistance, virus resistance, nematode resistance, bacterial disease resistance, starch production, modified oils production, high oil production, modified fatty acid content, high protein production, fruit ripening, enhanced animal and human nutrition, biopolymers, environmental stress resistance, pharmaceutical peptides, improved processing traits, improved digestibility, industrial enzyme production, improved flavor, nitrogen fixation, hybrid seed production, and biofuel production. The genetic elements, methods, and transgenes described in the patents listed above are hereby incorporated by reference.

Alternatively, a transcribable nucleic acid molecule can effect the above mentioned phenotypes by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any nucleic acid molecule that encodes a protein or mRNA that expresses a phenotype or morphology change of interest may be useful for the practice of the present document.

6.3. Stress Induced Preferential Transcription

Promoters and control elements providing modulation of transcription under oxidative, drought, oxygen, wound, and methyl jasmonate stress are particularly useful for producing host cells or organisms that are more resistant to biotic and abiotic stresses. In a plant, for example, modulation of genes, transcripts, and/or polypeptides in response to oxidative stress can protect cells against damage caused by oxidative agents, such as hydrogen peroxide and other free radicals.

Drought induction of genes, transcripts, and/or polypeptides are useful to increase the viability of a plant, for example, when water is a limiting factor. In contrast, genes, transcripts, and/or polypeptides induced during oxygen stress can help the flood tolerance of a plant.

The promoters and control elements of the present document can modulate stresses similar to those described in, for example, stress conditions are VuPLD1 (drought stress; Cowpea; see Pham-Thi et al. (1999) *Plant Mol Biol* 39:1257-65), pyruvate decarboxylase (oxygen stress; rice; see Rivosal et al. (1997) *Plant Physiol* 114(3): 1021-29), chromoplast specific carotenoid gene (oxidative stress; *Capsicum*; see Bouvier et al. (1998) *J Biol Chem* 273: 30651-59).

Promoters and control elements providing preferential transcription during wounding or induced by methyl jasmonate can produce a defense response in host cells or organisms. In a plant, for example, preferential modulation of genes, transcripts, and/or polypeptides under such conditions is useful to induce a defense response to mechanical wounding, pest or pathogen attack or treatment with certain chemicals.

Promoters and control elements of the present document also can trigger a response similar to those described for cf9 (viral pathogen; tomato; see O'Donnell et al. (1998) Plant J 14(1): 137-42), hepatocyte growth factor activator inhibitor type 1 (HAI-1), which enhances tissue regeneration (tissue injury; human; Koono et al. (1999) *J Histochem Cytochem* 47: 673-82), copper amine oxidase (CuAO), induced during ontogenesis and wound healing (wounding; chick-pea; Rea et al. (1998) *FEBS Lett* 437: 177-82), proteinase inhibitor II (wounding; potato; see Pena-Cortes et al. (1988) *Planta* 174: 84-89), protease inhibitor II (methyl jasmonate; tomato; see Farmer and Ryan (1990) *Proc Natl Acad Sci USA* 87: 7713-7716), two vegetative storage protein genes VspA and VspB (wounding, jasmonic acid, and water deficit; soybean; see Mason and Mullet (1990) *Plant Cell* 2: 569-579).

Up-regulation and down-regulation of transcription are useful for these applications. For instance, genes, transcripts, and/or polypeptides that increase oxidative, flood, or drought tolerance may require up-regulation of transcription.

Typically, promoter or control elements, which provide preferential transcription in wounding or under methyl jasmonate induction, produce transcript levels that are statistically significant as compared to cell types, organs or tissues under other conditions.

For preferential up-regulation of transcription, promoter and control elements produce transcript levels that are above background of the assay.

6.4. Light Induced Preferential Transcription

Promoters and control elements providing preferential transcription when induced by light exposure can be utilized to modulate growth, metabolism, and development; to increase drought tolerance; and decrease damage from light stress for host cells or organisms. In a plant, for example, modulation of genes, transcripts, and/or polypeptides in response to light is useful
(1) to increase the photosynthetic rate;
(2) to increase storage of certain molecules in leaves or green parts only, e.g. silage with high protein or starch content;
(3) to modulate production of exogenous compositions in green tissue, e.g. certain feed enzymes;
(4) to induce growth or development, such as fruit development and maturity, during extended exposure to light;
(5) to modulate guard cells to control the size of stomata in leaves to prevent water loss, or
(6) to induce accumulation of beta-carotene to help plants cope with light induced stress.

The promoters and control elements of the present document also can trigger responses similar to those described in: abscisic acid insensitive3 (ABI3) (dark-grown *Arabidopsis* seedlings, see Rohde et al. (2000) *Plant Cell* 12: 35-52), asparagine synthetase (pea root nodules, see Tsai and Coruzzi (1990) *EMBO J* 9: 323-32), mdm2 gene (human tumor, see Saucedo et al. (1998) *Cell Growth Differ* 9: 119-30).

Up-regulation and down-regulation of transcription are useful for these applications. For instance, genes, transcripts, and/or polypeptides that increase drought or light tolerance may require up-regulation of transcription.

Typically, promoter or control elements, which provide preferential transcription in cells, tissues or organs exposed to light, produce transcript levels that are statistically significant as compared to cells, tissues, or organs under decreased light exposure (intensity or length of time).

For preferential up-regulation of transcription, promoter and control elements produce transcript levels that are above background of the assay.

6.5. Dark Induced Preferential Transcription

Promoters and control elements providing preferential transcription when induced by dark or decreased light intensity or decreased light exposure time can be utilized to time growth, metabolism, and development, to modulate photosynthesis capabilities for host cells or organisms. In a plant, for example, modulation of genes, transcripts, and/or polypeptides in response to dark is useful, for example,
(1) to induce growth or development, such as fruit development and maturity, despite lack of light;
(2) to modulate genes, transcripts, and/or polypeptide active at night or on cloudy days; or
(3) to preserve the plastid ultra structure present at the onset of darkness.

The present promoters and control elements can also trigger response similar to those described in the section above.

Up-regulation and down-regulation of transcription are useful for these applications. For instance, genes, transcripts, and/or polypeptides that increase or decrease growth and development may require up-regulation of transcription.

Typically, promoter or control elements, which provide preferential transcription under exposure to dark or decrease light intensity or decrease exposure time, produce transcript levels that are statistically significant.

For preferential up-regulation of transcription, promoter and control elements produce transcript levels that are above background of the assay.

6.6. Leaf Preferential Transcription

Promoters and control elements providing preferential transcription in a leaf can modulate growth, metabolism, and development or modulate energy and nutrient utilization in host cells or organisms. In a plant, for example, preferential modulation of genes, transcripts, and/or polypeptide in a leaf, is useful, for example,
(1) to modulate leaf size, shape, and development;
(2) to modulate the number of leaves; or
(3) to modulate energy or nutrient usage in relation to other organs and tissues Up-regulation and down-regulation of transcription are useful for these applications. For instance, genes, transcripts, and/or polypeptides that increase growth, for example, may require up-regulation of transcription.

Typically, promoter or control elements, which provide preferential transcription in the cells, tissues, or organs of a leaf, produce transcript levels that are statistically significant as compared to other cells, organs or tissues.

For preferential up-regulation of transcription, promoter and control elements produce transcript levels that are above background of the assay.

6.7. Root Preferential Transcription

Promoters and control elements providing preferential transcription in a root can modulate growth, metabolism, development, nutrient uptake, nitrogen fixation, or modulate energy and nutrient utilization in host cells or organisms. In a plant, for example, preferential modulation of genes, transcripts, and/or polypeptide in a root, is useful,
(1) to modulate root size, shape, and development;
(2) to modulate the number of roots, or root hairs;
(3) to modulate mineral, fertilizer, or water uptake;
(4) to modulate transport of nutrients; or
(4) to modulate energy or nutrient usage in relation to other cells, organs and tissues.

Up-regulation and down-regulation of transcription are useful for these applications. For instance, genes, transcripts, and/or polypeptides that increase or decrease growth, for example, may require up-regulation of transcription.

Typically, promoter or control elements, which provide preferential transcription in cells, tissues, or organs of a root, produce transcript levels that are statistically significant as compared to other cells, organs or tissues.

For preferential up-regulation of transcription, promoter and control elements produce transcript levels that are above background of the assay.

6.8. Stem/Shoot Preferential Transcription

Promoters and control elements providing preferential transcription in a stem or shoot can modulate growth, metabolism, and development or modulate energy and nutrient utilization in host cells or organisms. In a plant, for example, preferential modulation of genes, transcripts, and/or polypeptide in a stem or shoot, is useful, for example,
 (1) to modulate stem/shoot size, shape, and development; or
 (2) to modulate energy or nutrient usage in relation to other organs and tissues Up-regulation and down-regulation of transcription are useful for these applications. For instance, genes, transcripts, and/or polypeptides that increase growth, for example, may require up-regulation of transcription.

Typically, promoter or control elements, which provide preferential transcription in the cells, tissues, or organs of a stem or shoot, produce transcript levels that are statistically significant as compared to other cells, organs or tissues.

For preferential up-regulation of transcription, promoter and control elements produce transcript levels that are above background of the assay.

6.9. Fruit and Seed Preferential Transcription

Promoters and control elements providing preferential transcription in a silique or fruit can time growth, development, or maturity; or modulate fertility; or modulate energy and nutrient utilization in host cells or organisms. In a plant, for example, preferential modulation of genes, transcripts, and/or polypeptides in a fruit, is useful
 (1) to modulate fruit size, shape, development, and maturity;
 (2) to modulate the number of fruit or seeds;
 (3) to modulate seed shattering;
 (4) to modulate components of seeds, such as, storage molecules, starch, protein, oil, vitamins, anti-nutritional components, such as phytic acid;
 (5) to modulate seed and/or seedling vigor or viability;
 (6) to incorporate exogenous compositions into a seed, such as lysine rich proteins;
 (7) to permit similar fruit maturity timing for early and late blooming flowers; or
 (8) to modulate energy or nutrient usage in relation to other organs and tissues.

Up-regulation and down-regulation of transcription are useful for these applications. For instance, genes, transcripts, and/or polypeptides that increase or decrease growth, for example, may require up-regulation of transcription.

Typically, promoter or control elements, which provide preferential transcription in the cells, tissues, or organs of siliques or fruits, produce transcript levels that are statistically significant as compared to other cells, organs or tissues.

For preferential up-regulation of transcription, promoter and control elements produce transcript levels that are above background of the assay.

6.10. Callus Preferential Transcription

Promoters and control elements providing preferential transcription in a callus can be useful to modulating transcription in dedifferentiated host cells. In a plant transformation, for example, preferential modulation of genes, transcripts, in callus is useful to modulate transcription of a marker gene, which can facilitate selection of cells that are transformed with exogenous polynucleotides.

Up-regulation and down-regulation of transcription are useful for these applications. For instance, genes, transcripts, and/or polypeptides that increase marker gene detectability, for example, may require up-regulation of transcription.

For preferential up-regulation of transcription, promoter and control elements produce transcript levels that are above background of the assay.

6.11. Flower Specific Transcription

Promoters and control elements providing preferential transcription in flowers can modulate pigmentation; or modulate fertility in host cells or organisms. In a plant, for example, preferential modulation of genes, transcripts, and/or polypeptides in a flower, is useful,
 (1) to modulate petal color; or
 (2) to modulate the fertility of pistil and/or stamen.

Up-regulation and down-regulation of transcription are useful for these applications. For instance, genes, transcripts, and/or polypeptides that increase or decrease pigmentation, for example, may require up-regulation of transcription Typically, promoter or control elements, which provide preferential transcription in flowers, produce transcript levels that are statistically significant as compared to other cells, organs or tissues.

For preferential up-regulation of transcription, promoter and control elements produce transcript levels that are above background of the assay.

6.12. Immature Bud/Floret and Inflorescence Preferential Transcription

Promoters and control elements providing preferential transcription in an immature bud/floret or inflorescence can time growth, development, or maturity; or modulate fertility or viability in host cells or organisms. In a plant, for example, preferential modulation of genes, transcripts, and/or polypeptide in an immature bud and/or inflorescence, is useful,
 (1) to modulate embryo development, size, and maturity;
 (2) to modulate endosperm development, size, and composition;
 (3) to modulate the number of seeds and fruits; or
 (4) to modulate seed development and viability.

Up-regulation and down-regulation of transcription are useful for these applications. For instance, genes, transcripts, and/or polypeptides that increase or decrease growth, for example, may require up-regulation of transcription.

Typically, promoter or control elements, which provide preferential transcription in immature buds/florets and inflorescences, produce transcript levels that are statistically significant as compared to other cell types, organs or tissues.

For preferential up-regulation of transcription, promoter and control elements produce transcript levels that are above background of the assay.

6.13. Senescence Preferential Transcription

Promoters and control elements providing preferential transcription during senescence can be used to modulate cell degeneration, nutrient mobilization, and scavenging of free radicals in host cells or organisms. Other types of responses that can be modulated include, for example, senescence associated genes (SAG) that encode enzymes thought to be involved in cell degeneration and nutrient mobilization (Arabidopsis; see Hensel et al. (1993) *Plant Cell* 5: 553-64), and the CP-2/cathepsin L gene (rat; Kim and Wright (1997) *Biol Reprod* 57: 1467-77), both induced during senescence.

In a plant, for example, preferential modulation of genes, transcripts, and/or polypeptides during senescencing is useful to modulate fruit ripening.

Up-regulation and down-regulation of transcription are useful for these applications. For instance, genes, transcripts, and/or polypeptides that increase or decrease scavenging of free radicals, for example, may require up-regulation of transcription.

Typically, promoter or control elements, which provide preferential transcription in cells, tissues, or organs during senescence, produce transcript levels that are statistically significant as compared to other conditions.

For preferential up-regulation of transcription, promoter and control elements produce transcript levels that are above background of the assay.

6.14. Germination Preferential Transcription

Promoters and control elements providing preferential transcription in a germinating seed can time growth, development, or maturity; or modulate viability in host cells or organisms. In a plant, for example, preferential modulation of genes, transcripts, and/or polypeptide in a germinating seed, is useful, (1) to modulate the emergence of the hypocotyls, cotyledons and radical; or
(2) to modulate shoot and primary root growth and development;

Up-regulation and down-regulation of transcription are useful for these applications. For instance, genes, transcripts, and/or polypeptides that increase or decrease growth, for example, may require up-regulation of transcription.

Typically, promoter or control elements, which provide preferential transcription in a germinating seed, produce transcript levels that are statistically significant as compared to other cell types, organs or tissues.

For preferential up-regulation of transcription, promoter and control elements produce transcript levels that are above background of the assay.

7. Experimental Procedures and Results

*Agrobacterium*-Mediated Transformation of Rice

Induce Calli Formation from Mature Rice Seeds

De-husk mature seeds using de-husker (Kett; Cat #TR120) and discard spotted ones if present. Transfer 100 de-husked seeds to a 50 mL conical tube. Add 24 mL autoclaved distilled water and then 6 ml Clorox™ (Clorox contains 5.25% sodium hypochlorite so final concentration is 1.05%) and 2-3 drops of Liqui-Nox®. Shake the tube occasionally for 30 min. Pour out Clorox™ solution and rinse seeds 5 times with sterile water. Dry the seeds on autoclaved Kimwipes™ for a few minutes. Transfer seeds on the semi-solid N6-P medium (3.98 g/L N6 basal salt mixture, 0.8 mg/L KI, 0.025 mg/L $CoCl_2.6H_2O$, 0.025 mg/L $CuSO_4.5H_2O$, 0.25 mg/L $NaMoO_4.2H_2O$, 2 mg/L Glycine, 100 mg/L Myo-inositol, 5 mg/L Thiamine HCl, 1 mg/L Pyridoxine.HCl, 1 mg/L Nicotinic acid, 2.8 g/L Proline, 300 mg/L Casamino acid, 30 g/L Sucrose, 2 mg/L 2,4-Dichloro-Phenoxyacetic Acid, 4 g/L Gel rite, pH 5.6); 10 seeds each Petri dish. Each Petri dish contains 30 ml N6-P medium. Dishes are sealed with antifungal tape to allow air exchange. Place the plates at 28° C. under cold fluorescent light. Many granular calli should be formed within 4 weeks. Calli of good quality consist of small and spherical cells with dense cytoplasm, which are competent for transformation. The calli can be used directly for *Agrobacterium* infection, or subculture them for later use.

Infection and Co-Cultivation of Calli with *Agrobacterium* Cells

Pick up a single *Agrobacterium* clone from stock and culture it in 2 mL YEB liquid medium by growing it overnight in a shaker. Appropriate antibiotics are included at 50 mg/L or higher. Put on 28° C. shaker overnight. The next day, reinoculate 25 µL of overnight culture into 5 mL of liquid YEB with selection and grow overnight at 28° C. The next day, use this culture for transformation. Transfer the liquid culture to 1.5 mL microtube and centrifuge it at 10,000 RPM for 2 minutes. Discard the supernatant and resuspend cells in 15 mL N6-AS liquid medium (3.98 g/L N6 basal salt mixture, 0.8 mg/L KI, 0.025 mg/L $CoCl_2.6H_2O$, 0.025 mg/L $CuSO_4.5H_2O$, 0.25 mg/L $NaMoO_4.2H_2O$, 2 mg/L Glycine, 100 mg/L Myo-inositol, 5 mg/L Thiamine.HCl, 1 mg/L Pyridoxine.HCl, 1 mg/L Nicotinic acid, 1 g/L Casamino acid, 30 g/L Sucrose, 10 g/L Glucose, 2 mg/L 2,4-Dichloro-Phenoxyacetic Acid, pH 5.6). Adjust cell density with the N6-AS medium. The density can be measured by a spectrophotometer (use 750 µL aliquot for reading). The optimal $OD_{600}$ reading varies significantly depending on *Agrobacterium* strains and sometimes vectors. The optimal reading means that there is no over-growth of *Agrobacterium* cells in at least 3 day co-cultivation. The optimum $OD_{600}$ for rice is 0.2. Mix rice calli with *Agrobacterium* cells. This is done in a 50 mL sterile conical tube. Place tubes in a sterile 1 gallon plastic bag and place horizontally on a shaker for 30 minutes. Pipette out solution with 10-mL pipette. Transfer calli onto autoclaved Kimwipes™ to remove excess solution. Remove any agar media if present, since *Agrobacterium* will grow faster in agar. Culture calli on autoclaved filter paper placed on the N6-AS semi-solid medium (N6-AS medium containing 4 g/L Gel rite). Each 100 mm×20 mm dish contains 10-20 mL N6-AS media. Seal the dish with antifungal tape. Cover plates with aluminum foil because acetosyringone present in the media is light sensitive. Co-culture calli and *Agrobacterium* cells at 22° C. in the dark until *Agrobacterium* mass can be seen by the naked eye.

Selection of Transformed Calli

Transfer the infected calli with a sterile, disposable spatula to a sterile 50 mL tube containing 35 mL sterile distilled water. Shake the tube for a few seconds and pipette out the water. Repeat washing 3 times or more if necessary, until solution becomes clear. For the final wash, add carbenicillin at the concentration of 500 mg/L. Transfer calli with a disposable blue ino-loop onto 2 layers thick of autoclaved Kimwipes™ paper in a large spherical Petri plate to blot. Culture calli on dishes containing semisolid N6-P medium with 250 mg/L carbenicillin at 28° C. under cold fluorescent light for 6 days. Each 100 mm×20 mm dish contains 30 mL N6-P medium, use approximately 4 dishes of calli for each construct. Dishes are sealed with antifungal tape. Transfer calli from the resting media on to the selection media containing 250 mg/L carbenicillin and 5 mg/L purified Bialaphos™ (for selection of BAR gene) or 100 mg/L Paromomycin sulfate (for selection of NPTII gene) for 14 days. For second round of selection, subculture calli for another 14 days. Transformed calli can typically be seen clearly at the end of this selection. Third selection is done if the second selection does not produce enough resistant calli.

Regeneration of Transgenic Plants

Transfer independent resistant calli to the N6-R plant regeneration medium (3.98 g/L N6 basal salt mixture, 0.8 mg/L KI, 0.025 mg/L $CoCL_2.6H_2O$, 0.025 mg/L $CuSO_4.5H_2O$, 0.25 mg/L $NaMoO_4.2H_2O$, 2 mg/L Glycine, 100 mg/L Myo-inositol, 5 mg/L Thiamine.HCl, 1 mg/L Pyridoxine.HCl, 1 mg/L Nicotinic acid, 1 g/L Casamino acid, 25 g/L Sucrose, 25 g/L Sorbitol, 2 mg/L 6-Benzylaminopurine, 0.05 mg/L 1-Naphthaleneacetic acid, 7 g/L Agarose (Omnipur), pH 5.6). Each 100 mm×20 nm m dish contains 30 mL N6-R medium, 4 or 6 callus lines on each dish. Dishes are sealed with antifungal tape. Culture calli at 28° C. under cold fluorescent light until shoots and roots are formed. Typically, shoots should be seen within 3 weeks. Transfer plantlets to Magenta boxes containing 30 mL ½ MS1A (2.165 g/L MS salts, 1 ml/L of 1000×B5 vitamins stock, 15 g/L Sucrose, 5 g/L Agar, pH 5.7). Grow plantlets at 28° C. under old fluorescent light for 10-14 days.

Ten independently transformed events (plantlets) are selected with one tiller from each event evaluated for GFP Expression in the T0 generation.

Preparation of Soil Mixture: 6 L Potting Soil (Farmers Organic Potting Soil, Chino, Calif.) is mixed with 4 L Turface in a cement mixer to make a 60:40 soil mixture. To the soil mixture is added 1 tsp Marathon 1% granules (Hummert, Earth City, Mo.), 2 Tbsp OSMOCOTE® 14-14-14 (Hummert, Earth City, Mo.). Once a month 1 Tbsp Peters fertilizer 20-20-20 (J.R. Peters, Inc., Allentown, Pa.) is mixed well in 3 gallons of water and poured into the bottom flat to fertilize. 6-inch diameter Azalea pots are used for transplanting with 1-2 plants per pot.

Planting: Plants growing in magenta boxes are carefully pulled from MS agar rice media. Plant roots are cleaned and divided into single tillers ensuring that each tiller has a viable root and no residual callus material. The tillers are screened for GFP expression and one positively expressing tiller per independently transformed event is transplanted to soil and grown to maturity for further analysis.

Plant Maintenance: Plants are well watered throughout the duration of the lifecycle. The bottom of the flat is cleaned and new water added twice a week. Approximately 21 days after planting, rice is sub-irrigated with Peter's fertilizer at a concentration of 1 Tsp per 3 gallons of water. Plants are analyzed for GFP expression at the T0 seedling, T0 mature and T1 generations.

GFP Assay and Imaging

The polynucleotide sequences of the present document were tested for promoter activity using Green Fluorescent Protein (GFP) assays in the following manner.

Each isolated nucleic acid described in the Sequence Listing was cloned into a Ti plasmid vector, CRS380_Binary_DF_EGFP using appropriate primers tailed with SfiI restriction sites. Standard PCR reactions using these primers and genomic DNA were conducted. The resulting product was isolated, cleaved with SfiI and cloned into the SfiI site of an appropriate vector, such as, CRS380_Binary_DF_EGFP (see FIG. 1).

GFP Assay in Rice Callus

GFP expression in rice callus can be observed as early as 4-7 days after co-cultivation. The rice callus used for co-cultivation is observed under Zeiss Stemi SVII APO dissecting microscope for GFP expression. For viewing GFP expression we use GFP 500 filter in the microscope. The images observed under the microscope can be transferred, captured and stored to a computer using the Axiocam (Zeiss) camera and Axiovision software.

GFP Assay in T0 Seedling

Each independently transformed event is divided into single tillers which then undergo Typhoon scanner laser imaging. One positively GFP-expressing tiller per event is selected for subsequent GFP analysis by Confocal microscopy and ultimately for transplantation for further mature tissue analysis.

Typhoon Scan: Plants are initially scanned with a Typhoon Scanner to examine the GFP expression of the plants on a global level. If expression is present, images are collected by Typhoon scanning laser imaging and scanning laser confocal microscopy. Scanned images from the Typhoon scanner are taken as 2-D images of the entire plant and can be opened using the program ImageQuant.

Confocal Microscopy: Tissues are dissected by eye or under magnification using INOX 5 grade forceps and placed on a slide with water and coversliped. An attempt is made to record images of observed expression patterns at earliest and latest stages of development of tissues listed below. Specific tissues will be defined as having positive expression or no expression.

| | |
|---|---|
| Main Culm | Bundle sheath, endodermis, epidermis, internode, ligule, node, not-specific, pericycle, phloem, sclerenchyma layer, vasculature, xylem. |
| Root | Cortex, epidermis, not-specific, root cap, vascular. |
| Panicle | Flag leaf, not-specific, ovary, peduncle, primary branch, rachilla, rachis, spikelet |
| Spikelet | Aleurone layer, anther, carpel, embryo, endosperm, filament, flag leaf, floret (palea), leamma, not-specific, ovule, pedicle, pollen, seed, stigma |
| Leaf | Epidermis, leaf blade, leaf sheath, magin, mesophyll, not-specific, petiole, primordia, stipule, stomata, trichome, vasculature |
| Meristem | Floral meristem, not-specific, shoot apical meristem, vegetative meristem |

Ziess UV stereoscope: Reproductive tissues that are too large to use with the confocal microscope are prepared using a dissection microscope under high magnification using INOX 5 grade forceps and placed on a slide. An attempt is made to record images of observed expression patterns in mature rice reproductive tissues. Auxiovision is the program used for capturing GFP images under the following settings:

GFP: 4900 ms, gain=3, resolution=1300×1030 interpolated

Bright field: 100 ms, conversion=square root, resolution=1300×1030 interpolated.

T0 Mature

These are the T0 plants resulting from a single tiller from each independent transformation event having predetermined positive GFP expression. These are screened between stage 3-5 (i.e. between late vegetative to panicle initiation and floral maturation), which is 6-8 weeks of age. At this stage the mature plant possesses young panicle inflorescence to adolescent flowers, fully expanded leaves, multiple nodes and mature stem and root tissue. The plants are initially imaged using the Typhoon scanner and then imaged in detail using the Leica Confocal microscope and Ziess UV Stereoscope to allow examination of the mature plants on a global level.

T1 Seedling

Seed is collected from the T0 plants and stored for further use in induction experiments.

Results

Derivatives of PD3525, PD3559, PD3560, PD3561, PD3562, PD3564, PD3565, PD3573, PD3574, PD3578, PD3579, PD3580, PD3567, PD3655, PD3720, PD3786, PD3805, or PD3812 are generated by introducing mutations into the nucleotide sequence set forth in SEQ ID NO:1-SEQ ID NO:18 as disclosed in U.S. Pat. No. 6,747,189, incorporated herein by reference. A plurality of mutagenized DNA segments derived from PD3525, PD3559, PD3560, PD3561, PD3562, PD3564, PD3565, PD3573, PD3574, PD3578, PD3579, PD3580, PD3567, PD3655, PD3720, PD3786, PD3805, or PD3812, including derivatives with nucleotides deletions and modifications are generated and inserted into a plant transformation vector operably linked to a GFP marker gene. Each of the plant transformation vectors are prepared essentially as described above, except that the full length promoter is replaced by a mutagenized derivative. Plants (e.g., rice plants) are transformed with each of the plant transformation vectors and analyzed for expression of the GFP marker to identify those mutagenized derivatives having promoter activity.

Fragments of PD3525, PD3559, PD3560, PD3561, PD3562, PD3564, PD3565, PD3573, PD3574, PD3578, PD3579, PD3580, PD3567, PD3655, PD3720, PD3786, PD3805, or PD3812 are isolated by designing primers to clone fragments of the promoters set forth in SEQ ID NO:1-18. A plurality of cloned fragments of PD3525, PD3559, PD3560, PD3561, PD3562, PD3564, PD3565, PD3573, PD3574, PD3578, PD3579, PD3580, PD3567, PD3655, PD3720, PD3786, PD3805, or PD3812 ranging in size from 50 nucleotide up to the full length sequence set forth in SEQ ID NO:1-18 are obtained using PCR. For example, a fragment of PD3525 of about 50, 100, 150, 200, 250, 300, 350, 400, 450, 500, 550, 600, 650, 700, 750, 800, 850, 900, 950, 975, or 990 nucleotides in length from various parts of PD3525 (SEQ ID NO:1) are obtained and inserted into a plant transformation vector operably linked to a GFP marker gene. Such fragments of PD3535 can include one or more of a GARE1OSREP1, ACIIPVPAL2, ABRERATCAL, and TATABOX motif.

A fragment of PD3559 of about 50, 75, 100, 125, 150, 175, 190, or 200 nucleotides in length from various parts of PD3559 (SEQ ID NO:2) are obtained and inserted into a plant transformation vector operably linked to a GFP marker gene. Such fragments of PD3559 can include one or more of an AUXRETGA2GMGH3, ACGTABREMOTIFA2OSEM, TATCCAYMOTIFOSRAMY3D, AMYBOX1, and GAREAT motif.

A fragment of PD3560 of about 50, 100, 150, 200, 250, 275, 300, 350, 375, or 390 nucleotides in length from various parts of PD3560 (SEQ ID NO:3) are obtained and inserted into a plant transformation vector operably linked to a GFP marker gene. Such fragments of PD3560 can include one or more of an ARE1, SBOXATRBCS, TE2F2NTPCNA, GADOWNAT, ACGTABREMOTIFA2OSEM, and TATABOX motif.

A fragment of PD3561 of about 50, 100, 150, 200, 250, 275, 300, 350, 375, 390, 400, or 410 nucleotides in length from various parts of PD3561 (SEQ ID NO:4) are obtained and inserted into a plant transformation vector operably linked to a GFP marker gene. Such fragments of PD3561 can include one or more of a ROOTMOTIFTAPDX1, RYREPEATVFLEB4, and TATABOX motif.

A fragment of PD3562 of about 50, 100, 150, 200, 250, 300, 350, 400, 450, 500, 550, 600, 650, 700, 725, or 750 nucleotides in length from various parts of PD3562 (SEQ ID NO:5) are obtained and inserted into a plant transformation vector operably linked to a GFP marker gene. Such fragments of PD3562 can include one or more of a CARGCW8GAT, INRNTPSADB, and TATABOX2 motif.

A fragment of PD3564 of about 50, 100, 150, 200, 250, 300, 350, 400, 450, 500, 550, 600, 650, 700, 750, 800, 850, 900, 950, 975, 990, 1000, or 1010 nucleotides in length from various parts of PD3564 (SEQ ID NO:6) are obtained and inserted into a plant transformation vector operably linked to a GFP marker gene. Such fragments of PD3564 can include one or more of a MARTBOX, RYREPEATVFLEB4, NRRBNEXTA, TRANSINITMONOCOTS, TATABOXOSPAL, and P1BS motif.

A fragment of PD3565 of about 50, 100, 150, 200, 250, 300, 350, 400, 450, 500, 550, 600, 650, 700, 750, 800, 850, 900, 950, 975, 990, 1000, 1010, 1025, 1050, or 1060 nucleotides in length from various parts of PD3565 (SEQ ID NO:7) are obtained and inserted into a plant transformation vector operably linked to a GFP marker gene. Such fragments of PD3565 can include one or more of a CARGCW8GAT, P1BS, and TATABOX motif.

A fragment of PD3573 of about 50, 100, 150, 200, 250, 300, 350, 400, 450, 500, 550, 600, 650, 700, 750, 800, 850, 900, 950, 975, 990, or 1000 nucleotides in length from various parts of PD3573 (SEQ ID NO:8) are obtained and inserted into a plant transformation vector operably linked to a GFP marker gene. Such fragments of PD3573 can include one or more of a ROOTMOTIFTAPDX1, ATHB6COREAT, TATABOX2, and UP2ATMSD motif.

A fragment of PD3574 of about 50, 100, 150, 200, 250, 300, 350, 400, 450, 500, 550, 600, 650, 700, 750, 800, 850, 900, 950, 975, 990, 1000, 1050, 1100, 1150, 1200, 1250, 1300, 1350, or 1400 nucleotides in length from various parts of PD3574 (SEQ ID NO:9) are obtained and inserted into a plant transformation vector operably linked to a GFP marker gene. Such fragments of PD3574 can include one or more of a PRECONSCRHSP70A, IBOXCORENT, AGCBOXNPGLB, UP2ATMSD, and TATABOX4 motif.

A fragment of PD3578 of about 50, 100, 150, 200, 250, 300, 350, 400, 450, 500, 550, 600, 650, 700, 750, 800, 850, 900, 950, 975, 990, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, or 2475 nucleotides in length from various parts of PD3578 (SEQ ID NO:10) are obtained and inserted into a plant transformation vector operably linked to a GFP marker gene. Such fragments of PD3578 can include one or more of an IBOXCORENT, ERELEE4, ABREATRD22, P1BS, and TATABOX motif.

A fragment of PD3579 of about 50, 100, 150, 200, 250, 300, 350, 400, 450, 500, 550, 600, 650, 700, 750, 800, 850, 900, 950, 975, 990, 1000, 1050, 1100, 1150, 1200, 1250, 1300, 1350, 1400, 1450, 1500, 1550, 1600, 1650, 1700, 1750, 1800, 1850, 1900, 1950, 2000, 2050, or 2075 nucleotides in length from various parts of PD3579 (SEQ ID NO:11) are obtained and inserted into a plant transformation vector operably linked to a GFP marker gene. Such fragments of PD3579 can include one or more of a CACGCAATGMGH3 and UPRMOTIFIIAT motif. For example, a fragment of PD3579 can contain nucleotides 1 to 896 of SEQ ID NO:11.

A fragment of PD3580 of about 50, 100, 150, 200, 250, 300, 350, 400, 450, 500, 550, 600, 650, 700, 750, 800, 850, 900, 950, 975, 990, 1000, 1050, 1100, 1150, 1200, 1250, 1300, 1350, 1400, 1450, 1500, 1550, 1600, 1650, 1700, 1750, 1800, 1850, 1900, 1950, or 1975 nucleotides in length from various parts of PD3580 (SEQ ID NO:12) are obtained and inserted into a plant transformation vector operably linked to a GFP marker gene. Such fragments of PD3580 can include one or more of a PRECONSCRHSP70A, ACIIPVPAL2, TATABOX4, CAAT-box, CAATBOX1, and UPRMOTIFIIAT motif. For example, a fragment can contain nucleotides 501 to 2000 of SEQ ID NO:12.

A fragment of PD3567 of about 50, 100, 150, 200, 250, 300, 350, 400, 450, 500, 550, 600, 650, 700, 750, 800, 850, 900, 950, 975, 990, 1000, 1050, 1100, 1150, 1200, 1250, or 1275 nucleotides in length from various parts of PD3567 (SEQ ID NO:13) are obtained and inserted into a plant transformation vector operably linked to a GFP marker gene. Such fragments of PD3567 can include one or more of a RYREPEATVFLEB4, SPHCOREZMC1, and AGCBOXNPGLB motif.

A fragment of PD3655 of about 50, 100, 150, 200, 250, 300, 350, 400, 450, 500, 550, 600, 650, 700, 750, 800, 850, 900, 950, or 975 nucleotides in length from various parts of PD3655 (SEQ ID NO:14) are obtained and inserted into a plant transformation vector operably linked to a GFP marker gene. Such fragments of PD3655 can include one or more of a ROOTMOTIFTAPDX1, RYREPEATVFLEB4, P1BS, and TATABOX1 motif. For example, a fragment of PD3655 can contain nucleotides 501 to 990 of SEQ ID NO:14.

A fragment of PD3720 of about 50, 100, 150, 200, 250, 300, 350, 400, 450, 500, 550, 600, 650, 700, 750, 800, 850, 900, 950, 975, 990, 1000, 1050, 1100, 1150, 1200, 1250, 1300, 1350, 1400, 1450, or 1475 nucleotides in length from various parts of PD3720 (SEQ ID NO:15) are obtained and inserted into a plant transformation vector operably linked to a GFP marker gene. Such fragments of PD3720 can include one or more of a SBOXATRBCS, MYBbindingsite, ATHB1ATCONSENSUS, ABRE, E2FAT, PRECONSCRHSP70A, MYBPLANT, and E2FCONSENSUS motif. For example, a fragment of PD3720 can contain nucleotides 702 to 1500 of SEQ ID NO:15.

A fragment of PD3786 of about 50, 100, 150, 200, 250, 300, 350, 400, 450, 500, 550, 600, 650, 700, 750, 800, 850, 900, 950, 975, 990, 1000, 1050, 1100, 1150, 1200, 1250, 1300, 1350, 1400, 1450, 1500, 1550, 1600, 1650, 1700, 1750, 1800, 1850, or 1875 nucleotides in length from various parts of PD3786 (SEQ ID NO:16) are obtained and inserted into a plant transformation vector operably linked to a GFP marker gene. Such fragments of PD3786 can include one or more of a P1BS, ABREZMRAB28, SP8BFIBSP8BIB, CCA1ATLHCB1, BOXIIPCCHS, and LRENPCABE motif.

A fragment of PD3805 of about 50, 100, 150, 200, 250, 300, 350, 400, 450, 500, 550, 600, 650, 700, 750, 800, 850, 900, 950, 975, or 990 nucleotides in length from various parts of PD3805 (SEQ ID NO:17) are obtained and inserted into a plant transformation vector operably linked to a GFP marker gene. Such fragments of PD3805 can include one or more of a P1BS, MYBGAHV, and CEREGLUBOX2PSLEGA motif.

A fragment of PD3812 of about 50, 100, 150, 200, 250, 300, 350, 400, 450, 500, 550, 600, 650, 700, 750, 800, 850, 900, 950, 975, 990, 1000, 1050, 1100, 1150, 1200, 1250, 1300, 1350, 1400, 1450, or 1475 nucleotides in length from various parts of PD3812 (SEQ ID NO:18) are obtained and inserted into a plant transformation vector operably linked to a GFP marker gene. Such fragments of PD3812 can include one or more of a CACGCAATGMGH3 or UPRMOTIFIIAT motif. For example, a fragment of PD3812 can contain nucleotides 353 to 1248 of SEQ ID NO:18.

Each of the plant transformation vectors are prepared essentially as described above except that the full length sequence is replaced by a fragment containing one or more of the motifs described herein. Arabidopsis plants are transformed with each of the plant transformation vectors and analyzed for expression of the GFP marker to identify those fragments having promoter activity.

The invention being thus described, it will be apparent to one of ordinary skill in the art that various modifications of the materials and methods for practicing the document can be made. Such modifications are to be considered within the scope of the document as defined by the following claims.

Each of the references from the patent and periodical literature cited herein is hereby expressly incorporated in its entirety by such citation.

What is claimed is:

1. A vector construct comprising:
   a) a first nucleic acid comprising a regulatory region having 98 percent or greater sequence identity to the nucleotide sequence set forth in SEQ ID NO: 5 or a fragment of SEQ ID NO: 5 that is at least 300 nucleotides in length, said regulatory region comprising the CARGCW8GAT motif, the INRNTPSADB motif, and the TATABOX2 motif of SEQ ID NO: 5, wherein said regulatory region has promoter activity; and
   b) a second nucleic acid to be transcribed,
   wherein said first and second nucleic acids are heterologous to each other and are operably linked, and wherein said regulatory region directs transcription of said second nucleic acid.

2. The vector construct according to claim 1, wherein said first nucleic acid comprises the nucleotide sequence set forth in SEQ ID NO: 5.

3. The vector according to claim 1, wherein said second nucleic acid comprises a nucleic acid sequence that encodes a polypeptide.

4. The vector according to claim 3, wherein said second nucleic acid is operably linked to said first nucleic acid in sense orientation.

5. The vector according to claim 4, wherein said second nucleic acid is transcribed into an RNA molecule that expresses the polypeptide encoded by said second nucleic acid.

6. The vector according to claim 1, wherein said second nucleic acid is operably linked to said first nucleic acid in antisense orientation.

7. The vector according to claim 1, wherein said second nucleic acid is transcribed into an interfering RNA against an endogenous gene.

8. A plant or plant cell transformed with the vector construct of claim 1.

9. The plant or plant cell of claim 8, wherein said first nucleic acid consists of the nucleotide sequence set forth in SEQ ID NO: 5.

10. A plant or plant cell transformed with the vector construct according to claim 2.

11. A method of directing transcription by combining, in an environment suitable for transcription:
   a) a first nucleic acid comprising a regulatory region having 98 percent or greater sequence identity to the nucleotide sequence set forth in SEQ ID NO: 5 or a fragment of SEQ ID NO: 5 that is at least 300 nucleotides in length, said regulatory region comprising the CARGCW8GAT motif, the INRNTPSADB motif, and the TATABOX2 motif of SEQ ID NO: 5, wherein said regulatory region has promoter activity; and
   b) a second nucleic acid to be transcribed;
wherein said first and second nucleic acids are heterologous to each other and operably linked, and wherein said regulatory region directs transcription of said second nucleic acid.

12. The method of claim 11, wherein said first nucleic acid molecule consists of the nucleotide sequence set forth in SEQ ID NO: 5.

13. The method of claim 11, wherein said operably linked first and second nucleic acids are inserted into a plant cell and said plant cell is regenerated into a plant.

14. A transgenic plant comprising the vector according to claim 2.

15. The transgenic plant according to claim 14, wherein said second nucleic acid encodes a polypeptide of agronomic interest.

16. A seed of the plant according to claim 14, wherein said seed comprises said vector.

17. A transgenic plant comprising the vector according to claim 1.

* * * * *

SEQUENCE LISTING

```
<160> NUMBER OF SEQ ID NOS: 26

<210> SEQ ID NO 1
<211> LENGTH: 1100
<212> TYPE: DNA
<213> ORGANISM: Sorghum bicolor
<220> FEATURE:
<221> NAME/KEY: misc_feature
<222> LOCATION: (1)..(1100)
<223> OTHER INFORMATION: Ceres Promoter PD3525
<220> FEATURE:
<221> NAME/KEY: misc_feature
<222> LOCATION: (80)..(86)
<223> OTHER INFORMATION: Motif name: GARE1OSREP1
<220> FEATURE:
<221> NAME/KEY: misc_feature
<222> LOCATION: (122)..(128)
<223> OTHER INFORMATION: Motif name: GARE1OSREP1
<220> FEATURE:
<221> NAME/KEY: misc_feature
<222> LOCATION: (201)..(212)
<223> OTHER INFORMATION: Motif name: ACIIPVPAL2
<220> FEATURE:
<221> NAME/KEY: misc_feature
<222> LOCATION: (327)..(333)
<223> OTHER INFORMATION: Motif name: ABRERATCAL
<220> FEATURE:
<221> NAME/KEY: misc_feature
<222> LOCATION: (461)..(467)
<223> OTHER INFORMATION: Consensus TATABOX
<220> FEATURE:
<221> NAME/KEY: misc_feature
<222> LOCATION: (501)..(561)
<223> OTHER INFORMATION: 5' untranslated region
<220> FEATURE:
<221> NAME/KEY: misc_feature
<222> LOCATION: (1069)..(1100)
```

<223> OTHER INFORMATION: 5' untranslated region
<220> FEATURE:
<221> NAME/KEY: misc_feature
<222> LOCATION: (562)..(1068)
<223> OTHER INFORMATION: Intron

<400> SEQUENCE: 1

```
accggtgata ataggtgagg caagtatttt attttccatt tctaggttga ggctggcaaa      60
tttctaggag aaaaatgaat aacagaaata ctactactgt actgataaaa cgtagtactg     120
ataacagaat atactacacg gttatacgga agaaaatgat ggagagagaa atgttaggtg     180
aagtgggccc agcatcactg gggggttggt ggccgtgggg ttggtgagag acaacaagg      240
ctacagcgct gctactgcct accggccagc gggtggcttc ttcgccgacg tggggccatc     300
cggtcagtgt ccgcccgcca tgtcctcacg tgcatgcctg cccgactcgc caaaatactt     360
tccgcaccga agctcaggta cacccgcacc cgcacccgca ccccgtgcgg acccacctct     420
gacctccttc ccccggatcc gcgcccggcg ccagcgcggc tataaatggc ggagccccca     480
gcagtgccga gaccccgtgc cacacatccc cgttcgcatc ttctccctct tgccggtccc     540
gaataaagag cagcagcgca aggtgagttc cagcctgctg cttctctctc tcgttggttc     600
gtcatttccc cgttcgtcgt gcttctcccg aggttcgtcc gtccgtgcgt gcgtggtttt     660
gtcatttgtg cgcgcatgct tgggggggaga tgctgcaaac cttggttggg tcttcctcgg     720
ttggatctga tggtcgccac gggatggccg atcccggtgt gggttttggt gattattatg     780
cttatttagg gattctgtag atctggggtg ccgtttaaat ttgagattca gtggacaaat     840
tttgggatttttttttttaaa aaatttggt gtctcggagg gagggttcac catttttatta     900
gatctcgtag cctctgcatt tggagttgtc tgtggtgctc tgattttcag atctcacggc     960
atcggtttaa taagtatatt tgttggtcat ccaattcgaa tgtgcggtgg atctgcggat    1020
ggtttctgat tgtctgaatt cctttttttt ttcaaataaa atttgcagag gttaatttat    1080
cgcccgagaa gaagaaagca                                                1100
```

<210> SEQ ID NO 2
<211> LENGTH: 219
<212> TYPE: DNA
<213> ORGANISM: Sorghum bicolor
<220> FEATURE:
<221> NAME/KEY: misc_feature
<222> LOCATION: (1)..(219)
<223> OTHER INFORMATION: Ceres Promoter PD3559
<220> FEATURE:
<221> NAME/KEY: misc_feature
<222> LOCATION: (24)..(32)
<223> OTHER INFORMATION: Motif name: AUXRETGA2GMGH3
<220> FEATURE:
<221> NAME/KEY: misc_feature
<222> LOCATION: (24)..(30)
<223> OTHER INFORMATION: Motif name: ACGTABREMOTIFA2OSEM
<220> FEATURE:
<221> NAME/KEY: misc_feature
<222> LOCATION: (52)..(58)
<223> OTHER INFORMATION: Motif name: TATCCAYMOTIFOSRAMY3D
<220> FEATURE:
<221> NAME/KEY: misc_feature
<222> LOCATION: (135)..(141)
<223> OTHER INFORMATION: Motif name: AMYBOX1
<220> FEATURE:
<221> NAME/KEY: misc_feature
<222> LOCATION: (135)..(141)
<223> OTHER INFORMATION: Motif name: GAREAT
<220> FEATURE:
<221> NAME/KEY: misc_feature
<222> LOCATION: (140)..(219)
<223> OTHER INFORMATION: 5' untranslated region

<400> SEQUENCE: 2

```
cttccgtgct ctaacgaggg ggcgccacgt cagcagcgag gatcctgagc ctatccatga    60
ccatgagtgg ccgctgcagg ccacgacctg cccttgtgg ccacaagctt taaggccctt   120
gcgcttgcgc tccctaacaa atcacgcctg aaacacccac cacacacacc actctgcaca   180
cacagaccga cgacgacgac ggcacaggcg ccatacgaa                          219
```

<210> SEQ ID NO 3
<211> LENGTH: 400
<212> TYPE: DNA
<213> ORGANISM: Sorghum bicolor
<220> FEATURE:
<221> NAME/KEY: misc_feature
<222> LOCATION: (1)..(400)
<223> OTHER INFORMATION: Ceres Promoter PD3560
<220> FEATURE:
<221> NAME/KEY: misc_feature
<222> LOCATION: (124)..(134)
<223> OTHER INFORMATION: Motif name: ARE1
<220> FEATURE:
<221> NAME/KEY: misc_feature
<222> LOCATION: (202)..(209)
<223> OTHER INFORMATION: Motif name: SBOXATRBCS
<220> FEATURE:
<221> NAME/KEY: misc_feature
<222> LOCATION: (240)..(247)
<223> OTHER INFORMATION: Motif name: TE2F2NTPCNA
<220> FEATURE:
<221> NAME/KEY: misc_feature
<222> LOCATION: (308)..(314)
<223> OTHER INFORMATION: Motif name: GADOWNAT
<220> FEATURE:
<221> NAME/KEY: misc_feature
<222> LOCATION: (308)..(314)
<223> OTHER INFORMATION: Motif name: ACGTABREMOTIFA2OSEM
<220> FEATURE:
<221> NAME/KEY: misc_feature
<222> LOCATION: (280)..(286)
<223> OTHER INFORMATION: Consensus TATABOX
<220> FEATURE:
<221> NAME/KEY: misc_feature
<222> LOCATION: (311)..(400)
<223> OTHER INFORMATION: 5' untranslated region

<400> SEQUENCE: 3

```
gaagctctga acaagctgaa ccaagtaata gaatgcagag ttgcacgaat tcacagccat    60
gccattcacc gtggctccct gaccacccaa gtagagggga aaaaacttgc caaatgcaaa   120
gacagtgaca tcgctaccgg tgaaaaatgg cctgctggga taccttatcc ggcgccctcc   180
aatgggcaca cgccatggcc gcacctccaa atcctcgtct cctccaccac taacctcgca   240
ttcccgcggc cccaccatat ctgccaagtc agcatcccac tatatacca actccattaa   300 tcaagcagac acgtcgtagc tgccaagatc aagaggaaac acaaacaccc acagccgccg   360
cgccttccag tactcgagga agaggaacac cagcagcgcc                         400
```

<210> SEQ ID NO 4
<211> LENGTH: 420
<212> TYPE: DNA
<213> ORGANISM: Sorghum bicolor
<220> FEATURE:
<221> NAME/KEY: misc_feature
<222> LOCATION: (1)..(420)
<223> OTHER INFORMATION: Ceres Promoter PD3561
<220> FEATURE:
<221> NAME/KEY: misc_feature
<222> LOCATION: (179)..(183)
<223> OTHER INFORMATION: Motif name: ROOTMOTIFTAPOX1
<220> FEATURE:

```
<221> NAME/KEY: misc_feature
<222> LOCATION: (182)..(186)
<223> OTHER INFORMATION: Motif name: ROOTMOTIFTAPOX1
<220> FEATURE:
<221> NAME/KEY: misc_feature
<222> LOCATION: (225)..(232)
<223> OTHER INFORMATION: Motif name: RYREPEATVFLEB4
<220> FEATURE:
<221> NAME/KEY: misc_feature
<222> LOCATION: (229)..(236)
<223> OTHER INFORMATION: Motif name: RYREPEATVFLEB4
<220> FEATURE:
<221> NAME/KEY: misc_feature
<222> LOCATION: (292)..(299)
<223> OTHER INFORMATION: Consensus TATABOX
<220> FEATURE:
<221> NAME/KEY: misc_feature
<222> LOCATION: (324)..(420)
<223> OTHER INFORMATION: 5' untranslated region

<400> SEQUENCE: 4
gatctttagc acttgagcat gttactagat accagcagcc aacccatatg acaagttact     60
aaactgaata aatgatcaac catcaagtga gaacaaacat caacatgcat cgaccaatgc    120
agcaatcttg gccactagtg ctgttctaca atgaaactta tttctcgagt accacacaaa    180
tatattcgtc gaacaaatcc agatcactca tctaatcgcc ctcacatgca tgcatgctca    240
cgggaatgtt gaacgctcca ccaactaccc agtattgcac cgatgtttct cctataaaag    300
caacattcaa gcgccaccac tagccatctc aagcgcttag ccatcagtga ttattaaggc    360
acaccataat cactctgcct cgtgctagtg atcaagcaac tgcttcagta ctctgtagca    420

<210> SEQ ID NO 5
<211> LENGTH: 759
<212> TYPE: DNA
<213> ORGANISM: Sorghum bicolor
<220> FEATURE:
<221> NAME/KEY: misc_feature
<222> LOCATION: (1)..(759)
<223> OTHER INFORMATION: Ceres Promoter PD3562
<220> FEATURE:
<221> NAME/KEY: misc_feature
<222> LOCATION: (415)..(424)
<223> OTHER INFORMATION: Motif name: CARGCW8GAT
<220> FEATURE:
<221> NAME/KEY: misc_feature
<222> LOCATION: (580)..(587)
<223> OTHER INFORMATION: Motif name: INRNTPSADB
<220> FEATURE:
<221> NAME/KEY: misc_feature
<222> LOCATION: (417)..(423)
<223> OTHER INFORMATION: Motif name: TATABOX2
<220> FEATURE:
<221> NAME/KEY: misc_feature
<222> LOCATION: (630)..(759)
<223> OTHER INFORMATION: 5' untranslated region

<400> SEQUENCE: 5
tgacatcgct tcgaatacgt ggtattagag aattagataa attatatatt aattagtaga     60
accaggcact tcatttcttg attatcttat tctgggtcaa gattataaac tctgaatgtt    120
tgtaaatttc ttgcaccaat caggtccgca cagtctctat gaacaagttg ccgaagttcc    180
cacagggaat tgatgattgt gacacattaa tcatggaggc attgcaagtc tttgagcttg    240
taactaggac aatggtgttc tgagtttgag actgcttcta tacatgagaa aaatcaagat    300
ttatgtttgt gtgctatgca ctaaaaaaaa agagattctt cttgcatggc cttatgattt    360
tgtaattata tataataata tttggatttt taattttttt gtatttactt atcccttata    420
aatgtttaga ggaaggtggc caagaagacg tcgaagtccc aatcagctga tcagaatgct    480
```

-continued

| | |
|---|---|
| tccaagtgga cagatgaaag aaggagagga gagcatccag dacaggatag ggctgtcgcc | 540 |
| cccctccaca catgccaaaa accatcccat tcccagcacc tcatttctcg tcgtctttgt | 600 |
| atgctccatt agcagactga tgaagcacaa gtttcacact tgagcatact cattcaacca | 660 |
| tccatccgaa gcaaacaaac tcccatcctt ctctctctct cttgtctgta tgcttgcctg | 720 |
| gttttgaatt ttcttttaaa ataaaaaagg aagagaggc | 759 |

<210> SEQ ID NO 6
<211> LENGTH: 1020
<212> TYPE: DNA
<213> ORGANISM: Sorghum bicolor
<220> FEATURE:
<221> NAME/KEY: misc_feature
<222> LOCATION: (1)..(1020)
<223> OTHER INFORMATION: Ceres Promoter PD3564
<220> FEATURE:
<221> NAME/KEY: misc_feature
<222> LOCATION: (453)..(462)
<223> OTHER INFORMATION: Motif name: MARTBOX
<220> FEATURE:
<221> NAME/KEY: misc_feature
<222> LOCATION: (480)..(487)
<223> OTHER INFORMATION: Motif name: RYREPEATVFLEB4
<220> FEATURE:
<221> NAME/KEY: misc_feature
<222> LOCATION: (693)..(700)
<223> OTHER INFORMATION: Motif name: NRRBNEXTA
<220> FEATURE:
<221> NAME/KEY: misc_feature
<222> LOCATION: (832)..(839)
<223> OTHER INFORMATION: Motif name: RYREPEATVFLEB4
<220> FEATURE:
<221> NAME/KEY: misc_feature
<222> LOCATION: (853)..(860)
<223> OTHER INFORMATION: Motif name: TRANSINITMONOCOTS
<220> FEATURE:
<221> NAME/KEY: misc_feature
<222> LOCATION: (884)..(890)
<223> OTHER INFORMATION: Motif name: TATABOXOSPAL
<220> FEATURE:
<221> NAME/KEY: misc_feature
<222> LOCATION: (907)..(914)
<223> OTHER INFORMATION: Motif name: P1BS
<220> FEATURE:
<221> NAME/KEY: misc_feature
<222> LOCATION: (914)..(1020)
<223> OTHER INFORMATION: 5' untranslated region

<400> SEQUENCE: 6

| | |
|---|---|
| tgtccaattg agatgacggc tatggtttaa gtagaaacaa aaggaaagag cgtggagcaa | 60 |
| tacggagatt ccttgtgaca aatctgatca caagctcttc aattcattaa ctatatatag | 120 |
| tcaccacagg caatgtaaaa aatatagcct ctttcgtgac atcgaattgg atcaatggaa | 180 |
| catcggtcaa ggcaattgaa ccgctgttac atcaaaagac tcgaaggaaa aaatacacgg | 240 |
| tccaaaaggc tatgttagat gaattggcca catataggtg agttctcaga ttttgtgagc | 300 |
| ctgtgggagg ctatatattg tttagttccg aaaacatttt ggttttggaa actgtagcat | 360 |
| tttcgttttt atttgacaaa cattgtccaa ttatagagta actaggctta aaagattcat | 420 |
| ctcgtgattt acagataaac tgtgcaatta gttttatttt ttgtttatat ttagtgctcc | 480 |
| atgcatgtgc cccaagattc gatgtgacag tgaatcttga aaaattttg gattttgggg | 540 |
| tgaactaaac aaggcctcat tcgattaatc agtgaggcgg gtgatgagat taaatgacgc | 600 |
| ttaactgttt aatttattat taagtcgtgt taggcggctg ctatttatta agtttgctgc | 660 |
| tgctgctgct gctgatgatg aattcactct gcatccacta accactgcat atgtgtattt | 720 |

| | |
|---|---|
| ccatccacat cctccatctg cctcctgccc caacacccca accacctcct cctgcccggc | 780 |
| tcttaactgt acgatgatga tgttctaccg aaagaaacag catgcacaca ccatgcatga | 840 |
| catctgtcat cagccattgt agctctcaga tcgatctcaa gcctatttaa ggaccaacat | 900 |
| ttcactgcat attctcctca ccagctagca cttgctctca ctgcattcca aagctagcat | 960 |
| actagcacac agtcaggcac tcagatcact cagcacacac gaatagctcg atcgatcgac | 1020 |

<210> SEQ ID NO 7
<211> LENGTH: 1075
<212> TYPE: DNA
<213> ORGANISM: Sorghum bicolor
<220> FEATURE:
<221> NAME/KEY: misc_feature
<222> LOCATION: (1)..(1075)
<223> OTHER INFORMATION: Ceres Promoter PD3565
<220> FEATURE:
<221> NAME/KEY: misc_feature
<222> LOCATION: (294)..(303)
<223> OTHER INFORMATION: Motif name: CARGCW8GAT
<220> FEATURE:
<221> NAME/KEY: misc_feature
<222> LOCATION: (394)..(403)
<223> OTHER INFORMATION: Motif name: CARGCW8GAT
<220> FEATURE:
<221> NAME/KEY: misc_feature
<222> LOCATION: (666)..(673)
<223> OTHER INFORMATION: Motif name: P1BS
<220> FEATURE:
<221> NAME/KEY: misc_feature
<222> LOCATION: (883)..(891)
<223> OTHER INFORMATION: Consensus TATABOX
<220> FEATURE:
<221> NAME/KEY: misc_feature
<222> LOCATION: (917)..(1075)
<223> OTHER INFORMATION: 5' untranslated region

<400> SEQUENCE: 7

| | |
|---|---|
| actacgtggt gatacgttta atcagtgctt tatcctatat acaaaacagc ccttttttaac | 60 |
| cagaatatag tggataaaata gaggacggtc gaccgcttag caaaagaacc aaaaccactt | 120 |
| aaaaattaat taaagagata ttactccaac aaataaggtt gaagatacat gtagtagcta | 180 |
| gattttgtaa tgcgatctgc ttttttgcttc tctgattagc ttttgtgtgt tgtcatcatc | 240 |
| ttccctcctg gttagttaat tacttaaatt ataattcatt ttactttttt gaccaaatat | 300 |
| ttgtctactt gtcttattca aaataaaaaa aaatgtaaaa tatcacttct tttattgtga | 360 |
| cttgctttat taataaaagt tcttcaagta tgacttaaat ttgcatatat ttgcacatat | 420 |
| tttttttaaaa aaaaaaacaa gtcatcaaac tttcagtcaa aaaagttcaa atgaattata | 480 |
| aattgaaact caggtagtag ctctttgcat tgcctgccct ctccctcaac gaaaccaagt | 540 |
| gacgaagtag gacaggaacc atcgttccgt tcatgcctgt cctgaccgag tcaaagcttt | 600 |
| gctggcaatg tgattgaatt gaattgcttg atgttagctc gtcaccttga cagcgacatc | 660 |
| ctctggcata tccggaattt gagaactccg gtcgcaaaga acaagcatcc agcggctctg | 720 |
| ccaatgccca agaagcttca tcacaccttta ttagctagag ctagccatgg catgcactat | 780 |
| gcaggacagc tccagtccag gtccatacat acctgcactg caatgcttgt cttgaccgaa | 840 |
| gcttcctcct catccatggc agtaggttga gctgcttgct cactatatat acagcaccat | 900 |
| ccatgccgag ctctccatct caattcatca gctgcaagct agctagcctt cactcaagca | 960 |
| tcacaaaacc ctactactgc caccttcagc acctgcatag atacatatat acaaacactt | 1020 |
| cacaacaatc tatctgctcg atcgtcttca tcaattccca agccaataat caaca | 1075 |

<210> SEQ ID NO 8
<211> LENGTH: 1000
<212> TYPE: DNA
<213> ORGANISM: Sorghum bicolor
<220> FEATURE:
<221> NAME/KEY: misc_feature
<222> LOCATION: (1)..(1000)
<223> OTHER INFORMATION: Ceres Promoter PD3573
<220> FEATURE:
<221> NAME/KEY: misc_feature
<222> LOCATION: (120)..(124)
<223> OTHER INFORMATION: Motif name: ROOTMOTIFTAPOX1
<220> FEATURE:
<221> NAME/KEY: misc_feature
<222> LOCATION: (392)..(396)
<223> OTHER INFORMATION: Motif name: ROOTMOTIFTAPOX1
<220> FEATURE:
<221> NAME/KEY: misc_feature
<222> LOCATION: (522)..(526)
<223> OTHER INFORMATION: Motif name: ROOTMOTIFTAPOX1
<220> FEATURE:
<221> NAME/KEY: misc_feature
<222> LOCATION: (779)..(787)
<223> OTHER INFORMATION: Motif name: ATHB6COREAT
<220> FEATURE:
<221> NAME/KEY: misc_feature
<222> LOCATION: (813)..(819)
<223> OTHER INFORMATION: Motif name: TATABOX2
<220> FEATURE:
<221> NAME/KEY: misc_feature
<222> LOCATION: (951)..(958)
<223> OTHER INFORMATION: Motif name: UP2ATMSD

<400> SEQUENCE: 8

| | | | | | |
|---|---|---|---|---|---|
| atctcatgat | atatgtatag | ctcgaatctc | catgtggact | aatcttcctt | catatctcaa | 60 |
| atgaaagtat | tacttctcaa | aatgttgtcg | ttaattacta | aaaacttgaa | ttgggaacca | 120 |
| atatggtttc | agattactac | gcatgcatac | gtcgtgtaga | ctcgtggcac | gaaaacgaaa | 180 |
| gagaaatggg | aaggaaaaaa | aactctgcca | ttctccaatt | gatgtctaaa | cgcacacctc | 240 |
| tacaccgcgt | acccatcgac | catatcaaaa | ataaagttca | agacctgaca | cgtgctttgt | 300 |
| tcaaagatcg | cgagctccca | ttacgcaaat | ggttgctcca | aaagtttgag | caaatttaag | 360 |
| gtggatggtg | acatttcctc | atgtacagcg | tatattgtcc | gcccctctc | ttaccagttc | 420 |
| gtcgcttaag | aacaaaacac | agttattata | taaatccatc | cctttccact | ctgacgattt | 480 |
| tcgttataga | ttaatacgca | cgcaccaaac | tgattagtgt | taatataaaa | tccgatccat | 540 |
| gatcgaagaa | tgttcgatca | agcaccgttc | gttgctcctc | aagatctgaa | gaagtacagc | 600 |
| ggggaaaaaa | tgttgatgtg | gagtgtggac | caatgcaagt | cgacgaggtc | tatgcatgcg | 660 |
| tagttttgag | cacgcgattg | gatgactaca | aattggaggc | caactagcca | ctgctttgga | 720 |
| tttggtctct | cttagactcg | gcacggtatg | taatttccca | actgacactt | gctaacacca | 780 |
| attattagtc | gcgacgttta | gagatgcaca | tgtataaata | gaaactcaac | tggtcatcag | 840 |
| cccatcacca | ctactcgctc | gttctctcct | gtttcagctc | agctcagctc | tcagatagtt | 900 |
| gcagtgttgg | aagctagttg | cactgatcaa | ccgagctttg | ctgtcggaaa | tagggtttaa | 960 |
| tcgagtgatc | atcgctttta | tcggttggtg | gcaaatgaac | | | 1000 |

<210> SEQ ID NO 9
<211> LENGTH: 1428
<212> TYPE: DNA
<213> ORGANISM: Sorghum bicolor
<220> FEATURE:
<221> NAME/KEY: misc_feature
<222> LOCATION: (1)..(1428)
<223> OTHER INFORMATION: Ceres Promoter PD3574
<220> FEATURE:

```
<221> NAME/KEY: misc_feature
<222> LOCATION: (22)..(45)
<223> OTHER INFORMATION: Motif name: PRECONSCRHSP70A
<220> FEATURE:
<221> NAME/KEY: misc_feature
<222> LOCATION: (38)..(61)
<223> OTHER INFORMATION: Motif name: PRECONSCRHSP70A
<220> FEATURE:
<221> NAME/KEY: misc_feature
<222> LOCATION: (60)..(83)
<223> OTHER INFORMATION: Motif name: PRECONSCRHSP70A
<220> FEATURE:
<221> NAME/KEY: misc_feature
<222> LOCATION: (153)..(159)
<223> OTHER INFORMATION: Motif name: IBOXCORENT
<220> FEATURE:
<221> NAME/KEY: misc_feature
<222> LOCATION: (216)..(222)
<223> OTHER INFORMATION: Motif name: AGCBOXNPGLB
<220> FEATURE:
<221> NAME/KEY: misc_feature
<222> LOCATION: (299)..(306)
<223> OTHER INFORMATION: Motif name: UP2ATMSD
<220> FEATURE:
<221> NAME/KEY: misc_feature
<222> LOCATION: (306)..(312)
<223> OTHER INFORMATION: Motif name: AGCBOXNPGLB
<220> FEATURE:
<221> NAME/KEY: misc_feature
<222> LOCATION: (359)..(365)
<223> OTHER INFORMATION: Motif name: TATABOX4
<220> FEATURE:
<221> NAME/KEY: misc_feature
<222> LOCATION: (390)..(1428)
<223> OTHER INFORMATION: 5' untranslated region

<400> SEQUENCE: 9
cggggatttt ggaccttct tccgacgaca gattccccac taccgtttgg ctcgccgtcg     60
cgatcaagaa gcctagcagt gcaccgtcct tcacatattt ttttttcttt tgatttcaaa    120
aaaggaagcg ccgtttcccg aacgaagaaa aagataaggt atggaacgag tgaccgcgcg    180
aggcagcgcg ggtggagtgg gccccagggc agggtagccg ccaaggcagg gccgtccgta    240
ggcgctacga aagctggagg agttcctgtt cgcatgatga caatcgcacg gccacggcaa    300
accctagccg ccggggcaggt cggtccccgc gcgggggggcg gcggcgcggg gggcgcgcta   360
tataaacaga gcccttcatc cgatgcctcc aacccatctg gcgacctcga tcccctcccc    420
tgttggttct gtctgttgac ttccccccat cgaggtaaag tactcgctcg attcctcttc    480
cgtcctccga tccgggcggg gtgcttgatt tgttatcatt cacggttctg attcaattgt    540
ttctatcaag ttttgtccga attctttgat gctcgattca ttattagtct tcaaatttct    600
ctgaattgtt ccctagcttt tatcctccac gcatatgtac tagtatacta gcagaattgt    660
tccatagctt ttgtcctcca tgcatatact agtagtaccc aaaatcttgt gctggccgat    720
cgctcttgtc ccgcagcaat caatcgtttt tctttctttt acttttctga taataaagca    780
gatagatcaa atcaaatagt tatgatacac ataatatata tcatggcatc atccacactt    840
gattaaatcc aaaactggta tacacataat atatatcatg gcatcatcca cacttgatta    900
aatccaaaac tggtactgga gatgcgacta gtgtgcccat tgtctaatgg aaaagacaga    960
gggtctcgtc tcctatctca tcggaagggg ccgggccttc tgatataggt tcgaatccta   1020
ttgggtgctt ctattctagt ttctgcatct ccagtttaat ttgatccact gccaggtcag   1080
attgccacca ctcactcaca taacctgctt atatctgtta ctgttttgt tgctgtatgt    1140 ttctttatag tatattcatt tggcaattgt attgaataat caggtcggtt gctatgaatt   1200
actatggatg aatactgact tcagggtctc tgttttgtct ctgttttcct gatcacttta   1260
```

-continued

```
ttctaaataa aagaacaatt aatctagcag tctgcttatg tatatatgct tctaatttac      1320
tgctaaaaaa tcaatctatc aactagtatt tttgtgtgac tgcgttctct atgtatcctt      1380
ctgctgatgt ttgtgaatac agctagctag tcagctggtc ccgttgcc                   1428
```

<210> SEQ ID NO 10
<211> LENGTH: 2500
<212> TYPE: DNA
<213> ORGANISM: Sorghum bicolor
<220> FEATURE:
<221> NAME/KEY: misc_feature
<222> LOCATION: (1)..(2500)
<223> OTHER INFORMATION: Ceres Promoter PD3578
<220> FEATURE:
<221> NAME/KEY: misc_feature
<222> LOCATION: (1472)..(1478)
<223> OTHER INFORMATION: Motif name: IBOXCORENT
<220> FEATURE:
<221> NAME/KEY: misc_feature
<222> LOCATION: (1565)..(1572)
<223> OTHER INFORMATION: Motif name: ERELEE4
<220> FEATURE:
<221> NAME/KEY: misc_feature
<222> LOCATION: (2193)..(2202)
<223> OTHER INFORMATION: Motif name: ABREATRD22
<220> FEATURE:
<221> NAME/KEY: misc_feature
<222> LOCATION: (2270)..(2277)
<223> OTHER INFORMATION: Motif name: ERELEE4
<220> FEATURE:
<221> NAME/KEY: misc_feature
<222> LOCATION: (2353)..(2360)
<223> OTHER INFORMATION: Motif name: P1BS
<220> FEATURE:
<221> NAME/KEY: misc_feature
<222> LOCATION: (2391)..(2396)
<223> OTHER INFORMATION: Consensus TATABOX
<220> FEATURE:
<221> NAME/KEY: misc_feature
<222> LOCATION: (2426)..(2485)
<223> OTHER INFORMATION: 5' untranslated region
<220> FEATURE:
<221> NAME/KEY: misc_feature
<222> LOCATION: (1801)..(2500)
<223> OTHER INFORMATION: Ceres Promoter PD3775
<220> FEATURE:
<221> NAME/KEY: misc_feature
<222> LOCATION: (1282)..(1293)
<223> OTHER INFORMATION: 3' end of the upstream open reading frame

<400> SEQUENCE: 10

```
accctagcat gctggtagat tcacccggtc ttcttatctt agcgctagca gttatgcgga       60
attttgtgtg gcataaccta cactaatttt gtcttgttaa aagaattggc atgtaatgat      120
ctcgaaaaga agaaaaaagg gggcaatatc taatacgcca ctgacatttc ttgtaaaagt      180
accatttagg tacctttcca gagatcattg tattgtaaaa tggaattcac atgaccaagt      240
ttctttggta tcataacata tcatatcctt ggtgtattga taatttgata aactatcaag      300
tctttgtcca attgtagaac agttatggtg gtttacagaa acacggtccc tagcctgtga      360
gtagacttac ccaaccttaa cagaaagcca accttgtaga tgcattgaca atgattgtac      420
ctcatacttg atttggcaaa ggcattctct atacaggtcc tgagtgtgct ttgttttaag      480
ttaagagata ttagcacgca tggtactaag tttctgttat attaacatgc aaccgtagtg      540
aatttatcct tgtacttaat ttaccttgat gtgatttttgg agcgtaatat gcatctatta      600
gctttatctt ataacctgct tccacaattt acaagatcac ttgctgactc ttggtgtacc      660
atgtttgtgg atgcattgtt agttgatgac ttatatcatg agttcatatg ctgatctttc      720
```

```
aatcttctgt caagaaccac acatttgtgc taaatttcct ggaattgatt tccttatttc    780
acagagacta cctttcaccg tgggatttgt cgggagcatg gttgctacca tctatgtgtc    840
aatggtgctt catagctaca tactttctgt tttcttctcc gtgcttcagg tgataacatc    900
cttttgcact ctgcaatcct cttgcacaat gctattaggc tttcttatgc gataggcacc    960
ttcaccccTT tcagcataag tagtagtagt aggatcgtcc tctgttcttc ctgctagctg   1020
gtaggaacta actttgaaga gaacccttta ttctttgaat aaaccataga actcttatac   1080
tcagtgtgga gctttcttag tttctgcttt ctggtgactg tagttgtgag cctgacaccc   1140
tgtgatgatt tattgaacta agaaactttt cttgtacttt tttcaggtcc ttgctctagc   1200
atattatgcc atctcatact tccctggtgg atctgctgga atgaagtttc tatcatccgc   1260
ccttgtgtcc tcagtgttga gatgctttgg gcgataagtt cacctgttag ttgctttcac   1320
catctatttc atcctgttac acttttgact tttgttcata ttgacttaga gtttgataac   1380
agtgactgca ggcagtgtgc cagtgtctgt caagatattt gcatgtaact tacccaattt   1440
agtaaaatta taatggcagt cttcaaattt ctcttatcat attacatcta tgaatgctcc   1500
tccgatacca aaacctttgt tgttaggata gacttgaaca gctgtcaaga aagttaacat   1560
gaaatttgaa ttttcctgtg aaaaagggcg caacacttaa agacaataat ctgcgattag   1620
gtcatctggg aactctagac gggatgcttt ttgcatggca tggcaaatca ttttatatat   1680
atattaagta taaccataca acaatttttt tcctttccag ttctgatgcc atctgttttt   1740
actcatttag atgactgtaa tcttttttgct tctgcaggac tgcttctttc ctgtgctgat   1800
tgcagaattt ctagtcaatg atctagcaca cctttgtggc gttgtcttca taaattgtgc   1860
agcttcatta cttccagaag tttgatgcca ttttgaaagc actgaactca gctatttggt   1920
aacttgatga ttttgaggaa aggatgttgc tggaccctgc cagcactagt caggagaaaa   1980
aaagaatgta gtattcagtt gcctgcatat tggattattg gtgccacaac agcttagtct   2040
aaaattacat tgtacagaat atgtcaccaa acactgggcc acaatctatg ctcattcatg   2100
gcagaggagc gaattacatg tatgcttcat gttctcatgc tataaactga tcctgtccct   2160
acattctcct gctgggataa agtccacatc gccaccacgt gtttagtttc ccgtcttgtt   2220
tctttcactg taaagaaaaa agaaattgtt cgcacgattt tcatcagaat ttgaatttgg   2280
gtggcgcagt gcggctcccc tatccgggaa cgggtgatgg ggattccaag ggcccatgcg   2340
gccatgaatc acgtatatcc tctcaggcct gtgtggacgg ttttttggttt tataaagggt   2400
aggccactgg aaaaggcgct gctctagtgc ccggcggcca cacgcgtttg gattttgctc   2460
ctgctcccTT gatccacatc cacttctgaa aagggtcacc                         2500
```

<210> SEQ ID NO 11
<211> LENGTH: 2000
<212> TYPE: DNA
<213> ORGANISM: Sorghum bicolor
<220> FEATURE:
<221> NAME/KEY: misc_feature
<222> LOCATION: (1)..(2000)
<223> OTHER INFORMATION: Ceres Promoter PD3579
<220> FEATURE:
<221> NAME/KEY: misc_feature
<222> LOCATION: (1)..(2000)
<223> OTHER INFORMATION: Variant of Ceres Promoter PD3812 of SEQ ID NO
     18
<220> FEATURE:
<221> NAME/KEY: misc_feature
<222> LOCATION: (353)..(1148)
<223> OTHER INFORMATION: Portion of Ceres Promoter PD3812 of SEQ ID NO
     18

```
<220> FEATURE:
<221> NAME/KEY: misc_feature
<222> LOCATION: (1)..(896)
<223> OTHER INFORMATION: Ceres Promoter Candidate ID 93438196
<220> FEATURE:
<221> NAME/KEY: misc_feature
<222> LOCATION: (897)..(2000)
<223> OTHER INFORMATION: Intron
<220> FEATURE:
<221> NAME/KEY: misc_feature
<222> LOCATION: (716)..(723)
<223> OTHER INFORMATION: Motif name: CACGCAATGMGH3
<220> FEATURE:
<221> NAME/KEY: misc_feature
<222> LOCATION: (770)..(788)
<223> OTHER INFORMATION: Motif name: UPRMOTIFIIAT
<220> FEATURE:
<221> NAME/KEY: misc_feature
<222> LOCATION: (1097)..(1108)
<223> OTHER INFORMATION: Conserved motif
<220> FEATURE:
<221> NAME/KEY: misc_feature
<222> LOCATION: (837)..(896)
<223> OTHER INFORMATION: 5' untranslated region

<400> SEQUENCE: 11
actcttcgtc agtgctgatg acagaagcag ctgcccttac tctagcaacc acggtgctag      60
aagctatgta catgattgat tccactattt taacagataa tcaatagtta gtactctttc     120
taaacgggtc ttagtttgat catcatcctg atggagaatt aaatcctaca ttcaaattac     180
cagctccaag attcatggta caactatagc gattcgcaag attaccagaa tcatatggct     240
gatcaactag ctagataggc tctgagtgaa ttagtttgca atcaaatctc tcttaatagt     300
gcttgttgtc attctgctca tgagcaaaag tgtcctttac tttcgacact ctcaaatata     360
actattaact ctataatggt cctaaccgta acacgctgtt aatcatatag gccttgttca     420
gttggcaaaa attttgggtt ttaacactgt agcattttg ttttattg ataaacattg     480 tcagatgaac tgtgtaatta gttttattt ttatgtatat ttaatgcacc atacatctgc     540
cgtaaaattt gatgggatgg aaaatcttga aaattttga aactaaacaa ggccatagtt     600
tcattgtaaa aaaaaaaaca gctaagcaag atggccgaga gagccgttga cgcagagcat     660
tgaacggcat ctctctcggc tgctctcgaa tgcgctgcct gccggcatcc cggaaattgc     720
gtggcggagc ggagccgagg cgggctggtc tcacacggca cgaaaccgtc ccggcacacg     780
gcaccacgat ttttccttcc cctcccctg cccttcttt tcctcataaa tagccaccc     840 ctcctcgcct cttcccccc aactcgtctt cgtccctcgt gttgttcggc gtccacggac     900
acagcccgat cccaatccct cttctccgag cctcgtcgat cgcccccttc cctgcttca     960 aggtacggcg atcgtcctcc cgctttcgct tctcccctcc cctcctctcg attatgggtt    1020
attggggctg cgagtcatct ttctggcgat ttattatggt ctcgatctgg tggtaactgt    1080
ggcgatttat tatgggagcc ctcgatctag aagtcgagta ctctctctgg taactgtagc    1140
gatttgttat ggggctctc gatctagaag ccgagtactc tctggtaact gtgggaccct    1200
tgtagggttg ggttgttatg attatttggg cttgtgatta ggttgtatct gatgcagaat    1260
gatgtattga tcgtcctatt agattagatg gaaacaagta gggtgactct gatttatta    1320 tccttgatct cgtttgatgt ccctagctag gcctgtgcgt ctggttcgtc atactagttt    1380
tgttgttttt ggtgctggtt ctgatgcccg tccagatcaa gtcatatgaa ccagctgctg    1440
tcttattaaa tttggatctg cctgttttaa catatatgtt catatagaat tgatatgagc    1500
tagtatgaac tagctgcttg tcttattaaa tttggatctg catgtgttat atgatggatg    1560
```

-continued

```
aaatatgtgc ttaagatata tgctgcggtt ttctgccgag gctgtagctt ttgtctgatt    1620
aaagtgcatc atgcttattc gttgaactct gtggctgtct taataagaat tcatgtttgc    1680
ctgatgttgg agaaaacata cataagaatt catgtttgcc tgatgttcga gaaaatatgc    1740
atcgacctac ttagctatta cttgatgcgc atgctttgtc ctgttttgtt tgatatgcat    1800
gcttagaaag attaaaatat atgtggctgc tgtttgattc gataattctt tagcatctac    1860
ctgatgagca tgcatgctct tgttattcac tgctactgtt ccttgattct gtgccaccta    1920
catgttacat gtttatggtt gcttcttttt ctacttggtg tactactata tgcttaccct    1980
tttgtttggt ttctctgcag                                                2000
```

```
<210> SEQ ID NO 12
<211> LENGTH: 2000
<212> TYPE: DNA
<213> ORGANISM: Sorghum bicolor
<220> FEATURE:
<221> NAME/KEY: misc_feature
<222> LOCATION: (1)..(2000)
<223> OTHER INFORMATION: Ceres Promoter PD3580
<220> FEATURE:
<221> NAME/KEY: misc_feature
<222> LOCATION: (1044)..(2000)
<223> OTHER INFORMATION: Intron
<220> FEATURE:
<221> NAME/KEY: misc_feature
<222> LOCATION: (11)..(15)
<223> OTHER INFORMATION: Motif name: CAATBOX1
<220> FEATURE:
<221> NAME/KEY: misc_feature
<222> LOCATION: (326)..(344)
<223> OTHER INFORMATION: Motif name: UPRMOTIFIIAT
<220> FEATURE:
<221> NAME/KEY: misc_feature
<222> LOCATION: (501)..(2000)
<223> OTHER INFORMATION: Ceres Promoter PD3777
<220> FEATURE:
<221> NAME/KEY: misc_feature
<222> LOCATION: (535)..(558)
<223> OTHER INFORMATION: Motif name: PRECONSCRHSP70A
<220> FEATURE:
<221> NAME/KEY: misc_feature
<222> LOCATION: (765)..(776)
<223> OTHER INFORMATION: Motif name: ACIIPVPAL2
<220> FEATURE:
<221> NAME/KEY: misc_feature
<222> LOCATION: (954)..(960)
<223> OTHER INFORMATION: Motif name: TATABOX4
<220> FEATURE:
<221> NAME/KEY: misc_feature
<222> LOCATION: (986)..(990)
<223> OTHER INFORMATION: Motif name: CAAT-box
<220> FEATURE:
<221> NAME/KEY: misc_feature
<222> LOCATION: (217)..(228)
<223> OTHER INFORMATION: Conserved motif
<220> FEATURE:
<221> NAME/KEY: misc_feature
<222> LOCATION: (984)..(1043)
<223> OTHER INFORMATION: 5' untranslated region

<400> SEQUENCE: 12
cactaatcca ccaatacata acgaaaacaa taaacgaaac actattaata tccacaacaa      60
acatacattt gggtcataat catttcatac aaacattcca aacatggcat caagaaaacc     120
atcaatgaca agttccatga acaaacaaca catgcaacca aatccaaaca gatagaatga     180
aagagggaaa ggaggagcac cttggcaagt cgtcctagcc ctcgatctgg cctccctaca     240
gctgcattta ggatttaggg ttcgtgggcg aaggggagga gagagaaacc tgatgaaata     300
atggatgaag gaggaagaag ggagccgtgg ctggtattta gggggccat agctcggcgt      360
```

```
tgagtcgacc agcgccgaac tgttggacta ggcgctaatg gattcagcgc cgagctcgtg    420
ggccgtgcta gtccgtgggc cgtgacccta aacctcggcg tcaaatcact aagcgccgaa    480
atgtgcggct cggcgtcgct tcacttatcg ccgacatgtg ggccatgctg catggcgacc    540
agagtcgtcg ctgacgtggc acatgttcgg cgtcaactga cagggcgcct aagtgcctaa    600
gttcggcgtc atgtcctaac acgccgaaaa atggtctatt cctagaaaat gtttcgcgag    660
gggtctatta gtacaaaaag ttacaaaaaa ggttcaaaat gcagaaattt cacctagcgg    720
gaccgggacg ggtcatctcg ccgtctacta ctaccattta acggccacca accccggaa     780 gcaaacggcg tgaccaactt ttttttccgg aaaaattatg cggtggggac gaactccacg    840
acgacaccgc gatgcaatgc aaccgccttt cgccgcgggg cccacctgcc tcacgggacc    900
cttccgtctg tgcctgggta tggccttctc cgcccccctcc ctccctcccc gtctatataa   960
accggcaccc tccccctcgca agtccccaat ctccaatctc ccaatccaat cccgtcgaaa  1020
gaattctcct gcgagcgaaa gcaaaggagc ctgcctctcc cgatcctctc aaggtacgcg   1080
cgcgagttca cgaccgtct cgtatgattt ccctgttcgt gtttgtcggt tcgtcgcgga    1140
tctatttcat tattattagg tcttgtttgg tcgcgagagc gacgactttg acttatcgca   1200
tcctgcaatc tgtagtcgat ttcggtttga tccgcgggta gaggtgtgga tccgcgggct   1260
gtaatgagat tatttgctct cgatccgtgc tcacgcgatt ttacatgttg ttgtttggga   1320
ttatttgctc tcgatccgtg ctggcgcgat tttacatgtt gtttggttcg cttgcctgct   1380
aggttgggca cttgtgctga tgttggcatg cccgtcatcg ccaggccggc gcggccggac   1440
ctgcgtttta tggttgtaat agcgttactg ttatgtgatg atttggttta gaattgttgg   1500
ttcgcttcgt ctagttagat tattctgtcc agagggaaac ttgattgcta ctatttgttc   1560
tttagatata aatttcatc tcaattgatt tatgtgcatg atatatgact cctgctctta    1620
tgcctttgcc ttatggtgat tactgattgt catcagggat gctatatcat ggctaaagta   1680
gatactgctg cataattgct aattgcatcc tgaatatgtt actcgtgtag tgtcgaaccc   1740
aatcagtcca tctatcattt gttgccaaat cagtttgtac ctggtagttc aagcattata   1800
aatgctaatg gttctgctgc tgcttattat tatgataagc ttcacattta gttgtctaca   1860
gtgtatgatg ctgagcagct aatattcatg ggatatattt ttctgttcag atttggccag   1920
tttccttgta gcatttttt tgtatgctct agttatgaat tttgttggct taccctgctt     1980
ttgcttgttg acgtttgcag                                                2000
```

```
<210> SEQ ID NO 13
<211> LENGTH: 1296
<212> TYPE: DNA
<213> ORGANISM: Sorghum bicolor
<220> FEATURE:
<221> NAME/KEY: misc_feature
<222> LOCATION: (1)..(1296)
<223> OTHER INFORMATION: Ceres Promoter PD3567
<220> FEATURE:
<221> NAME/KEY: misc_feature
<222> LOCATION: (786)..(793)
<223> OTHER INFORMATION: Motif name: RYREPEATVFLEB4
<220> FEATURE:
<221> NAME/KEY: misc_feature
<222> LOCATION: (787)..(795)
<223> OTHER INFORMATION: Motif name: SPHCOREZMC1
<220> FEATURE:
<221> NAME/KEY: misc_feature
<222> LOCATION: (1082)..(1088)
<223> OTHER INFORMATION: Motif name: AGCBOXNPGLB
```

<400> SEQUENCE: 13

```
aagctataag cattttttgtg aatgtgaagg ctgggatgct tattccatga ttaaaaaaaa      60
tatgtcatca gctacccacc cccaaaaaac tagctattag aactctaaaa ctagccattg     120
gccatgtaga gtgtagaact tccgcacttg tcaatccaat ggttagtttc agtgttctaa     180
atttccacct ctcttgaaaa ctcacatgta tacacaaagt caagtcaatc gtgtcaattt     240
ctcatacaag atttatttat ttttatttca ctagcattta ttatgagcca tggaatctat     300
gtgatttaat gttacactaa gtctaattaa attcaacaaa ataactatc tcattaacat      360
tgacacaagt gttacacaat aaattatatg ttccgctgta aggccagtct caatgcatag     420
tttcatggcg cagttactaa gactataaac tagataaccg agccacaaga gtttcatggg     480
gatgaaactc ctctctcatc tgatgaaact ccttcattta atgactctgc caaatcagca     540
attttgctta tgtggtaccc tatttaatgt gcatgacact cccatgaaac atgcattgag     600
actggcctaa tgcatcttca tatttgctat aataattaat taaatgagag atttataacc     660
atagattttc taggtgtaga ttttttttc agagtgtagg tggacgtcac ggacagatcg      720
gagttaaggc ctcgtttagt tcgcaaaaat ttccaagatt tcctgtcaca tcgaatctttt    780
ggtcgcatgc atggagcatt aaatatagac aaaaataaaa actaactgca ccgtttatct    840
gtaatttgtg agatgaatga caatgtttgt caaataaaaa cgaaatgcta cagtagccaa    900
aaataaaaaa ttttgcgaac taaacaaggc ctaactgtgc caccagcccg tcactcctca    960
tgtcatcgtc attttgtcaa aaaaaaaga tgaggaagaa gaagaagtcc ccgcagcgtc   1020
gacctaccta aactggtcaa ttgccaagcc gctgtactcg ataaaaaaaa aaagctgcc    1080
aagccgcctc tgacgagagc cgtgacgtcc gagcacctgc gacaacctgt ataaagtagg   1140
gccccgcgcc agtccgcaga actcgcctag acgcctacag tagacacaca cacgacacgg   1200
gcaaacccgc acaacggcac aagcaaaccg cagctcccag cgtgctcgcc atctcaccga   1260
ccgtgccgcc ggcaacaagt cagtgagcaa ctcgcc                             1296
```

```
<210> SEQ ID NO 14
<211> LENGTH: 990
<212> TYPE: DNA
<213> ORGANISM: Sorghum bicolor
<220> FEATURE:
<221> NAME/KEY: misc_feature
<222> LOCATION: (1)..(990)
<223> OTHER INFORMATION: Ceres Promoter PD3655
<220> FEATURE:
<221> NAME/KEY: misc_feature
<222> LOCATION: (27)..(31)
<223> OTHER INFORMATION: Motif name: ROOTMOTIFTAPOX1
<220> FEATURE:
<221> NAME/KEY: misc_feature
<222> LOCATION: (77)..(81)
<223> OTHER INFORMATION: Motif name: ROOTMOTIFTAPOX1
<220> FEATURE:
<221> NAME/KEY: misc_feature
<222> LOCATION: (145)..(149)
<223> OTHER INFORMATION: Motif name: ROOTMOTIFTAPOX1
<220> FEATURE:
<221> NAME/KEY: misc_feature
<222> LOCATION: (501)..(990)
<223> OTHER INFORMATION: Ceres Promoter Candidate ID 91975543
<220> FEATURE:
<221> NAME/KEY: misc_feature
<222> LOCATION: (707)..(713)
<223> OTHER INFORMATION: Motif name: RYREPEATGMGY2
<220> FEATURE:
<221> NAME/KEY: misc_feature
<222> LOCATION: (795)..(801)
<223> OTHER INFORMATION: Motif name: RYREPEATGMGY2
```

<220> FEATURE:
<221> NAME/KEY: misc_feature
<222> LOCATION: (798)..(805)
<223> OTHER INFORMATION: Motif name: P1BS
<220> FEATURE:
<221> NAME/KEY: misc_feature
<222> LOCATION: (855)..(864)
<223> OTHER INFORMATION: Motif name: TATABOX1

<400> SEQUENCE: 14

```
tgaaacatgt ttatataatg attagaatat tttaagaatt tctagatttt attttatttc      60
attttactag agataaatat tttatttgaa tttagctatc ccaatctatc ttcagaattg     120
ttttaattat ctaaaagctt agagatattt catgtggtta aaaaaaacct tatccggtac     180
ttaacatttt tctaaataaa ataaaagaga aaccaactt caaaaccact ccaaactatt      240
gacctattag ggaggtactt tgaatggttt tgaaacttta gaaggtaaaa tgtttggttt     300
tagagtttaa gaaggaaaat gcgatagttc aaagatagga taaacttttt ttttccaata    360
gtagtccaga tttcaaggac cagcggtgtg gttttagccc atcaaggact ttccaatgag    420
atcagagaag tgggccttta tatggggctt aagtagtcat aacggtcccg cccaacccat    480
ataaactatg ggctcaaaga tgcacacaca gtagctcgcc ctcccagcga atcgagctcc    540
tctgaatgct gaactccgct caccgatcgc caacgacatt atcgatcgtc accacaacct    600
tcttatggac cgagatcatt ttggcttatg gcatgttaca aggtacaaaa aggcaccgag    660
tccgccaaga tcgcccaaac agagtatcat aaaccgaaaa ctggaacatg catccgccac    720
tgcagcaatc ttgttggcta gtttgaactt cgaacccatc cagatcggca tcccgcaccg    780
tcatctcaac ctcacatgca tatgctaact agctagttga tcacagcatc gccgtgctta    840
attccagcca ccacctataa atacggcacc cgaacgccgt ctccaaccat cacaagcacc    900
tagcaatcga gccatatcaa gagctagctc ctctcgaagc tcactctgct gtgcctgtga    960
tcaagaggac acacactgca gagtgcagca                                     990
```

<210> SEQ ID NO 15
<211> LENGTH: 1500
<212> TYPE: DNA
<213> ORGANISM: Sorghum bicolor
<220> FEATURE:
<221> NAME/KEY: misc_feature
<222> LOCATION: (1)..(1500)
<223> OTHER INFORMATION: Ceres Promoter PD3720
<220> FEATURE:
<221> NAME/KEY: misc_feature
<222> LOCATION: (80)..(85)
<223> OTHER INFORMATION: Motif name: ABRE
<220> FEATURE:
<221> NAME/KEY: misc_feature
<222> LOCATION: (139)..(147)
<223> OTHER INFORMATION: Motif name: E2FAT
<220> FEATURE:
<221> NAME/KEY: misc_feature
<222> LOCATION: (167)..(190)
<223> OTHER INFORMATION: Motif name: PRECONSCRHSP70A
<220> FEATURE:
<221> NAME/KEY: misc_feature
<222> LOCATION: (269)..(276)
<223> OTHER INFORMATION: Motif name: MYBPLANT
<220> FEATURE:
<221> NAME/KEY: misc_feature
<222> LOCATION: (297)..(320)
<223> OTHER INFORMATION: Motif name: PRECONSCRHSP70A
<220> FEATURE:
<221> NAME/KEY: misc_feature
<222> LOCATION: (526)..(533)
<223> OTHER INFORMATION: Motif name: E2FCONSENSUS
<220> FEATURE:

```
<221> NAME/KEY: misc_feature
<222> LOCATION: (702)..(1500)
<223> OTHER INFORMATION: Ceres Promoter Candidate ID 93418105
<220> FEATURE:
<221> NAME/KEY: misc_feature
<222> LOCATION: (846)..(853)
<223> OTHER INFORMATION: Motif name: SBOXATRBCS
<220> FEATURE:
<221> NAME/KEY: misc_feature
<222> LOCATION: (994)..(999)
<223> OTHER INFORMATION: Motif name: MYCCONSENSUSAT
<220> FEATURE:
<221> NAME/KEY: misc_feature
<222> LOCATION: (1315)..(1323)
<223> OTHER INFORMATION: Motif name: ATHB1ATCONSENSUS

<400> SEQUENCE: 15
gcagatgcac tggctcgctc tcgtatcgta tgctacagtg cagttctcca cttccgccag      60
ccgcgtccaa tcccgcctac acgtacggta cggcgcgcgc gcgcgcgtca ggtcgaccgg     120
ccggagcgac gaaaccgagg cgggagagga acaccgcgcg ctgcctcgcc cgtgccgacc     180
gcccggtcgg gtcggtgggt gacggtggtg gcgggagtac tcctacctcc accgccaccg     240
gtaaacagag cttgcactac tagcgacggt ttggtttccg gcggccgttc cttcctgcga     300
ctgtgcgcag cgtgtgtgat gtgatggcgt ggcgccgatc tgaagccgcg ccgtgccggc     360
cgggcgctag agggcgcacc cacgcgttgc gtgagcagct ctctctgctg ctgctggccg     420
ggcggggtgt gggcggcttt caggcatctc gcgcggcacc accgcgggct cgacacgtcc     480
tgattcgggc cctgtgcgcg gcagcgaccc ggatctccgc ctcggattcg ccgcccggcc     540
cgccttggtc cacccgaccc ttccccgtct ctcgccgcgc tctcacacgg ccgaccacac     600
cgtctcgcca ccgaccggct ttttggtgct cgccagcagc gcggaaccgc cgcgtccatc     660
cgatccgggc cccctctccg gccgtgaggc gcggccaggg caaggcaaac gcatacgtac     720
gcttcgagag cctacgacac gagtcagtga tcgacgacga cggtagctag cagctgtgtt     780
gtgtattgga gggagtatat atgagtatag tagtacagta cttgtacaac agatctctac     840
cggtccacct ccacgctagt aaatgtggta tctgtcgtct gtcaagcaaa cctatcagcg     900
cccggccgcc ggtcgaaacc taggagtagc tagctaggac tagggagcct agtgaccagt     960
gggcgccggt agagcctacc tagctagggt gagcaactga ggacgacgcg caaggcgaga    1020
tccaatctgc accccacgaa agaaaagatt cttccccgcc ggcctcgctc tcccatccgt    1080
ctcgctcgtt cctctcccag ccagagcaag ctagcaggca tatagcccac caccacatgc    1140
cgcaggggtc cctcccccgc gtcgagctaa ttgagtggga gctagaaaaa cccagaggac    1200
ggacgagcag cgagcgactc ggcagcgagc gccgcgcgag ctccgtcctg tgtgcggcgt    1260
gtgtgtgtgt gtgtgtgtct gcgctagagg gtgaacggga tggatcacct tcgtcaataa    1320
ttgcagtacg aacacgcaaa tccctagctt attaagagct ctcgctgtcg ttagctactg    1380
cctactgctg gtagcgagag aaatcagcac aagggtttgc tgaggaggaa tcgtcgattt    1440
ggagaggaaa gcagcctgct gcgtgggcgt gactgatcga tcgagagaga tcagaccacc    1500
```

<210> SEQ ID NO 16
<211> LENGTH: 1989
<212> TYPE: DNA
<213> ORGANISM: Sorghum bicolor
<220> FEATURE:
<221> NAME/KEY: misc_feature
<222> LOCATION: (1)..(1989)
<223> OTHER INFORMATION: Ceres Promoter PD3786
<220> FEATURE:
<221> NAME/KEY: misc_feature

```
<222> LOCATION: (739)..(746)
<223> OTHER INFORMATION: Motif name: P1BS
<220> FEATURE:
<221> NAME/KEY: misc_feature
<222> LOCATION: (349)..(356)
<223> OTHER INFORMATION: Motif name: ABREZMRAB28
<220> FEATURE:
<221> NAME/KEY: misc_feature
<222> LOCATION: (1168)..(1174)
<223> OTHER INFORMATION: Motif name: SP8BFIBSP8BIB
<220> FEATURE:
<221> NAME/KEY: misc_feature
<222> LOCATION: (1347)..(1353)
<223> OTHER INFORMATION: Motif name: SP8BFIBSP8BIB
<220> FEATURE:
<221> NAME/KEY: misc_feature
<222> LOCATION: (1377)..(1383)
<223> OTHER INFORMATION: Motif name: SP8BFIBSP8BIB
<220> FEATURE:
<221> NAME/KEY: misc_feature
<222> LOCATION: (1509)..(1516)
<223> OTHER INFORMATION: Motif name: CCA1ATLHCB1
<220> FEATURE:
<221> NAME/KEY: misc_feature
<222> LOCATION: (1624)..(1630)
<223> OTHER INFORMATION: Motif name: BOXIIPCCHS
<220> FEATURE:
<221> NAME/KEY: misc_feature
<222> LOCATION: (1624)..(1631)
<223> OTHER INFORMATION: Motif name: LRENPCABE
<220> FEATURE:
<221> NAME/KEY: misc_feature
<222> LOCATION: (1857)..(1989)
<223> OTHER INFORMATION: 5' untranslated region

<400> SEQUENCE: 16
tctaaaccac tctaacccaa tgataacgca catgaaccca acccaaccca ttaaggctac      60
gttcggttac caggttttaa aggcccggaa gcattccaac cggaattcct tctttaattt     120
ctaatagcta gcatcaccag gaacgattcc aatccaaaat caccccctaac cgaacgagcc    180 ctaactggtt acaccatcgg gttctccacc cacttgcaca gcactgctag agcatcagca     240
gcacgcaaca aatctctgcc tgctgctctg cgccactaac tccctcgcac agtccctcgt     300
gtccgcgttc atggattttg tctcatgcat tgcaaagcct gttccaaccc acgtggtagc     360
aaacccaacc caatccaacc tgttgtttaa gcaaacctgt tacaccccat ctaaagctaa     420
cccgtttcta accccaaacc aaataaccca ttcgacatat gacccaaccc aacacttcta     480
caaacagtac atccaggctt gttaaacgct cacaaatacg atgctatgga atattggaac     540
aaaatatgat cagtagtctc cacaagctca cagattacag ttagctgaac cagaccattt     600
tctcttctcc aattgtactc cacacattga attctatcat ggtaagccat ccaaagaaaa     660
aaaaaatgta cttttaggga ggccctgcac cccaagtctc acacattctt gcatcctta     720 ctcctccaaa ggaagatgc atatacaaag atctggtagt gaattttccg tagttctcca     780
aacccctaaa cacctcatcg ctgtaacagt gtaacaggct cctccaaaac ttagacccac     840
tcttcctttt ttatttaaat atactcttat gacccaaata ctttctcctc ggaagctcac     900
aacaaatgct tgcggctaat agtgatgcta atttgttctt gagagaaaaa cgttatttcg     960
tggtagcggc ttataagctt gttcttgaga gaaaaacact gttccatggt tcggaacaat    1020 gttttttctct taagaacaaa tcaacatcag ctgcagaaat tatcgattaa atagtcgttt    1080
ctgtagctga tgctcacatc aaacatgtat tcattattct cacatcaaca aacccaatc    1140 caacaaaatc cttaggttat caatagctac tattgggcct tgtttagttc ccaaaatatt    1200
ttacataatt tttacattc cccatcacat caaatcttac gacacataca tgaagcacta    1260
```

-continued

| | |
|---|---|
| aatatacata aaagaaataa ctaattacac actttacctg taatttacgt gacgaatctt | 1320 |
| ttgaccctag ttagttcatg attggatact atttatcaaa atacaaacga aagtggtact | 1380 |
| attcttatct tataatttt tttgaaagta aacaaggcct tggcttccaa gtcaactgtc | 1440 |
| aatccaaaac ttttgattgt gcaggaagat actcctcttg tcggtcggtc actcggttag | 1500 |
| tgccgtcgag attttttttt gcctaggcca ccgtagcgca gaaaggactg gcgagtaaca | 1560 |
| agatgaaata atctagacaa cacgaaagat ctgaaccaga cacttgtcac ccctgcctgt | 1620 |
| ccgacgtggc agccagcact agccatggct gccaccgcca tccaatggca cacccgtt | 1680 |
| tgattccccc gtatcccagc atccggataa cgctggataa gagacggggc ttctcattgg | 1740 |
| ccacacccgt cccatgcggt accccgtccg tccgatccca ccgcgcggcg tatctccgcc | 1800 |
| gtcggccccc gccggcgcct cctgccaca cccgccgccc gggaccggca ggcgacagtt | 1860 |
| taatacagta caaaccaggc tgcttctggc ggcaaaaacc aacgtgctcg atcgacgatc | 1920 |
| tccccctccg ccaccactcc ccccatcgat ctctcctcag tccccccgccg ggaagctacg | 1980 |
| ctacgaagc | 1989 |

<210> SEQ ID NO 17
<211> LENGTH: 1000
<212> TYPE: DNA
<213> ORGANISM: Sorghum bicolor
<220> FEATURE:
<221> NAME/KEY: misc_feature
<222> LOCATION: (1)..(1000)
<223> OTHER INFORMATION: Ceres Promoter PD3805
<220> FEATURE:
<221> NAME/KEY: misc_feature
<222> LOCATION: (261)..(268)
<223> OTHER INFORMATION: Motif name: P1BS
<220> FEATURE:
<221> NAME/KEY: misc_feature
<222> LOCATION: (430)..(436)
<223> OTHER INFORMATION: Motif name: MYBGAHV
<220> FEATURE:
<221> NAME/KEY: misc_feature
<222> LOCATION: (484)..(491)
<223> OTHER INFORMATION: Motif name: CEREGLUBOX2PSLEGA
<220> FEATURE:
<221> NAME/KEY: misc_feature
<222> LOCATION: (716)..(723)
<223> OTHER INFORMATION: Motif name: P1BS
<220> FEATURE:
<221> NAME/KEY: misc_feature
<222> LOCATION: (930)..(1000)
<223> OTHER INFORMATION: 5' untranslated region

<400> SEQUENCE: 17

| | |
|---|---|
| atcaataata ggtgccatat gtggccaatt tgcttgctgg tggtatcaaa taaacttttt | 60 |
| ttttgcaagt gttataattt ctctctctcc catttactga gcgcaactac ttttactatg | 120 |
| caaagtatga tagctggttt aaattttat ggtatggaga tagacaatgt cagttctctt | 180 |
| ttgtaaggcc atgagaaaag aaaattccct ggaaaatcat cacaaatgat cttccagaat | 240 |
| gctatacact gctgtacgtg aatatactc atgctggcat ctaggttggg aggttttcaaa | 300 |
| attagtggtg gttgtccctt gtgcagctag gcccaagaag cagcaccatt aattctgcct | 360 |
| ttgggagcta ggactagaag tgtcacagaa ggaaccctgc agcatccagc aaacaactca | 420 |
| gagctggagt ttgttaccac caaaatactg actggaaaaa tataatgtat tttatggaat | 480 |
| aaatgaaaac tggcaattt tgacggatgc aatctctcag acatttctg ccgttggtag | 540 |
| acacgaatgg gcaacagttg gtggtgaaat ccacccacag aaaccagat tcctcatca | 600 |
| ggcaggatcc atgttaaggt caagaatgca catcccatat ttttcacatc cgatattttt | 660 |

```
tgaccacgac gttatcgcgc aaagaggaaa atgtttcttt tgcaagtttg acatggtata      720
tacacaaaaa agaaaagaga agggaaaaat atatatgtgc cagagacagg acaaaagaga      780
gggtggcaag aggattggct gattgcagca accaaagcat agccattcat ttccagaagg      840
ccagtctcca ccacacagct catatccctt gtccttgtgt gccctcaggt gcaccacctt      900
attatatgcc agctgctgca ccacttctca gtctcaacg actgtgtcat caaagagagg       960
gtagcacctg atctcatctt tcaccttcag aaccagagca                           1000
```

```
<210> SEQ ID NO 18
<211> LENGTH: 1500
<212> TYPE: DNA
<213> ORGANISM: Sorghum bicolor
<220> FEATURE:
<221> NAME/KEY: misc_feature
<222> LOCATION: (1)..(1500)
<223> OTHER INFORMATION: Ceres Promoter PD3812
<220> FEATURE:
<221> NAME/KEY: misc_feature
<222> LOCATION: (1)..(1500)
<223> OTHER INFORMATION: Variant of Ceres Promoter PD3579 of SEQ ID NO
      11
<220> FEATURE:
<221> NAME/KEY: misc_feature
<222> LOCATION: (353)..(1500)
<223> OTHER INFORMATION: Portion of Ceres Promoter PD3579 of SEQ ID NO
      11
<220> FEATURE:
<221> NAME/KEY: misc_feature
<222> LOCATION: (353)..(1248)
<223> OTHER INFORMATION: Ceres Promoter Candidate ID 93438196
<220> FEATURE:
<221> NAME/KEY: misc_feature
<222> LOCATION: (1249)..(1500)
<223> OTHER INFORMATION: Intron
<220> FEATURE:
<221> NAME/KEY: misc_feature
<222> LOCATION: (1068)..(1075)
<223> OTHER INFORMATION: Motif name: CACGCAATGMGH3
<220> FEATURE:
<221> NAME/KEY: misc_feature
<222> LOCATION: (1122)..(1140)
<223> OTHER INFORMATION: Motif name: UPRMOTIFIIAT
<220> FEATURE:
<221> NAME/KEY: misc_feature
<222> LOCATION: (1189)..(1248)
<223> OTHER INFORMATION: 5' untranslated region

<400> SEQUENCE: 18
ccatcagcgt cattgagcat agagatattt ggcgtcgcgt cgaccgatca actaccgcca       60
tccaacagaa agagaaaaaa acgattctaa ggccttgttt agttcgcaaa atttttatt       120 tttggctact gtagcatttc gttttatttg acaaacattg tccaatcacg gagtaactag      180
gctcaaaaga ttcatctcac aaattacaag taaactgtgc aattagtttt tattttcatc      240
tatatttaat gctccatgca tacgaccaaa gattcgatgt gacggagaat cttgaaattt      300
tttacgaact aaacaaggcc taaggaataa aaaaaagga aaaattgtgc aaactcttcg       360
tcagtgctga tgacagaagc agctgccctt actctagcaa ccacggtgct agaagctatg      420
tacatgattg attccactat tttaacagat aatcaatagt tagtactctt tctaaacggg      480
tcttagtttg atcatcatcc tgatggagaa ttaaatccta cattcaaatt accagctcca     540
agattcatgg tacaactata gcgattcgca agattaccag aatcatatgg ctgatcaact      600
agctagatag gctctgagtg aattagtttg caatcaaatc tctcttaata gtgcttgttg      660
tcattctgct catgagcaaa agtgtccttt actttcgaca ctctcaaata taactattaa      720
```

```
ctctataatg gtcctaaccg taacacgctg ttaatcatat aggccttgtt cagttggcaa    780 aaatttggg ttttaacact gtagcatttt tgtttttatt tgataaacat tgtcagatga    840
actgtgtaat tagtttttat ttttatgtat atttaatgca ccatacatct gccgtaaaat    900
ttgatgggat ggaaaatctt gaaaattttt gaaactaaac aaggccatag tttcattgta    960
aaaaaaaaaa cagctaagca agatggccga gagagccgtt gacgcagagc attgaacggc   1020
atctctctcg gctgctctcg aatgcgctgc ctgccggcat cccggaaatt gcgtggcgga   1080
gcggagccga ggcgggctgg tctcacacgg cacgaaaccg tcccggcaca cggcaccacg   1140
attttccctt cccctccccc tgcccttctt tttcctcata aatagccacc ccctcctcgc   1200
ctctttcccc ccaactcgtc ttcgtccctc gtgttgttcg gcgtccacgg acacagcccg   1260
atcccaatcc ctcttctccg agcctcgtcg atcgcccct tccctcgctt caaggtacgg    1320
cgatcgtcct cccgctttcg cttctccct ccctcctct cgattatggg ttattgggc    1380 tgcgagtcat ctttctggcg atttattatg gtctcgatct ggtggtaact gtggcgattt   1440
attatgggag ccctcgatct agaagtcgag tactctctct ggtaactgta gcgatttgtt   1500
```

<210> SEQ ID NO 19
<211> LENGTH: 10
<212> TYPE: DNA
<213> ORGANISM: artificial sequence
<220> FEATURE:
<223> OTHER INFORMATION: consensus sequence for ABREATRD22 motif

<400> SEQUENCE: 19 ryacgtggyr                                                           10

<210> SEQ ID NO 20
<211> LENGTH: 12
<212> TYPE: DNA
<213> ORGANISM: artificial sequence
<220> FEATURE:
<223> OTHER INFORMATION: consensus sequence for ACIIPVPAL2 motif

<400> SEQUENCE: 20
ccaccaaccc cc                                                        12

<210> SEQ ID NO 21
<211> LENGTH: 11
<212> TYPE: DNA
<213> ORGANISM: artificial sequence
<220> FEATURE:
<223> OTHER INFORMATION: consensus sequence for ARE1 motif
<220> FEATURE:
<221> NAME/KEY: misc_feature
<222> LOCATION: 7, 8, 9
<223> OTHER INFORMATION: n = A,T,C or G

<400> SEQUENCE: 21
rgtgacnnng c                                                         11

<210> SEQ ID NO 22
<211> LENGTH: 10
<212> TYPE: DNA
<213> ORGANISM: artificial sequence
<220> FEATURE:
<223> OTHER INFORMATION: consensus sequence for CARGCW8GAT motif

<400> SEQUENCE: 22 cwwwwwwwwg                                                           10

```
<210> SEQ ID NO 23
<211> LENGTH: 10
<212> TYPE: DNA
<213> ORGANISM: artificial sequence
<220> FEATURE:
<223> OTHER INFORMATION: consensus sequence for MARTBOX motif

<400> SEQUENCE: 23 ttwtwttwtt                                                              10

<210> SEQ ID NO 24
<211> LENGTH: 24
<212> TYPE: DNA
<213> ORGANISM: artificial sequence
<220> FEATURE:
<223> OTHER INFORMATION: consensus sequence for PRECONSCRHSP70A Motif
<220> FEATURE:
<221> NAME/KEY: misc_feature
<222> LOCATION: 6, 8, 9, 10, 11, 12, 13, 14, 15, 16, 17, 18, 19, 20, 21,
      22
<223> OTHER INFORMATION: n = A,T,C or G

<400> SEQUENCE: 24
scgaynrnnn nnnnnnnnnn nnhd                                              24

<210> SEQ ID NO 25
<211> LENGTH: 10
<212> TYPE: DNA
<213> ORGANISM: artificial sequence
<220> FEATURE:
<223> OTHER INFORMATION: consensus sequence for TATABOX1 Motif

<400> SEQUENCE: 25
ctataaatac                                                              10

<210> SEQ ID NO 26
<211> LENGTH: 19
<212> TYPE: DNA
<213> ORGANISM: artificial sequence
<220> FEATURE:
<223> OTHER INFORMATION: consensus sequence for UPRMOTIFIIAT Motif
<220> FEATURE:
<221> NAME/KEY: misc_feature
<222> LOCATION: 3, 4, 5, 6, 7, 8, 9, 10, 11, 12, 13, 14
<223> OTHER INFORMATION: n = A,T,C or G

<400> SEQUENCE: 26
ccnnnnnnnn nnnnccacg                                                    19
```